(12) United States Patent
Brain

(10) Patent No.: US 10,576,229 B2
(45) Date of Patent: Mar. 3, 2020

(54) ARTIFICIAL AIRWAY DEVICE

(75) Inventor: Archibald Ian Jeremy Brain, Bel Ombre (SC)

(73) Assignee: THE LARYNGEAL MASK COMPANY LIMITED, Victoria, Mahe (SC)

( * ) Notice: Subject to any disclaimer, the term of this patent is extended or adjusted under 35 U.S.C. 154(b) by 1057 days.

(21) Appl. No.: 13/254,594

(22) PCT Filed: Mar. 3, 2010

(86) PCT No.: PCT/GB2010/000379

§ 371 (c)(1),
(2), (4) Date: Nov. 10, 2011

(87) PCT Pub. No.: WO2010/100419

PCT Pub. Date: Sep. 10, 2010

(65) Prior Publication Data

US 2012/0048279 A1 Mar. 1, 2012

(30) Foreign Application Priority Data

Mar. 3, 2009 (GB) .................................. 0903654.2

(51) Int. Cl.
*A61M 16/04* (2006.01)

(52) U.S. Cl.
CPC .................................. *A61M 16/04* (2013.01)

(58) Field of Classification Search
CPC ..... A61D 7/04; A61M 16/04; A61M 16/0409; A61M 16/0415; A61M 16/0434;
(Continued)

(56) References Cited

U.S. PATENT DOCUMENTS 941,397 A 11/1909 White
2,096,831 A 10/1937 Charles
(Continued)

FOREIGN PATENT DOCUMENTS

AU 2004 260 552 A1 2/2005
CA 2012750 A1 9/1990
(Continued)

OTHER PUBLICATIONS

"Internal". Chambers 21st Century Dictionary, 2001. http://search.credoreference.com/content/entry/chambdict/internal/0 (May 17, 2015).*
(Continued)

*Primary Examiner* — Catharine L Anderson
(74) *Attorney, Agent, or Firm* — Olson & Cepuritis, Ltd.

(57) ABSTRACT

An artificial airway device to facilitate a patient's lung ventilation comprising at least one airway tube and a mask at one end of the airway tube, the mask having a peripheral formation capable of conforming to, and fitting within, the actual and potential space behind the patient's larynx to form a seal around the circumference of the laryngeal inlet, the peripheral formation surrounding a hollow interior space or lumen of the mask and the airway tube opening into the lumen of the mask, wherein the mask provides a space for drainage of gastric matter leaving the oesophagus, such space being an internal volume of the mask and providing a conduit having a volume large enough to effect a significant rise in the pressure of fluid emerging from the oesophageal sphincter while still providing an inflatable mask shape maintaining the seal around the circumference of the laryngeal inlet.

13 Claims, 60 Drawing Sheets

(58) Field of Classification Search
CPC .......... A61M 16/0445; A61M 16/0447; A61M 16/0488; A61M 16/0463; A61M 16/0477; A61M 16/049
USPC .................. 128/200.26, 204.18, 206.29, 128/207.14–207.18, 207.29
See application file for complete search history.

(56) References Cited

U.S. PATENT DOCUMENTS

| | | | |
|---|---|---|---|
| 2,099,127 A | 11/1937 | Leech | |
| 2,252,874 A | 8/1941 | Vischer | |
| 2,839,788 A | 6/1958 | Dembiak | |
| 2,862,498 A | 12/1958 | Weekes | |
| 3,124,959 A | 3/1964 | Pall | |
| 3,529,596 A | 9/1970 | Garner | |
| 3,554,673 A | 1/1971 | Schwartz et al. | |
| 3,683,908 A | 8/1972 | Michael et al. | |
| 3,794,036 A | 2/1974 | Carroll | |
| 3,931,822 A | 1/1976 | Marici | |
| 4,067,329 A | 1/1978 | Winicki et al. | |
| 4,096,759 A | 6/1978 | Desor | |
| 4,104,357 A | 8/1978 | Blair | |
| 4,116,201 A | 9/1978 | Shah | |
| 4,134,407 A | 1/1979 | Elam | |
| 4,159,722 A | 7/1979 | Walker | |
| 4,178,938 A | 12/1979 | Au et al. | |
| 4,178,940 A | 12/1979 | Au et al. | |
| 4,231,365 A | 11/1980 | Scarberry | |
| 4,256,099 A | 3/1981 | Dryden | |
| 4,285,340 A | 8/1981 | Gezari et al. | |
| 4,351,330 A | 9/1982 | Scarberry | |
| 4,445,366 A | 5/1984 | Gray | |
| 4,446,864 A | 5/1984 | Watson et al. | |
| 4,471,775 A | 9/1984 | Clair et al. | |
| 4,501,273 A | 2/1985 | McGinnis | |
| 4,509,514 A | 4/1985 | Brain | |
| 4,510,273 A | 4/1985 | Miura et al. | |
| 4,526,196 A | 7/1985 | Pistillo | |
| 4,531,330 A | 7/1985 | Phillips | |
| 4,553,540 A | 11/1985 | Straith | |
| 4,583,917 A | 4/1986 | Shah | |
| 4,630,606 A | 12/1986 | Weerda et al. | |
| 4,689,041 A | 8/1987 | Corday et al. | |
| 4,700,700 A | 10/1987 | Eliachar | |
| 4,770,170 A | 9/1988 | Sato et al. | |
| 4,793,327 A | 12/1988 | Frankel | |
| 4,798,597 A | 1/1989 | Vaillancourt | |
| 4,825,862 A | 5/1989 | Sato et al. | |
| 4,832,020 A | 5/1989 | Augustine | |
| 4,850,349 A | 7/1989 | Farahany | |
| 4,856,510 A | 8/1989 | Kowalewski et al. | |
| 4,872,483 A | 10/1989 | Shah | |
| 4,924,862 A | 5/1990 | Levinson | |
| 4,953,547 A | 9/1990 | Poole, Jr. | |
| 4,981,470 A | 1/1991 | Bombeck, IV | |
| 4,995,388 A | 2/1991 | Brain et al. | |
| 5,038,766 A | 8/1991 | Parker | |
| 5,042,469 A | 8/1991 | Augustine | |
| 5,042,476 A | 8/1991 | Smith | |
| 5,060,647 A | 10/1991 | Alessi | |
| 5,174,283 A | 12/1992 | Parker | |
| 5,203,320 A | 4/1993 | Augustine | |
| 5,218,970 A | 6/1993 | Turnbull et al. | |
| 5,235,973 A | 8/1993 | Levinson | |
| 5,237,988 A | 8/1993 | McNeese | |
| 5,241,325 A | 8/1993 | Nguyen et al. | |
| 5,241,956 A | 9/1993 | Brain | |
| 5,249,571 A | 10/1993 | Brain et al. | |
| 5,273,537 A | 12/1993 | Haskvitz et al. | |
| 5,277,178 A | 1/1994 | Dingley et al. | |
| 5,282,464 A | 2/1994 | Brain et al. | |
| 5,297,547 A | 3/1994 | Brain | |
| 5,303,697 A | 4/1994 | Brain | |
| 5,305,743 A | 4/1994 | Brain | |
| 5,311,861 A | 5/1994 | Miller et al. | |
| 5,331,967 A | 7/1994 | Akerson et al. | |
| 5,339,805 A | 8/1994 | Parker | |
| 5,339,808 A | 8/1994 | Don Michael | |
| 5,355,879 A | 10/1994 | Brain | |
| 5,361,753 A | 11/1994 | Pothmann et al. | |
| 5,391,248 A | 2/1995 | Brain et al. | |
| 5,400,771 A | 3/1995 | Pirak et al. | |
| 5,421,325 A | 6/1995 | Cinberg et al. | |
| 5,443,063 A | 8/1995 | Greenberg | |
| 5,452,715 A | 9/1995 | Boussignac et al. | |
| 5,459,700 A | 10/1995 | Jacobs | |
| 5,487,383 A | 1/1996 | Levinson | |
| 5,529,582 A | 6/1996 | Fukuhara et al. | |
| 5,546,935 A | 8/1996 | Champeau | |
| 5,546,936 A | 8/1996 | Virag et al. | |
| 5,551,420 A | 9/1996 | Lurie et al. | |
| 5,554,673 A | 9/1996 | Shah | |
| 5,569,219 A | 10/1996 | Hakki et al. | |
| 5,577,693 A | 11/1996 | Corn | |
| 5,582,167 A | 12/1996 | Joseph | |
| 5,584,290 A | 12/1996 | Brain et al. | |
| 5,599,301 A | 2/1997 | Jacobs et al. | |
| 5,623,921 A | 4/1997 | Kinsinger et al. | |
| 5,623,924 A | 4/1997 | Lindenman et al. | |
| 5,626,151 A | 5/1997 | Linden | |
| 5,632,271 A | 5/1997 | Brain | |
| RE35,531 E | 6/1997 | Callaghan et al. | |
| 5,653,229 A | 8/1997 | Greenberg | |
| 5,655,528 A | 8/1997 | Pagan et al. | |
| 5,682,880 A | 11/1997 | Brain | |
| 5,692,498 A | 12/1997 | Lurie et al. | |
| 5,694,929 A | 12/1997 | Christopher | |
| 5,711,293 A | 1/1998 | Brain | |
| 5,738,094 A | 4/1998 | Hoftman | |
| 5,743,254 A | 4/1998 | Parker | |
| 5,743,258 A | 4/1998 | Sato et al. | |
| 5,746,202 A | 5/1998 | Pagan et al. | |
| 5,771,889 A | 6/1998 | Pagan et al. | |
| 5,778,872 A | 7/1998 | Fukunaga et al. | |
| 5,791,341 A | 8/1998 | Bullard | |
| 5,794,617 A | 8/1998 | Brunell et al. | |
| 5,816,240 A | 10/1998 | Komesaroff | |
| 5,819,723 A | 10/1998 | Joseph | |
| 5,832,916 A | 11/1998 | Lundberg et al. | |
| 5,850,832 A | 12/1998 | Chu | |
| 5,855,203 A | 1/1999 | Matter | |
| 5,856,510 A | 1/1999 | Meng et al. | |
| 5,860,418 A | 1/1999 | Lundberg et al. | |
| 5,865,176 A | 2/1999 | O'Neil et al. | |
| 5,878,745 A * | 3/1999 | Brain ...................... | 128/207.15 |
| 5,881,726 A | 3/1999 | Neame | |
| 5,893,891 A | 4/1999 | Zahedi et al. | |
| 5,896,858 A | 4/1999 | Brain | |
| 5,915,383 A | 6/1999 | Pagan | |
| 5,924,862 A | 7/1999 | White | |
| 5,935,084 A | 8/1999 | Southworth | |
| 5,937,860 A | 8/1999 | Cook | |
| 5,957,133 A | 9/1999 | Hart | |
| 5,979,445 A | 11/1999 | Neame et al. | |
| 5,983,891 A | 11/1999 | Fukunaga | |
| 5,983,896 A | 11/1999 | Fukunaga et al. | |
| 5,983,897 A | 11/1999 | Pagan | |
| 5,983,987 A | 11/1999 | Pagan | |
| 5,988,167 A | 11/1999 | Kamen | |
| 5,996,582 A | 12/1999 | Turnbull | |
| 6,003,510 A | 12/1999 | Anunta | |
| 6,003,511 A | 12/1999 | Fukunaga et al. | |
| 6,003,514 A | 12/1999 | Pagan | |
| 6,012,452 A | 1/2000 | Pagan | |
| 6,021,779 A | 2/2000 | Pagan | |
| 6,050,264 A | 4/2000 | Greenfield | |
| 6,062,219 A | 5/2000 | Lurie et al. | |
| 6,070,581 A | 6/2000 | Augustine et al. | |
| 6,079,409 A | 6/2000 | Brain | |
| D429,811 S | 8/2000 | Bermudez et al. | |
| 6,095,144 A | 8/2000 | Pagan | |
| 6,098,621 A | 8/2000 | Esnouf et al. | |
| 6,110,143 A | 8/2000 | Kamen | |
| 6,116,243 A | 9/2000 | Pagan | |

(56) References Cited

U.S. PATENT DOCUMENTS

| | | |
|---|---|---|
| 6,119,695 A | 9/2000 | Augustine et al. |
| 6,131,571 A | 10/2000 | Lampotang et al. |
| 6,149,603 A | 11/2000 | Parker |
| 6,155,257 A | 12/2000 | Lurie et al. |
| 6,213,120 B1 | 4/2001 | Block et al. |
| 6,224,562 B1 | 5/2001 | Lurie et al. |
| 6,234,985 B1 | 5/2001 | Lurie et al. |
| 6,240,922 B1 | 6/2001 | Pagan |
| 6,251,093 B1 | 6/2001 | Valley et al. |
| 6,269,813 B1 | 8/2001 | Fitzgerald et al. |
| 6,315,739 B1 | 11/2001 | Merilainen et al. |
| 6,390,093 B1 | 5/2002 | Mongeon |
| 6,427,686 B2 | 8/2002 | Augustine et al. |
| 6,439,232 B1 | 8/2002 | Brain |
| 6,450,164 B1 | 9/2002 | Banner et al. |
| 6,508,250 B1 | 1/2003 | Esnouf |
| 6,631,720 B1 | 10/2003 | Brain et al. |
| 6,647,984 B1 | 11/2003 | O'Dea et al. |
| 6,651,666 B1 | 11/2003 | Owens |
| 6,705,318 B1 | 3/2004 | Brain |
| 7,004,169 B2 * | 2/2006 | Brain ............... A61M 16/04 128/207.14 |
| 7,013,899 B2 * | 3/2006 | Alfery ............... A61M 16/04 128/200.26 |
| 7,040,322 B2 | 5/2006 | Fortuna et al. |
| 7,051,096 B1 | 5/2006 | Krawiec et al. |
| 7,051,736 B2 | 5/2006 | Banner et al. |
| 7,096,868 B2 | 8/2006 | Tateo et al. |
| 7,097,802 B2 | 8/2006 | Brain et al. |
| 7,128,071 B2 | 10/2006 | Brain et al. |
| 7,134,431 B2 | 11/2006 | Brain et al. |
| 7,156,100 B1 | 1/2007 | Brain |
| 7,159,589 B2 | 1/2007 | Brain |
| 7,383,736 B2 | 6/2008 | Esnouf |
| 7,694,682 B2 * | 4/2010 | Petersen et al. ......... 128/207.15 |
| 7,895,497 B2 | 2/2011 | Pisek |
| 7,997,274 B2 * | 8/2011 | Baska ............... A61M 16/04 128/207.14 |
| 8,033,176 B2 | 10/2011 | Esnouf |
| 2002/0026178 A1 | 2/2002 | Ouchi |
| 2003/0000534 A1 | 2/2003 | Alfery |
| 2003/0051734 A1 | 3/2003 | Brain |
| 2003/0101998 A1 | 6/2003 | Zocca et al. |
| 2003/0131845 A1 | 7/2003 | Lin |
| 2003/0172925 A1 | 9/2003 | Zocca et al. |
| 2004/0089307 A1 | 5/2004 | Brain |
| 2005/0066975 A1 | 3/2005 | Brain |
| 2005/0081861 A1 | 4/2005 | Nasir |
| 2005/0274383 A1 | 12/2005 | Brain |
| 2006/0124132 A1 | 6/2006 | Brain |
| 2006/0180156 A1 * | 8/2006 | Baska ............... A61M 16/04 128/207.15 |
| 2006/0201516 A1 * | 9/2006 | Petersen et al. ......... 128/207.14 |
| 2006/0254596 A1 | 11/2006 | Brain |
| 2007/0240722 A1 | 10/2007 | Kessler |
| 2008/0123781 A1 | 5/2008 | Pisek et al. |
| 2008/0142017 A1 | 6/2008 | Brain |
| 2008/0276936 A1 | 11/2008 | Cook |
| 2009/0139524 A1 | 6/2009 | Esnouf |
| 2009/0320853 A1 | 12/2009 | Kenowski et al. |
| 2011/0220117 A1 | 9/2011 | Dubach |
| 2011/0226256 A1 | 9/2011 | Dubach |
| 2012/0174929 A1 | 7/2012 | Esnouf |
| 2012/0186510 A1 | 7/2012 | Esnouf |
| 2014/0034060 A1 | 2/2014 | Esnouf et al. |

FOREIGN PATENT DOCUMENTS

| | | |
|---|---|---|
| CA | 2067782 A1 | 5/1991 |
| CA | 2141167 | 7/1995 |
| CN | 1166138 A | 11/1997 |
| CN | 1378470 A | 11/2002 |
| CN | 2579352 | 10/2003 |
| CN | 1213777 C | 8/2005 |
| CN | 1771067 A | 5/2006 |
| CN | 1863568 A | 11/2006 |
| CN | 1863568 A | 11/2006 |
| CN | 2882657 | 3/2007 |
| CN | 2882657 Y | 3/2007 |
| CN | 101057994 A | 10/2007 |
| CN | 101057994 A | 10/2007 |
| CN | 101193677 A | 6/2008 |
| CN | 101193677 A | 6/2008 |
| CN | 100531818 C | 8/2009 |
| CN | 201516220 U | 6/2010 |
| CN | 201516220 U | 6/2010 |
| CN | 201684261 U | 12/2010 |
| CN | 201719659 U | 1/2011 |
| CN | 101991698 A | 3/2011 |
| CN | 102335478 A | 2/2012 |
| CN | 103221087 B | 8/2016 |
| DE | 2945662 A1 | 11/1979 |
| DE | 4447186 A1 | 7/1996 |
| DE | 10042172 | 4/2001 |
| EP | 0 294 200 | 12/1988 |
| EP | 0389272 A2 | 3/1990 |
| EP | 0935971 A2 | 8/1990 |
| EP | 0 389 272 | 9/1990 |
| EP | 0 402 872 | 12/1990 |
| EP | 0294200 B1 | 4/1992 |
| EP | 0 580 385 | 5/1996 |
| EP | 0712638 | 5/1996 |
| EP | 0712638 A1 | 5/1996 |
| EP | 0732116 A2 | 9/1996 |
| EP | 0732116 A2 | 9/1996 |
| EP | 0796631 | 9/1997 |
| EP | 0842672 A2 | 5/1998 |
| EP | 0845276 | 6/1998 |
| EP | 0865798 | 9/1998 |
| EP | 0922465 | 6/1999 |
| EP | 0922465 A2 | 6/1999 |
| EP | 1125595 | 8/2001 |
| EP | 1 119 386 B1 | 9/2005 |
| EP | 1800706 A1 | 12/2005 |
| GB | 1529190 | 10/1978 |
| GB | 2111394 | 7/1983 |
| GB | 2205499 | 12/1988 |
| GB | 2298797 A | 9/1996 |
| GB | 2317342 | 3/1998 |
| GB | 2317830 | 4/1998 |
| GB | 2317830 A | 4/1998 |
| GB | 2324737 A | 4/1998 |
| GB | 2318735 | 5/1998 |
| GB | 2318735 A | 5/1998 |
| GB | 2319478 | 5/1998 |
| GB | 2321854 | 8/1998 |
| GB | 2323289 | 9/1998 |
| GB | 2323290 | 9/1998 |
| GB | 2323291 | 9/1998 |
| GB | 2323292 | 9/1998 |
| GB | 2321854 A | 12/1998 |
| GB | 2334215 A | 6/1999 |
| GB | 2359996 | 9/2001 |
| GB | 2371990 A | 8/2002 |
| GB | 2405588 | 3/2005 |
| GB | 2436294 A | 3/2007 |
| GB | 2454199 A | 6/2009 |
| GB | 2436294 B | 9/2009 |
| JP | 2003039169 | 2/1991 |
| JP | 07509154 | 10/1995 |
| JP | H07-509154 | 10/1995 |
| JP | H08-000547 A | 1/1996 |
| JP | H09-505211 A | 5/1997 |
| JP | 10118182 | 5/1998 |
| JP | H10-179745 | 7/1998 |
| JP | 10216233 | 8/1998 |
| JP | 10263086 | 10/1998 |
| JP | 10277156 | 10/1998 |
| JP | 10314308 | 12/1998 |
| JP | 10323391 | 12/1998 |
| JP | 10328303 | 12/1998 |
| JP | 11128349 | 5/1999 |
| JP | 11192304 | 7/1999 |

(56) References Cited

FOREIGN PATENT DOCUMENTS

| | | |
|---|---|---|
| JP | 112068885 | 8/1999 |
| JP | 2000152995 | 6/2000 |
| JP | 2003-511108 | 3/2003 |
| JP | 2003511108 A | 3/2003 |
| JP | 2003528701 | 9/2003 |
| JP | 2005-535397 | 11/2005 |
| JP | 2005535397 A | 11/2005 |
| JP | 51770261 A | 1/2006 |
| JP | 2006-522623 A | 10/2006 |
| JP | 2006522623 | 10/2006 |
| JP | 2007514496 A | 6/2007 |
| JP | 2007-533337 | 11/2007 |
| JP | 2007533337 A | 11/2007 |
| JP | 2008136791 A | 6/2008 |
| JP | 2008-256393 A | 7/2008 |
| JP | 2008541817 A | 11/2008 |
| JP | 2008541817 A | 11/2008 |
| JP | 2008541820 A | 11/2008 |
| TW | 200706196 | 5/2005 |
| TW | 200942206 A | 1/2006 |
| WO | WO-91/03207 | 3/1991 |
| WO | WO-91/07201 | 5/1991 |
| WO | WO-91/12845 | 9/1991 |
| WO | WO-92/13587 | 8/1992 |
| WO | 94/02191 A1 | 2/1994 |
| WO | WO-94/02191 A1 | 2/1994 |
| WO | WO-95/33506 | 12/1995 |
| WO | WO-95/33506 A1 | 12/1995 |
| WO | 97/12640 A1 | 4/1997 |
| WO | WO-97/12640 | 4/1997 |
| WO | WO-97/12641 | 4/1997 |
| WO | 98/16273 A1 | 4/1998 |
| WO | WO-98/16273 | 4/1998 |
| WO | 98/50096 A1 | 11/1998 |
| WO | 99/06093 A1 | 2/1999 |
| WO | WO-99/06093 | 2/1999 |
| WO | 00/-9189 A1 | 2/2000 |
| WO | WO-00/09189 | 2/2000 |
| WO | 00/20062 | 4/2000 |
| WO | WO-00/22985 | 4/2000 |
| WO | WO-00/23135 | 4/2000 |
| WO | WO-00/61212 | 10/2000 |
| WO | 01/24860 A2 | 4/2001 |
| WO | WO-01/74431 A2 | 10/2001 |
| WO | WO-02/32490 A2 | 4/2002 |
| WO | WO-2004/030527 A1 | 4/2004 |
| WO | 2004/089453 A2 | 10/2004 |
| WO | 2004/089453 A2 | 10/2004 |
| WO | WO 2004/089453 A2 | 10/2004 |
| WO | WO-2005/011784 A1 | 2/2005 |
| WO | WO-2005/023350 A1 | 3/2005 |
| WO | WO-2005/058394 A1 | 6/2005 |
| WO | WO-2006/026237 A1 | 3/2006 |
| WO | 2006/037626 A2 | 4/2006 |
| WO | 2006/125986 A1 | 11/2006 |
| WO | WO-2006/125989 A1 | 11/2006 |
| WO | 2007/131267 A1 | 11/2007 |
| WO | WO 2008/001724 A1 | 1/2008 |
| WO | 2009026628 A | 3/2009 |
| WO | 2009/156949 A2 | 12/2009 |
| WO | 2010/060224 A1 | 6/2010 |
| WO | 2010/100419 A1 | 9/2010 |
| WO | 2010100419 A1 | 9/2010 |
| WO | WO-2012/061869 A1 | 5/2012 |
| WO | 2013/066195 A1 | 5/2013 |

OTHER PUBLICATIONS

"Sheath". The Penguin English Dictionary. 2007. http://search.credoreference.com/content/entry/penguineng/sheath/0 (May 15, 2015).*
Abdelatti, "A Cuff Pressure Controller for Tracheal Tubes and Laryngeal Mask Airway," Anaesthesia, 1999, vol. 54, pp. 981-986.
Benumof, "Laryngeal Mask Airway and the ASA Difficult Airway Algorithm," Anesthesiology, 1996, vol. 84(3), pp. 686-699.
Benumof, JL, "Management of the Adult Difficult Airway with Special Emphasis on Awake Tracheal Intubation", Anesthesiol., vol. 75, No. 6, pp. 1087-1110, 1991.
Bernhard et al., "Adjustment of Intracuff Pressure to Prevent Aspiration," Anesthesiology, 1979, vol. 50(4), pp. 363-366.
Bernhard et al., "Physical Characteristics of and Rates of Nitrous Oxide Diffusion into Tracheal Tube Currs," Anesthesiology, 1978, vol. 48, pp. 413-414.
Brain, "The Laryngeal Mask—A New Concept in Airway Management," Br. J. Anaesth., 1983, vol. 55, pp. 801-805.
Brain, "The Laryngeal Mask Airway—A Possible New Solution to Airway Problems in the Emergency Situation," Archives of Emergency Medicine, 1984, vol. 1, pp. 229-232.
Brain, "The Laryngeal Mask Airway," Anaesthesia, 1985, vol. 40, pp. 356-361.
Brain, "Three Cases of Difficult Intuition Overcome by the Laryngeal Mask Airway," Anaesthesia, 1985, vol. 40, pp. 353-355.
Brain, et al., "A new layngeal mask prototype," Anaesthesia, 1995, vol. 50, pp. 42-48.
Brimacombe, "The split laryngeal mask airway," p. 639.
Broderick et al., "The Laryngeal Mask Airway," Anaesthesia, 1989, vol. 44, pp. 238-241.
Burgard, et al., "The Effect of Laryngeal Mask Cuff Pressure on Postoperative Sore Throat Incidence," J. Clinical Anesthesia, 1996, vol. 8, pp. 198-201.
Caplan, et al., "Adverse Respiratory Events in Anesthesia: A Closed Claims Analysis", Anesthesiology 72: 828-833, 1990.
Craven, "Prevention of Hospital-Acquried Pneumonia; Measuring Effect in Ounces, Pounds, and Tonds," Annals of Internal Medicine, 1995, vol. 122(3), pp. 229-231.
Cuff-Pressure-Control DCR, 2000, LogoMed.
Davies, et al., "Laryngeal mask airway and tracheal tube insertion by unskilled personnel," The Lancet, vol. 336, pp. 977-979.
DeMello, et al., "The Use of the Laryngeal Mask Airway in Primary Anaesthesia," Anaesth. Corresp., 1990, vol. 45, pp. 793-794.
Doyle et al., "Intraoperative Awareness: A Continuing Clinical Problem," http://doyle.ibme.utoronoto.ca/anesthesia/aware.htm.
Engbers, "Practical Use of 'Diprifusor' Systems," Anaesthesia, 1998, vol. 53(1), pp. 28-34.
Eriksson et al., "Functional Assessment of the Pharynx at Rest and During Swallowing in Partially Paralyzed Humans," Anesthesiology, 1997, vol. 87(5), pp. 1035-1042.
Glen, "The Development of 'Diprifusor' : A TCI System for Propofol," Anaesthesia, 1998, vol. 53(1), pp. 13-21.
Gray et al., "Development of the Technology for 'Diprifusor' TCI Systems," Anaesthesia, 1998, vol. 53(1), pp. 22-27.
Heath, "Endotracheal Intubation Through the Laryngeal Mask—Helpful When Laryngoscopy is Difficult or Dangerous," European J. of Anaesthesiology, 1991, vol. 4, pp. 41-45.
Hickey, et al., "Cardiovascular Response to Insertion of Brain's Laryngeal Mask," Anaesthesia, 1990, vol. 45, pp. 629-633.
Inomata et al., "Transient Bilateral Vocal Cord Paralysis After Insertion of a Laryngeal Mask Airway," Anesthesiology, 1995, vol. 82, pp. 787-788.
Jacobson et al., "A Study of Intracuff Pressure Measurements, Trends and Behaviours in Patients During Prolonged Period of Tracheal Intubation," Br. J. Anaesth., 1981, vol. 53, pp. 97.
Kambic et al., "Intubation Lesions of the Larynx," Br. J. Anasth. 1978, vol. 50, pp. 587-590.
Laryngeal Mask Publications, 74 pages, Dec. 1998, www.saga.nl/lma/lmapub.htm.
Lindholm, "Prolonged Endotracheal Intubation," ACTA Anaesthesiologica Scandinavica, 1969, vol. 33, pp. 32-46.
Majumder et al., "Bilateral Lingual Nerve Injury Following the Use of the Laryngeal Mask Airway," Anaesthesia, 1998, vol. 53, pp. 184-186.
Martin, T., "Patentability of Methods of Medical Treatment: A Comparative Study", Journal of the Patent and Trademark Office Society, pp. 381-423, Jun. 2000.
Merriam Webster's Collegiate Dictionary, 10th Ed., 1997, pp. 254 and 1029, definitions of Convex and Saddle.
Miller, "A pressure regulator for the cuff of a tracheal tube," Anaesthesia, 1992, vol. 47, pp. 594-596.

(56) References Cited

OTHER PUBLICATIONS

Muthuswamy et al., "The Use of Fuzzy Integrals and Bispectral Analysis of the Electroencephalogram to Predict Movement under Anesthesia," IEEE Transactions on Biomedical Engineering,1999, vol. 46(3), pp. 290-299.

Nagai, "Unilateral hypoglossal nerve paralysis following the use of the laryngeal mask airway," Anaesthesia, 1994, vol. 49 pp. 603-604.

Neurometric Assessment of Adequacy of Intraoperative Anesthetic. Mar. 1999, 3 pages, www.pnl.gov/medical/info/neuro.htm.

Observations by Third Party Concerning European Patent Application No. 99 947 765.6-2318, European Patent Office, Munich, Germany, Jan. 18, 2005 (3 pgs.).

Patel et al., "Tracheal Tube Cuff Pressure," Anaesthesia, 1984, vol. 39, pp. 862-864.

Pennant, "Comparison of the Endotracheal Tube and Laryngeal Mask in Airway Managemet by Paramedical Personnel," Anesth. Analg., 1992, vol. 74, pp. 531-534.

Pippin et al., "Long-Term Tracheal Intubation Practice in the United Kingdom," Anaesthesia, 1983, vol. 38, pp. 791-795.

Raeder et al. "Tracheal Tube Cuff Pressures," Anaesthesia, 1985, vol. 40, pp. 444-447.

Response to Complaint Matter No. 4b 0 440-05, In the Matter of: *LMA Deutschland GmbH* versus *Ambu (Deutschland) GmbH*, Feb. 10, 2006, pp. 1-47.

Rieger et al., Anesthesiology, vol. 87, No. 1, Jul. 1997.

Seegobin et al., "Endotracheal Cuff Pressure and Tracheal Mucosal Blood Flow: Endoscopic Study of Effects of Four Large Volume Cuffs," British Medical Journal, 1984, vol. 288.

Willis et al., "Tracheal Tube Cuff Pressure," Anaesthesia, 1988, vol. 43, pp. 312-314.

Worthington, et al., "Proceedings of the Anaesthetic Research Society," Br. J. Anaesthesia, 1995, vol. 75, pp. 228P-229P.

Wynn et al, "Tongue Cyanosis after Laryngeal Mask Airway Insertion," Anesthesiology, Jun. 1994, vol. 80, No. 6, p. 1403.

Joseph R. Brimacombe, Laryngeal Mask Anesthesia, 2005, Second Edition, Saunders, Philadelphia, London, New York, Oxford, Edinburgh, St. Louis, Sydney, Toronto.

International Standard Controlled, Anaesthetic and Respiratory Equipment—Supralaryngeal Airways and Connectors, (ISO 11712) First Edition, May 15, 2009, published in Switzerland.

Miller, Donald M., A Proposed Classification and Scoring System for Supraglottic Sealing Airways: A Brief Review, 2004 by the International Anesthesia Research Society.

Benumof, Jonathan L., The Glottic Aperature Seal Airway, A New Ventilatory Device, Anesthesiology, 1998, American Society of Anesthesiologists, Inc., Lippincott-Raven Publishers.

McIntyre, John W.R., History of Anaesthesia, Oropharyngeal and Nasopharyngeal Airways: I (1880-1995), Can J Anesth 1996, 43:6, pp. 629-635.

Ishimura, Hiroshi, Minami Kouichiro, Sata, Takeyoshi, Shigematsu, Akio, and Kadoya, Tatsuo, Impossible Insertion of the Laryngeal Mask Airway and Oropharyngeal Axes, Anesthesiology, Lippincott-Raven Publishers, 1995, 83: pp. 867-869.

Brain, A.I.J., Verghese, C., Strube, P., and Brimacombe, J., A New Laryngeal Mask Prototype, Preliminary Evaluation of Seal Pressures and Glottic Isolation, Anaesthesia, 1995, vol. 50, pp. 42-48, The Association of Anaesthetists of Gt. Britain and Ireland.

Verghese, C., Berlet, J., Kapila, A., and Pollard, R., Clinical Assessment of the Single Use Laryngeal Mask Airway—The LMA—Unique, British Journal of Anaesthesia, 1998; 80: 677-679.

* cited by examiner

ARTIFICIAL AIRWAY DEVICE

CROSS-REFERENCE TO RELATED APPLICATIONS

This application is a 371 U.S. National Stage filing of PCT/GB2010/000379, filed Mar. 3, 2010, which claims priority to Great Britain Application No. 0903654.2 filed Mar. 3, 2009, which is incorporated herein by reference.

FEDERALLY SPONSORED RESEARCH OR DEVELOPMENT

Not Applicable.

BACKGROUND OF THE INVENTION

Field of the Invention

The present invention relates to an artificial airway device, and in particular to such a device which seeks to provide protection against gastric reflux and access to the gastrointestinal tract using flexible fiberoptic gastroscopes of any diameter.

For at least seventy years, endotracheal tubes comprising a long slender tube with an inflatable balloon disposed near the tube's distal end have been used for establishing airways in unconscious patients. In operation, the endotracheal tube's distal end is inserted through the mouth of the patient, into the patient's trachea. Once positioned, the balloon is inflated so as to form a seal with the interior lining of the trachea. After this seal is established, positive pressure may be applied to the tube's proximal end to ventilate the patient's lungs. Also, the seal between the balloon and the inner lining of the trachea protects the lungs from aspiration (e.g., the seal prevents material regurgitated from the stomach from being aspirated into the patient's lungs).

Although they have been successful, endotracheal tubes suffer from several major disadvantages. The principal disadvantage of the endotracheal tube relates to the difficulty of properly inserting the tube. Inserting an endotracheal tube into a patient is a procedure that requires a high degree of skill. Also, even for skilled practitioners, insertion of an endotracheal tube is sometimes difficult or not possible. In many instances, the difficulty of inserting endotracheal tubes has tragically led to the death of a patient because it was not possible to establish an airway in the patient with sufficient rapidity. Also, inserting an endotracheal tube normally requires manipulation of the patient's head and neck and further requires the patient's jaw to be forcibly opened widely. These necessary manipulations make it difficult, or undesirable, to insert an endotracheal tube into a patient who may be suffering from a neck injury.

The laryngeal mask airway device is a well known device that is useful for establishing airways in unconscious patients, and which seeks to address the above-described drawbacks associated with endotracheal tubes.

In contrast to the endotracheal tube, it is relatively easy to insert a laryngeal mask airway device into a patient and thereby establish an airway. Also, the laryngeal mask airway device is a "forgiving" device in that even if it is inserted improperly, it still tends to establish an airway. Accordingly, the laryngeal mask airway device is often thought of as a "life saving" device. Also, the laryngeal mask airway device may be inserted with only relatively minor manipulation of the patient's head, neck and jaw. Further, the laryngeal mask airway device provides ventilation of the patient's lungs without requiring contact with the sensitive inner lining of the trachea and the internal diameter of the airway tube is typically significantly larger than that of the endotracheal tube. Also, the laryngeal mask airway device does not interfere with coughing to the same extent as endotracheal tubes. Largely due to these advantages, the laryngeal mask airway device has enjoyed increasing popularity in recent years.

Description of Related Art

U.S. Pat. No. 4,509,514 describes a laryngeal mask airway device which consists of the basic parts which make up most if not all laryngeal mask airway devices, namely an airway tube opening at one end into the interior of a hollow mask portion shaped to fit readily behind the larynx of a patient. The periphery of the mask is formed by a cuff which in use forms a seal around the opening of the larynx. This enables the airway to be established effectively.

Laryngeal mask airway devices with specific provision for gastric-discharge drainage have been developed, as exemplified by U.S. Pat. No. 4,995,388 (FIGS. 7 to 10); U.S. Pat. Nos. 5,241,956; and 5,355,879. These devices generally incorporate a small-diameter drainage tube having an end located at the distal end of the mask, so as to lie against the upper end of the upper oesophageal sphincter when the mask is in place, the tube being of sufficient length to extend out of the mouth of the patient to enable active or passive removal of gastric discharge from the upper oesophageal sphincter. According to alternative proposals, the drainage tube may extend beyond the distal end of the mask, into the oesophagus itself (U.S. Pat. No. 4,995,388, FIGS. 7 and 11).

Such devices are generally useful in providing for extraction of regurgitated matter, but are still not always fully effective in preventing aspiration of gastric contents into the patient's lungs. In particular, where the gastric discharge is as a result of the patient vomiting, rather than merely from regurgitation of the gastric matter, the substantial pressure of the vomited matter may in certain cases be enough to dislodge the mask altogether, for example as illustrated by FIG. 62, even where a drainage tube is provided, potentially affecting the integrity of the artificial airway and/or resulting in the vomited matter being aspirated into the lungs of the patient.

As will be appreciated, the potential for the mask to become dislodged under vomiting is also inherent in masks such as that disclosed by U.S. Pat. No. 4,509,514, which do not feature a drainage tube, as illustrated by FIGS. 60 and 61.

Particularly where a mask does not provide for gastric drainage, and even where a gastric drainage tube is provided, there is even a risk of a potentially fatal build up of pressure in the oesophagus if vomited matter cannot be effectively vented from the oesophagus, which might for example occur if the mask becomes jammed in the pherynx.

It can be demonstrated that the human anatomy in the region of the upper oesophagus and lower pharynx provides a channel which has the characteristics of a venturi tube with respect to fluids rising forcibly from the stomach. Fluids flowing though a tube gain velocity where there is a constriction in the tube. The flowing liquid has a pressure and since the total energy of the moving liquid must remain the same, a gain in velocity must produce an equivalent loss in pressure, as illustrated by FIG. 1.

If the constriction in the tube, (represented in the human anatomy by a muscular sphincter known as the upper oesophageal sphincter), is succeeded by a second widening of the tube beyond it, (represented in the human anatomy by the lower pharyngeal region), then the fluid on arriving at this dilated region will experience a reduction in velocity and thus a gain in pressure. This phenomenon can be demonstrated by an experiment in which a light-weight ball is sucked upwards into an inverted funnel when air is blown downwards through the funnel (see FIG. 2). The same principle applies for any fluid.

Thus, an object placed in such a dilated portion of a tube through which a liquid is flowing may be drawn from the area of high pressure towards the low pressure area, in other words towards the constricted part of the tube. However, such an object cannot itself exert a pressure circumferentially against the constricted neck of the tube because were it to do so it would tend to cut off the flow of fluid by obstructing the outlet. Accordingly, in the ball experiment, the ball rises upwards until it reaches an equilibrium position, in which the gravitational force exerted on the ball is balanced by the pressure difference of the air above and below it. In order for an object placed in the fluid stream at the point of dilation of a tube to be drawn against the walls of the constricted area, it is necessary for such an object to have a similar form to the tube at the point where it dilates (see FIG. 3).

Previous LMA prototypes designed for example according to my patents U.S. Pat. No. 4,995,388 (FIGS. 7 to 10); U.S. Pat. Nos. 5,241,956; and 5,355,879 provided channels to accept regurgitant fluids arising from the oesophagus in which the diameter of the channels is approximately constant and equivalent to the diameter of the constricted area of the anatomy known as the upper oesophageal sphincter, as shown diagrammatically in FIG. 4.

Such devices, once pressed against the sphinctral region (indicated by the outer cone shape "C" of FIG. 4) provide conditions in which liquids arising from the oesophagus maintain approximately the same velocity as they pass through the tube of the device. Such devices, when correctly positioned, mimic the anatomy of the sphincter, but not that of the oesophagus, in which conditions of lower flow and therefore of higher pressure prevail during reflux of fluids. These devices therefore, are unable to act according to Bernouilli's principle unless, like the ball in FIG. 2, they remain just out of sealing contact with the walls of the cone-shaped area of the pharynx, as shown in FIG. 5 below.

Such a position of the device is very undesirable however, because the principal object of such devices having a drainage tube communicating with the oesophageal opening is to avoid leakage of any gastric fluids arising from the oesophagus from leaking around the sides of the device, because such leakage risks contamination of the larynx by these fluids with consequent grave risk to the patient.

Existing devices provided with gastric drainage tubes do not have tubes with a diameter as great as that of the oesophageal sphincter and therefore can only offer an increase in velocity of fluids entering the drainage tube, which as seen above results in a reduced pressure in the narrower tube, which will tend to cause fluids from the higher pressure region to force the distal end of the device away from the sphincter.

BRIEF SUMMARY OF THE INVENTION

The present invention seeks to ameliorate the problems associated with the prior-art described above.

The inventor has appreciated that the above-described Bernoulli Principle may potentially be favourably applied to an artificial airway device, and accordingly according to the present invention there is provided an artificial airway device to facilitate lung ventilation of a patient, comprising at least one airway tube and a mask carried at one end of the at least one airway tube, the mask having a peripheral formation capable of conforming to, and of readily fitting within, the actual and potential space behind the larynx of the patient so as to form a seal around the circumference of the laryngeal inlet, the peripheral formation surrounding a hollow interior space or lumen of the mask and the at least one airway tube opening into the lumen of the mask, wherein the mask is arranged to provide a space within the pharynx of the patient for the drainage of gastric matter leaving the oesophagus, which space approximates to the pharyngeal space that occurs within the pharynx without the mask being present in the pharynx, the effect of which is to re-establish the normal flow of matter exiting the oesphagus in the event of regurgitation or vomiting when the mask is present in the pharynx.

As will be appreciated, this potentially substantially reduces the risk of the mask becoming dislodged on the occurrence of regurgitation or vomiting of matter, allowing the integrity of the airway to be maintained, potentially greatly minimises the risk of gastric insuflation, and further potentially allows for any omitted matter to be effectively vented from the oesophagus, to minimise the risk of rupture of the oesophagus under vomiting.

It is preferred that the mask is arranged to provide a space within the pharynx when the peripheral formation creates the seal around the Laryngeal inlet.

It is preferred that the said space approximates to the pharyngeal space that occurs upon regurgitation or vomiting when the mask is not present in the pharynx.

It is preferred that the mask includes a portion which is moveable between a first condition and a second condition to provide said space. The space maybe an internal volume of the mask, or alternatively the space maybe defined by the mask and a wall of the pharynx.

In a particularly preferred embodiment, the mask may include a backplate bounded by the peripheral formation, the peripheral formation being moveable laterally on either side of the backplate to create the space and provide for sealing. The peripheral formation may include a pair of lateral wings, a wing being attached on each side of the backplate and moveable relative thereto to create the space and provide for sealing.

It is preferred that the peripheral formation comprises an inflatable cuff, or a non-inflatable cuff.

The mask may define an inlet to the space, the inlet comprising a collapsible ring, or a U-shape formation.

It is preferred that the device is provided with means for receiving part of a device already inserted in the patient to facilitate the insertion of the artificial airway device by sliding the artificial airway device along the part of the device already inserted in the patient.

Preferably, said means comprises a receiving portion defined by the exterior surface of the artificial airway device. Preferably, this receiving portion comprises a channel formed in the exterior surface of the artificial airway device.

BRIEF DESCRIPTION OF THE DRAWINGS

In order that the present invention may be more readily understood, embodiments thereof will now be described, by way of example only, with reference to the accompanying drawings, of which.

DETAILED DESCRIPTION OF THE INVENTION

Figure 1:
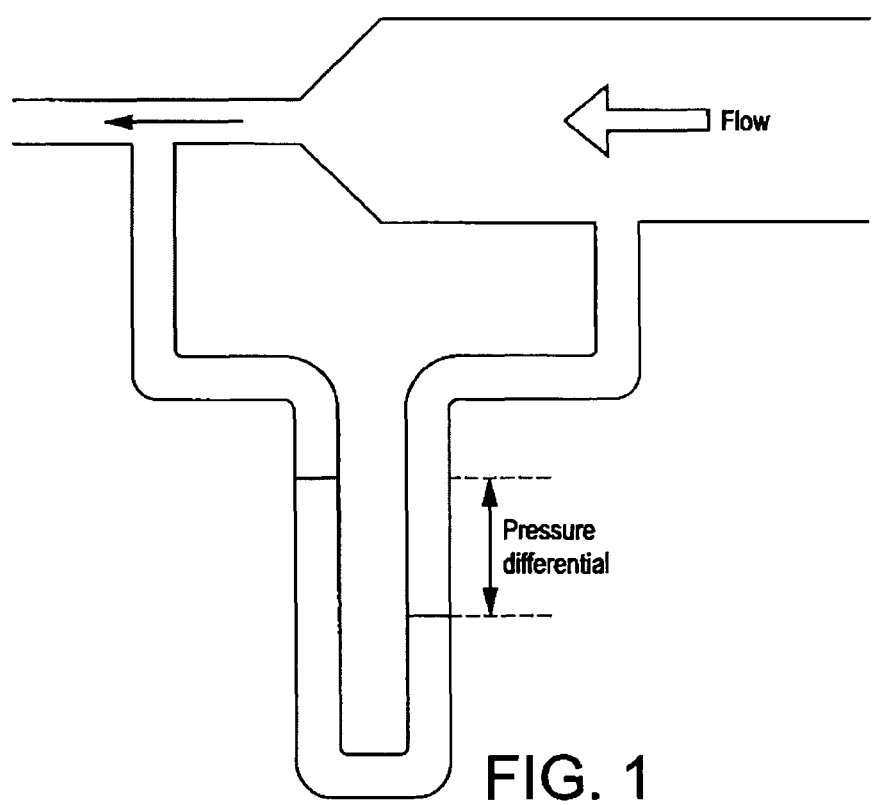
FIGS. 1 to 3 are schematic views for explanation of the Bernoulli Principle.
Figure 2:
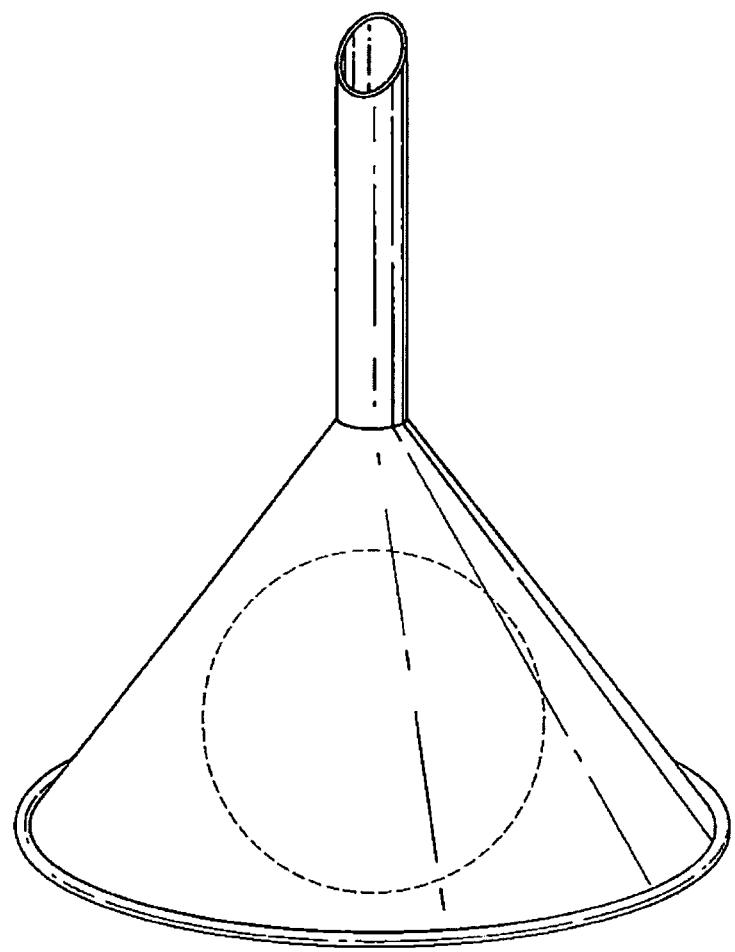
Figure 3:
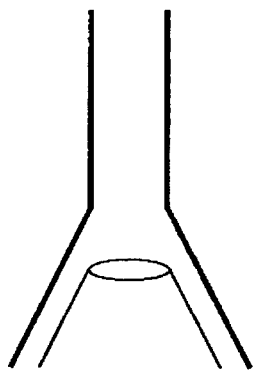
Figure 4:
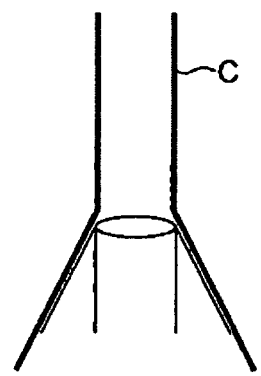
FIGS. 4 and 5 illustrate diagrammatically the way in which some previous airway devices may be positioned within a patient.
Figure 5:
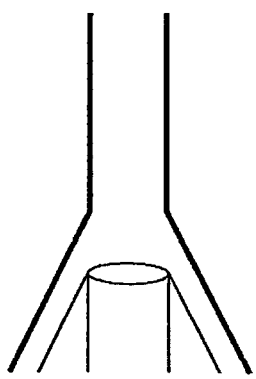
Figure 6:
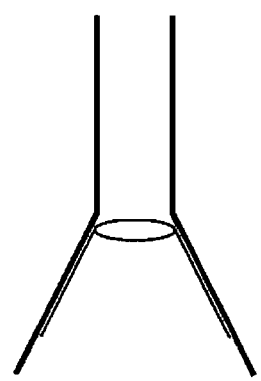
FIG. 6 illustrates diagrammatically the way in which an embodiment of the airway device of the present invention may be positioned within a patient.
Figure 7:
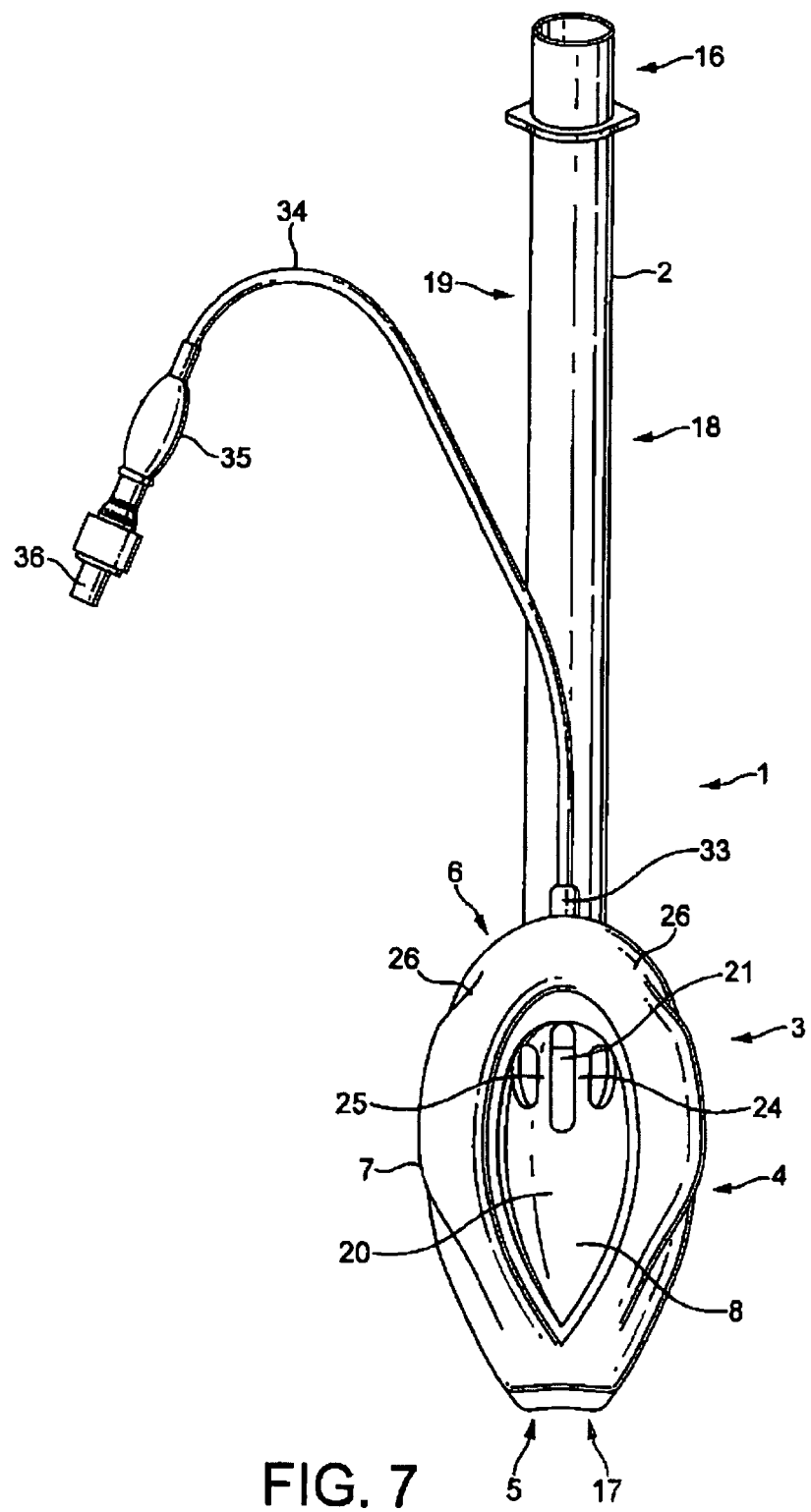
FIGS. 7 to 10 show ventral, dorsal, side and distal (front elevation) views of a first embodiment in a deflated condition.
Figure 8:
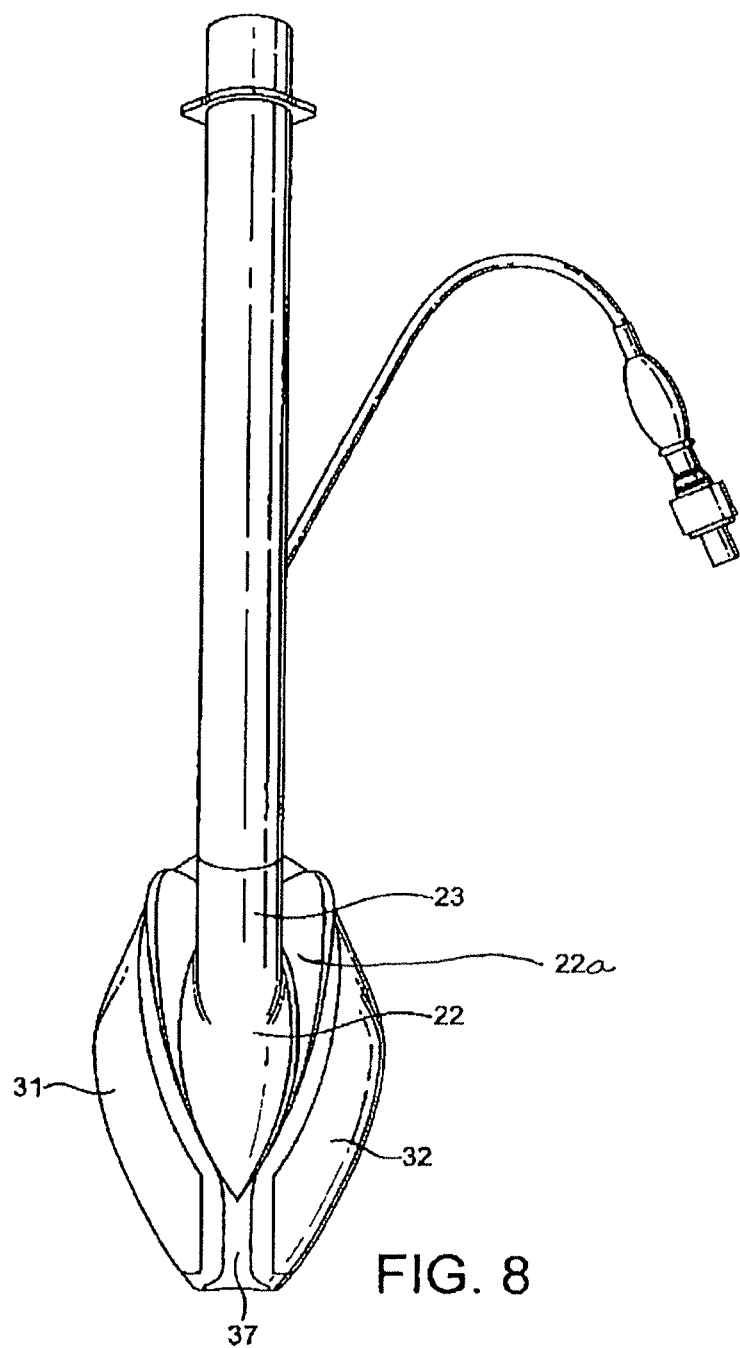
Figure 9:
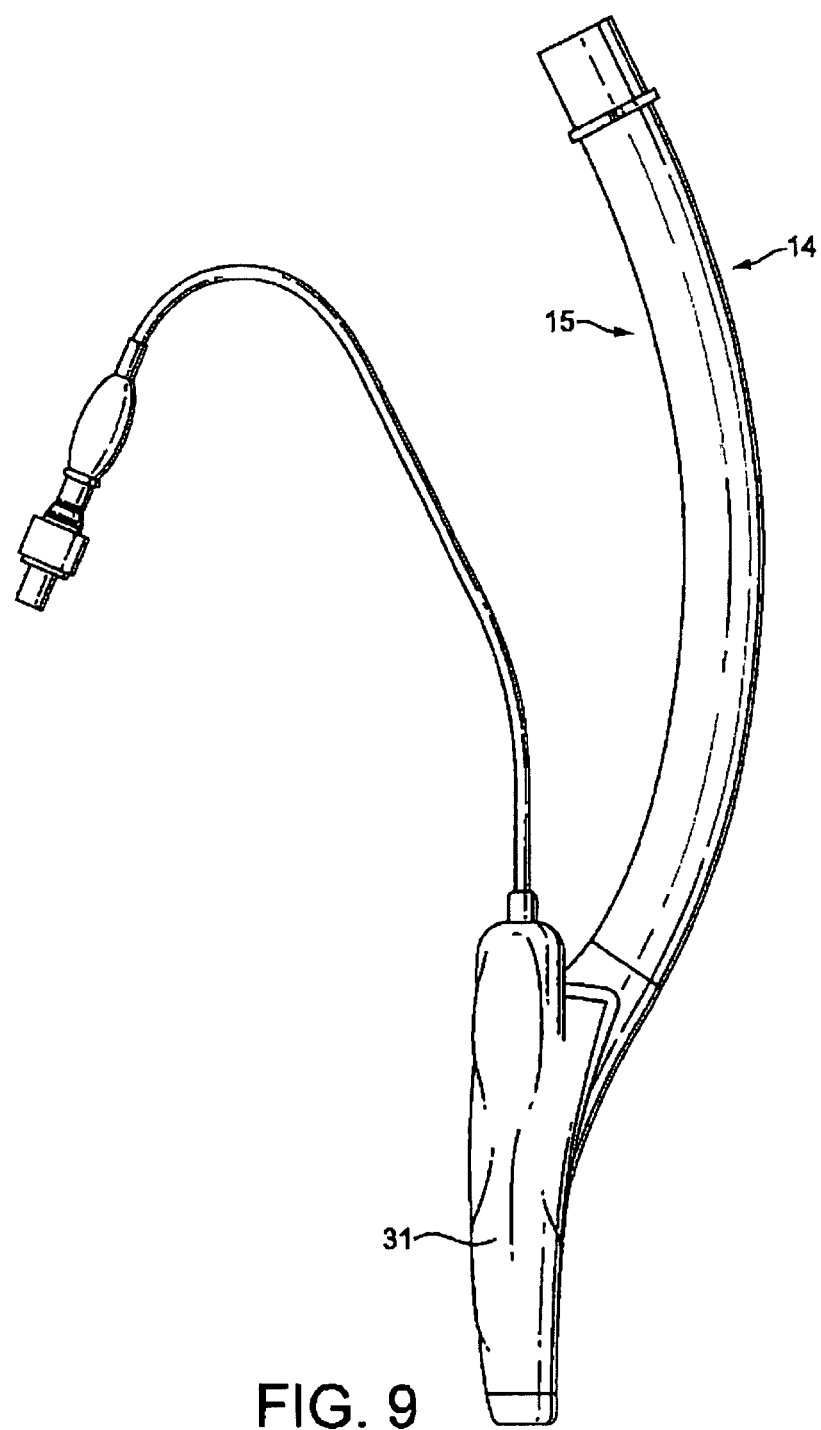
Figure 10:
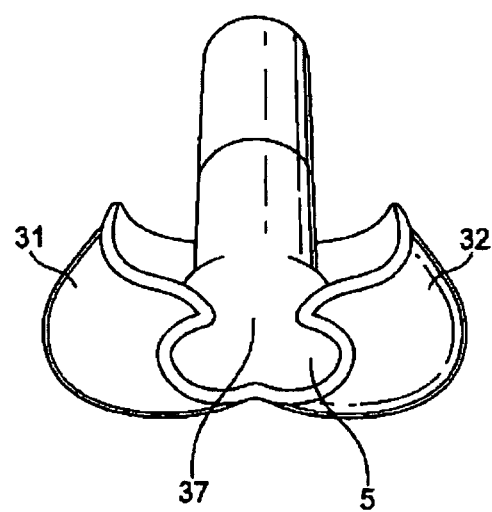
Figure 11:
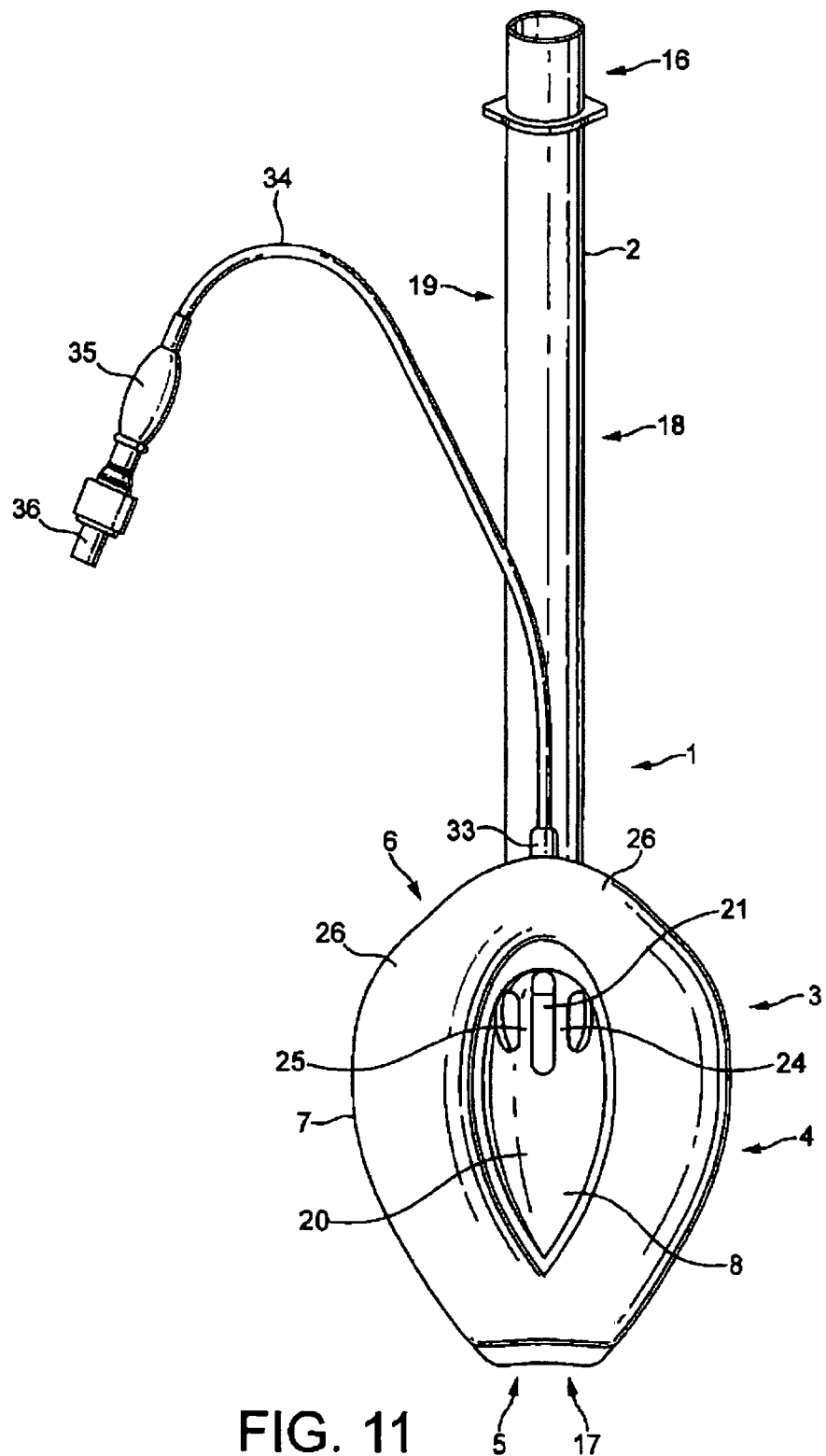
FIGS. 11 to 14 show ventral, dorsal, side and distal (front elevation) views of the first embodiment in an inflated condition.
Figure 12:
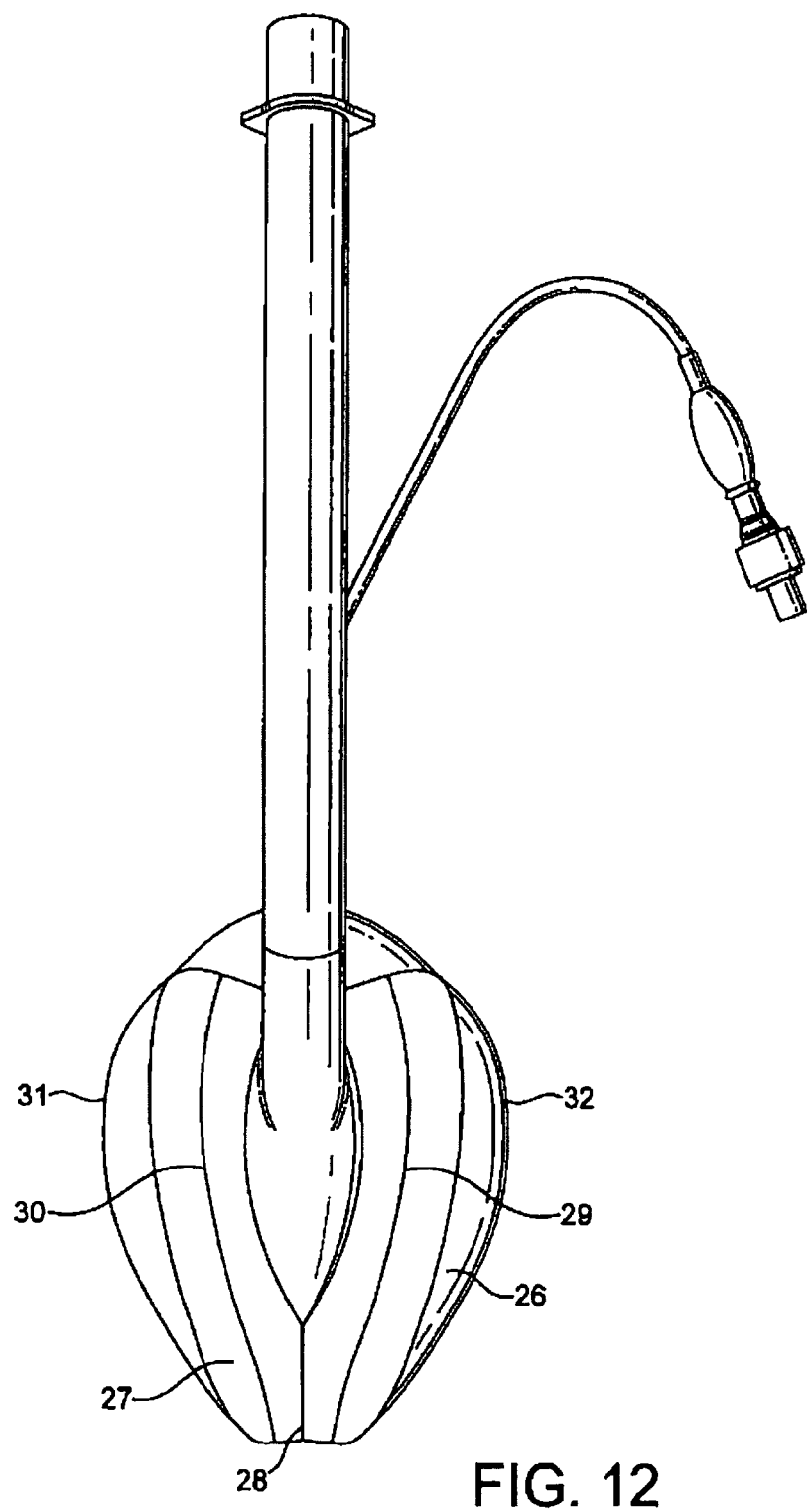
Figure 13:
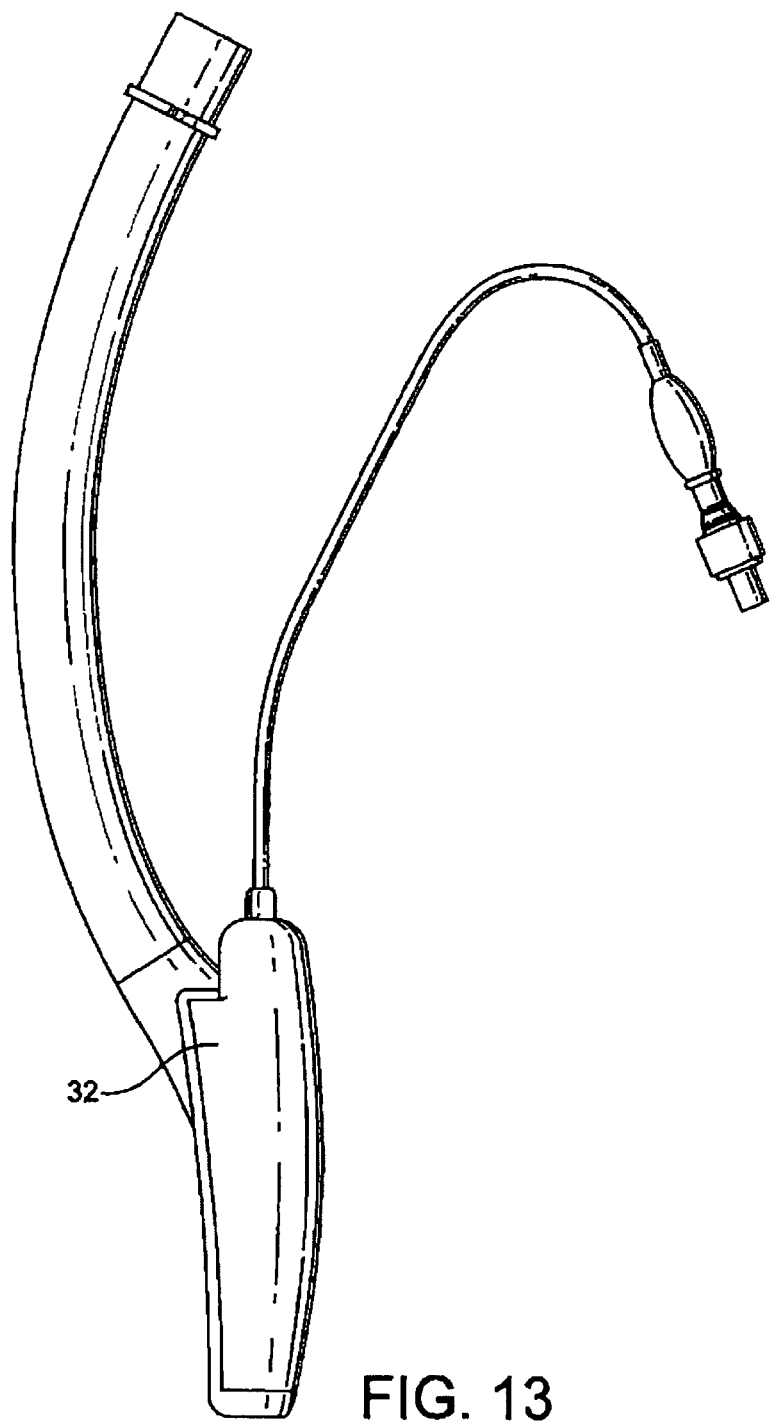

In the discussion of the following exemplary embodiments, like parts will generally be given the same reference numerals throughout the description.

FIGS. 7 to 14 show a first embodiment of an artificial airway device in the form of a laryngeal mask airway device 1 to facilitate lung ventilation of a patient, the device 1 comprising an airway tube 2 and a mask 3 provided at one end of the airway tube 2, the mask comprising a body 4 having a distal end 5 and a proximal end 6 and a peripheral inflatable cuff 7 which surrounds a hollow interior space or lumen of the mask, the mask 3 being attached to the airway tube 2 for gaseous communication between the tube 2 and the outlet 8. The mask of the present embodiment, and indeed of the further embodiments described hereinafter, is shaped to conform to and fit readily into the actual and potential space behind the larynx and to seal around the circumference of the laryngeal inlet. In the present embodiments, this seal is created without the laryngeal mask airway device penetrating into the interior of the larynx. The reference to actual and potential space will be understood to refer to the space normally available and that which can become available on flexure of the surrounding structures.

As can be seen from FIGS. 7 to 14, the device 1, in terms of overall appearance is somewhat similar to prior art devices, in that it consists of the basic parts which make up most if not all laryngeal mask airway devices, i.e. an airway tube 2 and mask 3 which includes a body part 4, and a cuff 7.

For the purposes of description it is appropriate to assign reference names to areas of the device 1 and accordingly with reference to the Figures, the device 1 has a dorsal side 14, a ventral side 15, a proximal end 16 {in the sense that this is the end nearest the user rather than the patient) a distal end 17 and right and left sides 18 and 19.

In the present embodiment, the airway tube 2 is provided as a flexible tube, although this does not have to be the case. For example, a curved airway tube could be employed, which may be more rigid and performed with an anatomically correct curvature.

The mask body 4 comprises two parts, namely an internal web 20 which defines the interior hollow or lumen of the body of the mask and which is provided with an aperture 21, and a semi-rigid back-plate 22 which conforms to the generally oval shape of the web 20 and is adhered to the rear (dorsal side) thereof. The back-plate 22 extends into a tubing portion 23, one end of which aligns with the aperture 21, and the other end of which receives the distal end of the airway tube 2, such that the airway tube 2 is in gaseous communication with the interior of the body of the mask 3 via the tubing portion 23 and the aperture 21. The airway tube 2 is connected in a gas-tight manner into the tubing portion 23 by any suitable means, such as by welding or adhesive, or by molding in one piece and in the present embodiment the axis of the airway tube is provided substantially in the same plane as the major axis of the inflatable cuff 7. As an optional feature the aperture 21 itself is provided with two flexible bars 24, 25 formed in the web 20, which bars 24, 25 stretch across the aperture and act to prevent the epiglottis of the patient from falling into the aperture 21 and hence interrupting the airway when the device 1 is in place.

The generally elliptical cuff 7 is formed from a soft, flexible sheet of silicone 26 and a generally "V"-shaped upper hinged portion 27. The flexible sheet 26 surrounds and is integrally formed with or otherwise hermetically secured to the periphery of the web 20 on the ventral side 15 of the mask 3 and is bonded in a gas-tight manner to the outer sides of the "V" of the upper hinged portion 27, the inner sides of the upper hinged portion being secured to the periphery of the back-plate 22. The apex of the "V" of the upper i.e. the distal end of the upper extends by a small amount, for example 2 mm, beyond the distal tip of the cuff.

In the present embodiment, the hinged nature of the upper portion 27 is provided by a central hinge 28 (see FIG. 12) provided by a scored line in the ventral surface of the upper 27 at the central portion of the mask, and two further lateral hinges 29, 30 in the form of further scored lines, each extending down the middle of a respective one of the arms of the "V", on the dorsal side of the upper 27. As will be appreciated, the central hinge 28 facilitates the lateral expansion of the mask 3, and the two further lateral hinges 29, 30 facilitate the lateral contraction of the mask 3.

Figure 15:
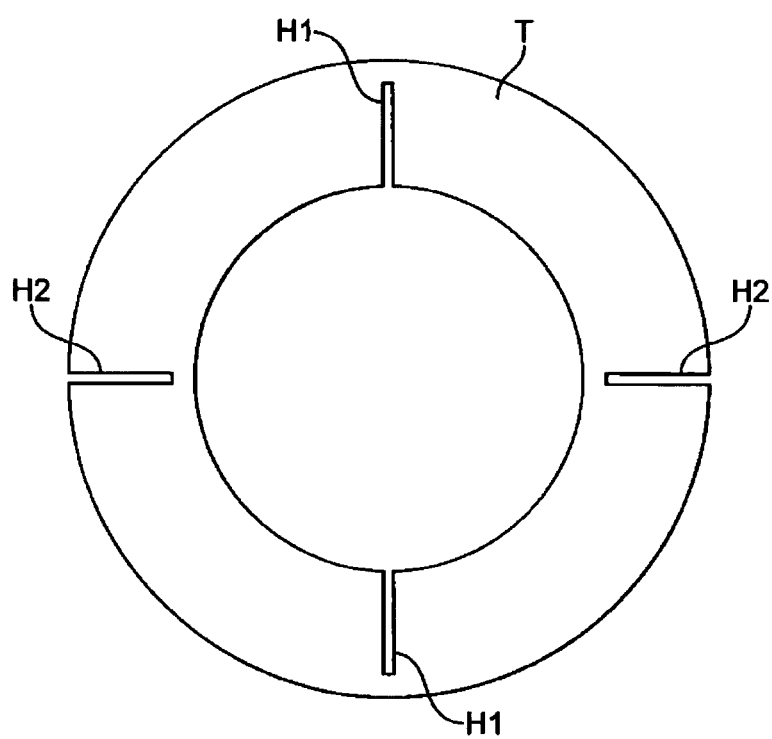
FIG. 15 illustrates a cross-sectional view of a tube.

In the present embodiment, the hinged upper portion 27 is formed from an extruded hinged tube T, having the cross section shown in FIG. 15. According to this tube (thickness of tube wall and hinge size exaggerated in FIG. 15 for clarity of illustration), two hinges H1 are provided on the inside of the tube and two hinges H2 are provided on the outside of the tube. To form the hinged upper 27, the tube is cut along its entire axial length along one side thereof, and for the majority of its length along the opposite side, to form the "'V" shaped hinged upper. This upper is then welded hermetically around the inner circumference of the back plate of the mask and along the edges of the flexible sheet of the cuff.

Figure 16:
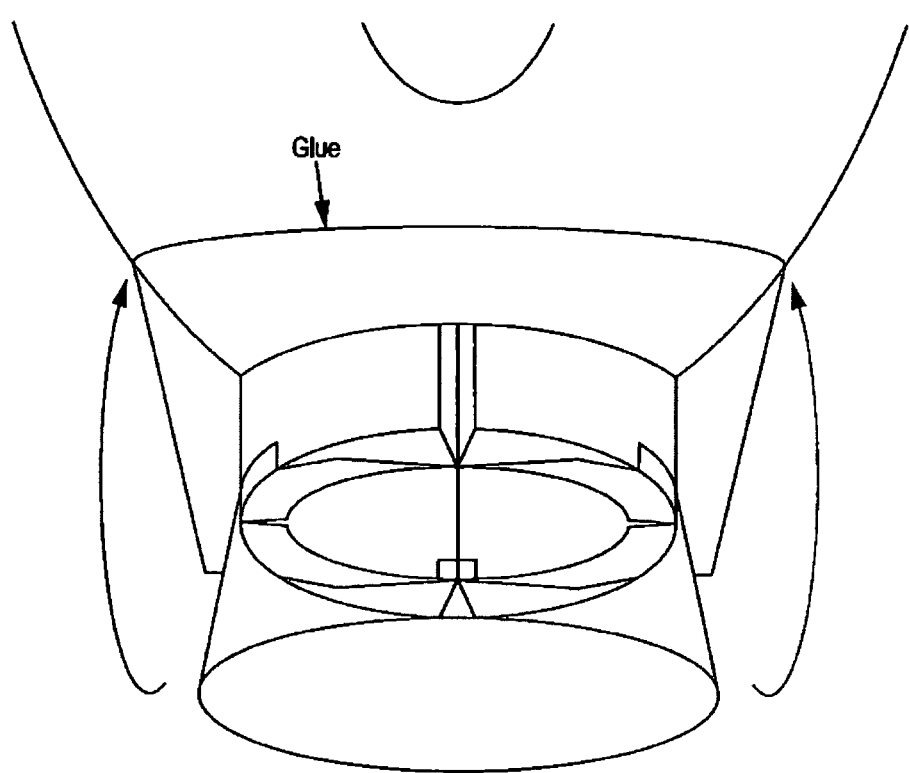
FIG. 16 illustrates a bonding mechanism.

FIG. 16 shows a mechanism employed according to the present exemplary embodiment to achieve a seal at the distal end of the cuff to enable it to be inflatable. According to this sealing method, the distal walls of the collapsible tube are cut so that they are "sharpened" at the leading edges, such that the inlet to the tube is generally frustoconical. This allows the thin flexible covering material of the cuff to be glued down to these thin edges, avoiding the glue getting into the crevices which are otherwise present where the walls of the collapsible tube are of full thickness.

It will be noted, however, that the present invention is not limited to the method of construction outlined above, nor indeed to an arrangement having an inflatable cuff.

The entire assembly of the present embodiment collapses when the mask is deflated, facilitating insertion into the normally closed space behind the larynx known as the hypopharynx, but achieves the shape shown in the Figures when inflated, due to the hinging mechanism of the tube halves which causes the tube to open out into its open locked position under the influence of intra-cuff pressure.

The cuff 7 thus effectively provides two inflatable wings, one on each lateral side of the mask 3, and which are in fluid communication at the proximal side of the cuff 7. The edges of each of the wings 31, 32 are chamfered to minimise the disruption to any tissue caused by the insertion and operation of the mask 3.

The cuff 7 is provided with a port 33 (see FIG. 11) at its proximal side, in which one end of a small-diameter inflation tube 34 is fitted in a gas-tight manner. The other end of the tube is provided with an inflation indicator bladder 35 and valve 36, for connection to a suitable pump, such as a medical syringe, for inflating and deflating the cuff 7.

In use, air is extracted from the cuff 7 via the valve 36, which results in the wings 31, 32 of the cuff 7 folding inwardly, facilitated by the lateral hinges 29, 30 of the upper hinged portion 27. The mask 3 is then in a condition which facilitates the insertion of the mask 3 into the pharynx of the patient. Preferably, the mask 3 is initially inserted with the interior of the mask 3 (i.e. ventral side 15) facing towards the rear wall of the pharynx, to facilitate the insertion of the mask 3 past the tongue of the patient. Thereafter, the mask 3 is gently rotated through 180 degrees to face forwards, and the mask 3 is further inserted until the distal end 5 of the mask 3 comes into contact with the upper oesophageal sphincter. This contact indicates to a user that the mask 3 is correctly positioned.

The cuff 7 is then inflated, thus sealing the artificial airway around the inlet to the larynx. Owing to the hinged nature of the upper portion 27, the wings 31, 32 tend to expand laterally of the mask 3, i.e. the wings unfold on inflation of the cuff. A space providing a drainage channel 22a is thus created in the pharynx between the interior walls of the pharynx and the outer (dorsal) side of the back plate 22 and the hinged upper portion 27. This space on the dorsal aspect of the mask substantially approximates that which would otherwise be bounded by the walls of the pharynx without the mask inserted, and hence by unfolding the wings of the mask, the anatomical space or volume in the pharynx which would be present without the mask inserted is recreated. Paradoxically, therefore, when the wings of the mask are unfolded (either by inflation or otherwise), the mask actually takes up less effective space within the pharyngeal passage as compared to prior art masks, as the mask creates a volume that resembles or approximates to the pharyngeal space which would otherwise be obstructed by the mask. That is, when in situ within the patient and with the wings unfolded, the mask substantially preserves the posterior anatomical hollow within the pharynx, and thus substantially reduces or eliminates altogether the resistance to the flow of matter (liquid, gas or solid) though the pharynx which would otherwise be created by the presence of a mask inserted in the pharynx. As such, most of the dorsal aspect of the mask according to the present embodiment provides a conduit having the approximate volume and shape of the lower pharynx, such volume being large enough to effect a significant rise in the pressure of any fluid emerging from the upper oesophageal sphincter while still providing an inflatable mask shape which maintains the required seal around the laryngeal orifice to ensure leak-free delivery of respiratory gases to the lungs using positive pressure mechanical ventilation.

Advantage is taken of the fact that the space of the lower pharynx is normally a closed space but may be expanded when fluids are forced through it or when an object such as a laryngeal mask is inserted into it. It is possible in consequence to provide an adequate volume of space in fluid communication with the oesophageal sphincter behind the anterior surface of the mask while still having sufficient area in the mask perimeter, which may for example be inflatable, to make the required sealing contact with the perilaryngeal tissues.

Put another way, the present embodiment features an inflatable cuff 7, which is movable under the action of inflation from a first (un-inflated) condition which facilitates the insertion of the mask 3, to a second (inflated) condition which thus re-establishes an approximation of the anatomy of the pharyngeal space present when the mask 3 is not in place.

The present invention is not however limited to an inflatable arrangement, and the wings of the mask 3 may be unfolded, and the mask movable from the first to the second condition, by any other suitable means. For example, a mask may be used which is inserted into place with an introducer-type spade device as is known in the art, which mask expands when the spade is removed to open up the pharyngeal anatomy of the patient to resemble the open anatomy of the patient when swallowing or retching.

Figure 14:
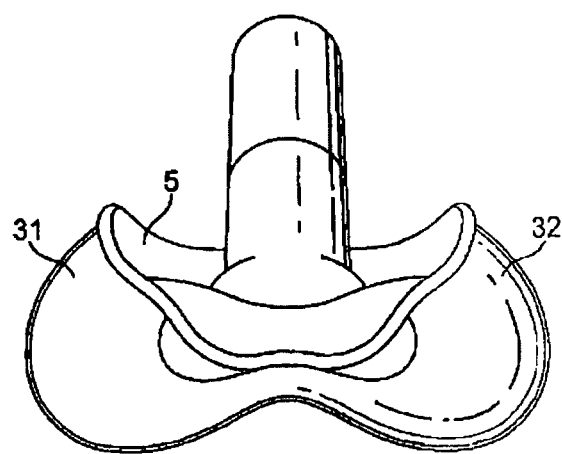

As will be appreciated, unlike prior art devices, the drainage channel of the present embodiment is not provided by a tube, but rather by the open back (dorsal side) of the mask itself and the walls of the pharynx. The inlet to this channel is defined by the generally "U" shaped guide way or conduit defined by the tips of the wings at the distal end of the mask when the wings of the mask are unfolded, as shown in FIG. 14.

The present embodiment thus provides a mask which is effectively "scooped out" at the back (dorsal) side to define the gastric drainage channel.

In the event of the patient regurgitating or vomiting, the gastric matter leaving the oesophageal sphincter is unimpeded by the presence of the mask 3, which substantially re-establishes the normal amount of space available for drainage through the pharynx when the mask 3 is not inserted. As a result, the mask 3 does not impede the flow of gastric contents but on the contrary allows such contents to flow freely behind it, thus substantially minimising the danger of the mask becoming dislodged from its position by the pressure of such flow. In addition, the artificial airway provided by the mask and airway tube remains uninterrupted and the seal around the inlet to the larynx is not broken, thus making very unlikely the possibility of gastric matter being aspirated into the lungs of the patient.

Furthermore, and particularly during vomiting conditions, the mask 3 is in fact drawn more closely into its operating position in the patient's pharynx, as a result of a venturi being created by the drainage channel provided by the mask. Specifically, the gastric matter being vomited by the patient may arrive at the constriction or sphincter situated at the upper end of the oesophagus at pressures approximating 200 cm H20 high pressure. The gastric matter passes through this constricted portion at a higher velocity than it does through the oesophagus, and in accordance with the Bernoulli Principle, this obligatory increase in velocity results in a drop in pressure in the gastric matter locally. On leaving the upper oesophageal sphincter, the gastric matter enters the flow channel defined by the mask 3 and the pharynx which is of a larger cross-sectional area, in the plane to which the velocity vector of the flow is normal or perpendicular, than the upper oesophageal sphincter under vomiting. As a result, the velocity of the gastric matter passing through this larger flow channel decreases, and accordingly the pressure of this gastric matter increases, to greater than that in the oesophageal sphincter. The pressure differential between the gastric matter in the upper oesophageal sphincter and in the flow channel defined by the mask 3 and pharynx results in the mask 3 being actively forced further into engagement with the oesophageal sphincter, thus holding the mask 3 yet more securely in its operational position than when vomiting is not occurring.

A further feature of the present embodiment is that insertion of the mask 3 into place is facilitated where a gastroscope or similar is already inserted into the pharynx of the patient. Unlike prior art devices in which the drainage channel is provided by a tube, the drainage channel in the present embodiment is defined by the open back (dorsal side) of the mask. The entrance to this channel is defined by the notch or trench 37 (see FIG. 10) created between the tips of the wings 31, 32, which can receive the cable of an inserted gastroscope or similar, facilitating the guiding of the mask 3 into the pharynx of the patient by sliding the mask along the cable as a rail.

Conversely, where the mask 3 is already in place, the later insertion of a gastroscope or similar is facilitated by being guided into place by the channel defined by the dorsal side of the mask 3 and the pharynx, and in particular by the trench created between the opposed wings of the mask. Further, as the present embodiment acts to re-establish the pharyngeal space normally available for drainage, the insertion of a gastroscope or similar into the pharynx is not impeded by the presence in the pharynx of the mask 3 itself.

A further advantage provided by the present embodiment is that the hinged upper permits the cuff to be inverted for cleaning of the cuff, the upper and the back plate by forcing the wings of the cuff apart. This is particularly advantageous where the embodiment is intended as a re-useable product.

As will be appreciated by the skilled person, the present invention is not limited to the types of construction or material identified in connection with the present or succeeding embodiments. For example, the airway tube 2 and mask 4 may all be formed from PVC plastics material, especially where a single-use, disposable device is intended, different parts may be secured by different means or be integrally formed from a single piece of material, as appropriate.

Figure 17:
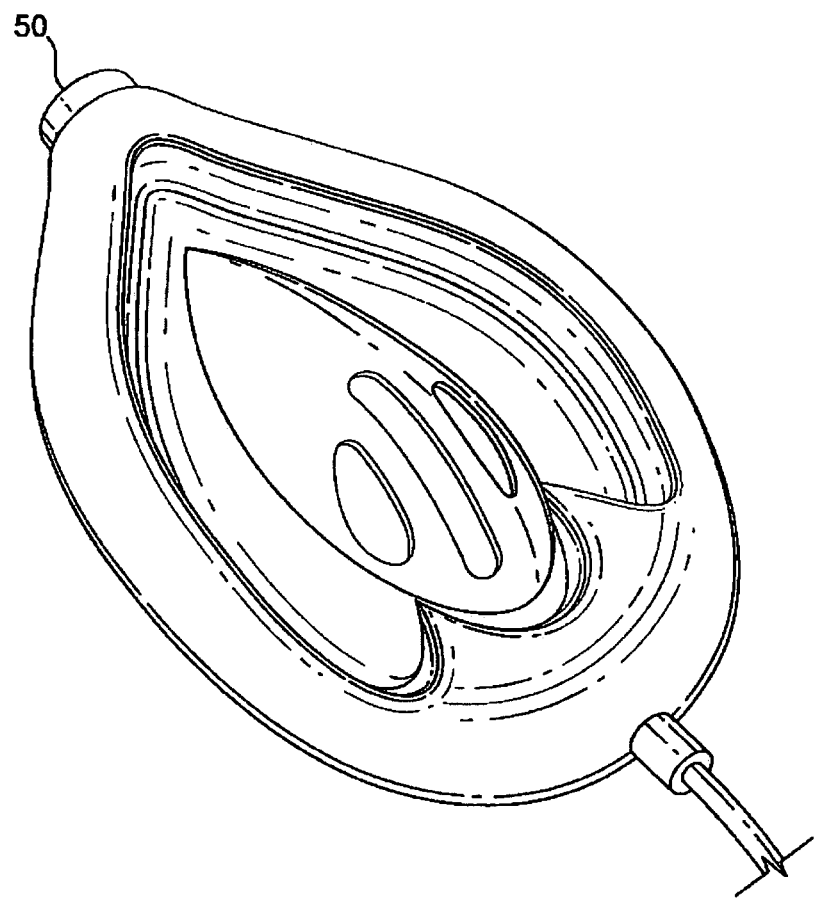
FIG. 17 shows a variation of the first embodiment in an inflated state.

A variation of the first embodiment, itself also an embodiment of the present invention, is shown in FIG. 17, in a partially constructed condition before the back plate and airway tube are added to complete the laryngeal mask device. This variation differs from the first embodiment in that the apex of the "V" of the hinged upper portion is provided as a tubular portion which defines an inlet 50 of circular cross-section between 10 and 15 mm in diameter at the distal open end of the mask.

As such, most of the interior volume of the mask according to the present embodiment provides a conduit having the approximate volume and shape of the lower pharynx, such volume being large enough to effect a significant rise in the pressure of any fluid emerging from the upper oesophageal sphincter while still providing an inflatable mask shape which maintains the required seal around the laryngeal orifice to ensure leak-free delivery of respiratory gases to the lungs using positive pressure mechanical ventilation.

Advantage is taken of the fact that the space of the lower pharynx is normally a closed space but may be expanded when fluids are forced through it or when an object such as a laryngeal mask is inserted into it. It is possible in consequence to provide an adequate volume of space in fluid communication with the oesophageal sphincter behind the anterior surface of the mask while still having sufficient area in the mask perimeter, which may for example be inflatable, to make the required sealing contact with the perilaryngeal tissues.

As in the first embodiment, the hinged upper 27 is formed from a hinged tube split as shown and welded hermetically around the inner circumference of said mask, forming a single tube of orifice between 10 and 15 mm ID at the distal open end of said mask. The entire assembly collapses when the mask is deflated, facilitating insertion into the normally closed space behind the larynx known as the hypopharynx, but achieves the shape shown in FIG. 17 when inflated, due to the hinging mechanism of the tube halves which causes the tube to open out into its open locked position under the influence of intra-cuff pressure.

Figure 18:
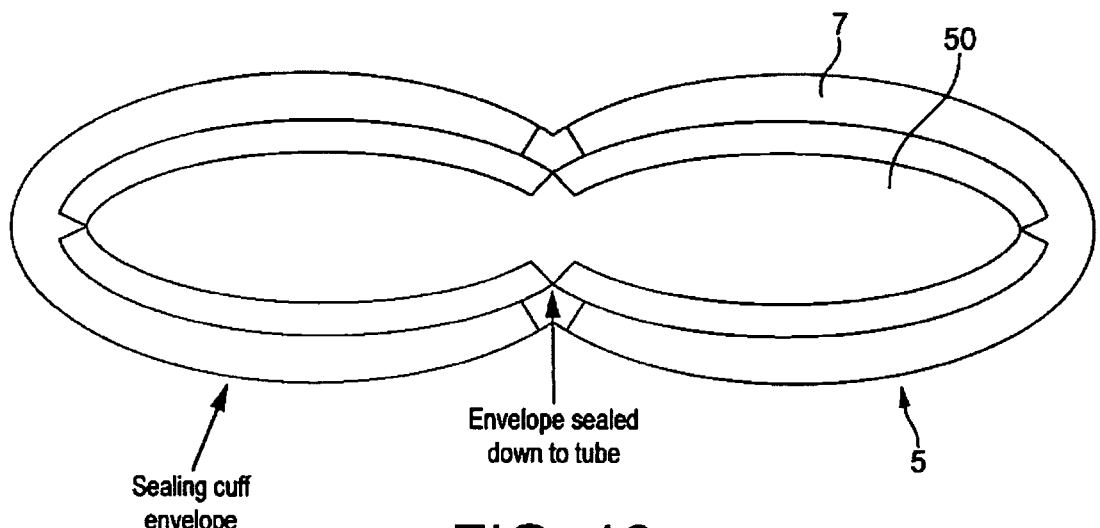
FIGS. 18 and 19 are cross-sections through the gastric discharge inlet of the embodiment of FIG. 17, showing the condition of the inlet when the cuff is deflated and inflated, respectively.
Figure 19:
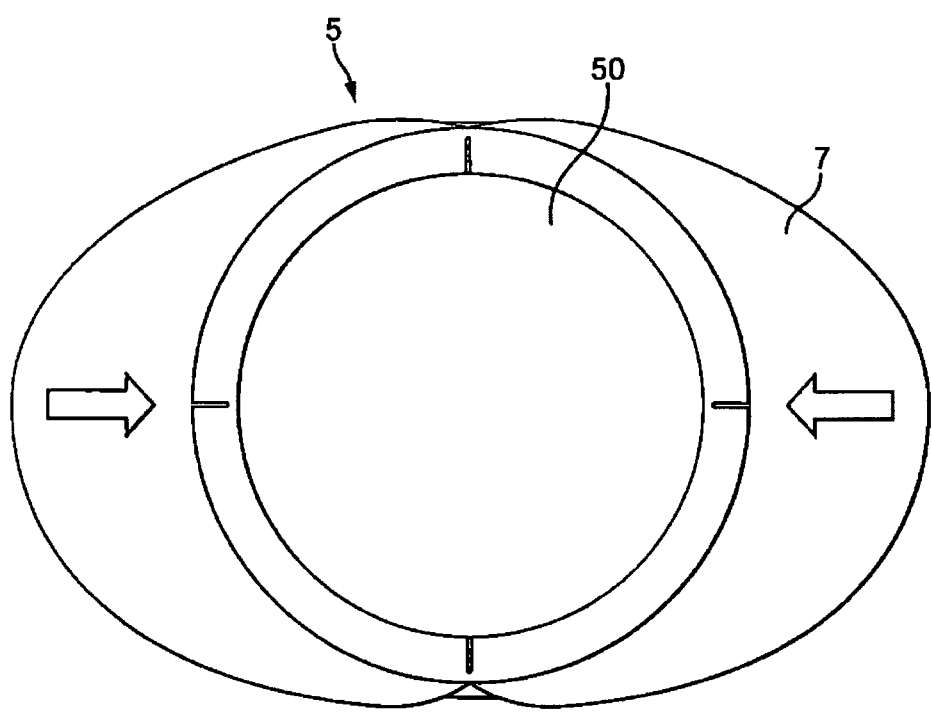

The collapse of the mask when the cuff is deflated is in particular facilitated by the un-cut length of the hinged tube which defines the inlet to the drainage channel, as this tube collapses as shown in FIG. 18 when the cuff is deflated. This permits a large-diameter gastric tube to be provided once the mask is in place within the patient and the cuff inflated, as illustrated by FIG. 18, but at the same time facilitates insertion of the mask into the patient, as on insertion the mask is intended to be in an uninflated state, wherein the inlet of the gastric drainage tube effectively closes up.

Figure 20:
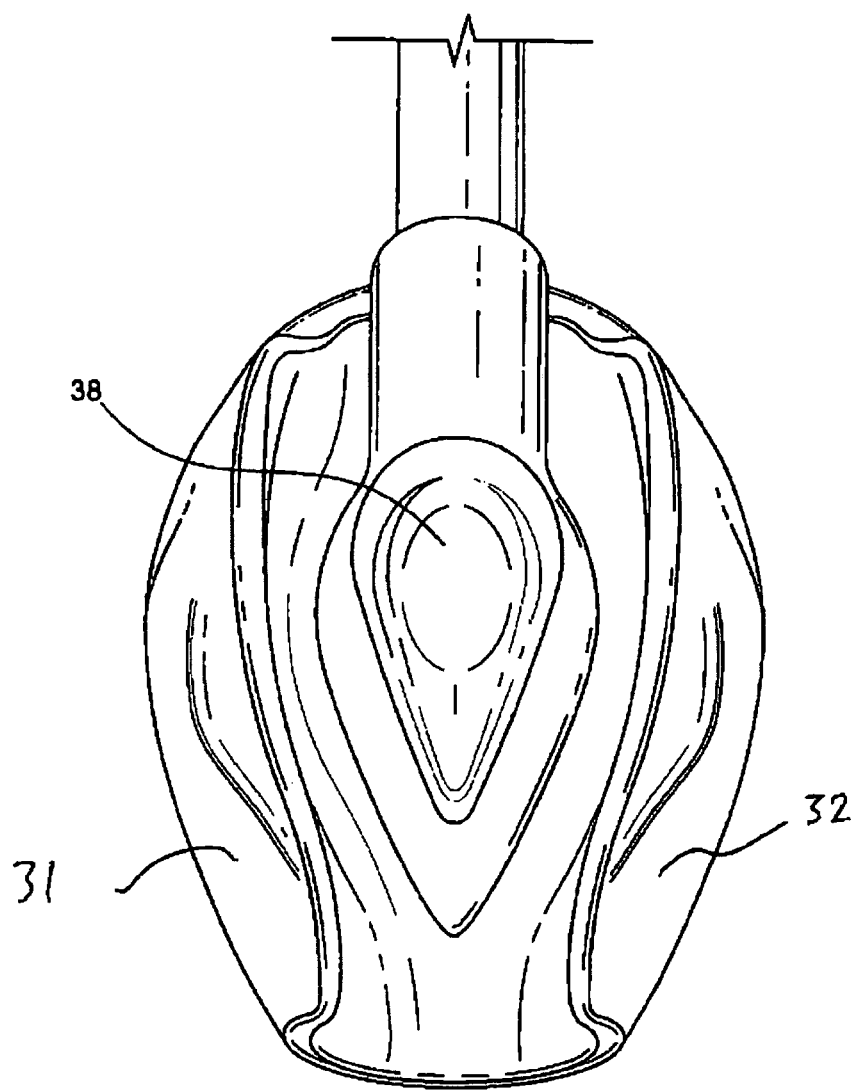
FIGS. 20 and 21 shows a views of the mask according to a second embodiment.
Figure 21:
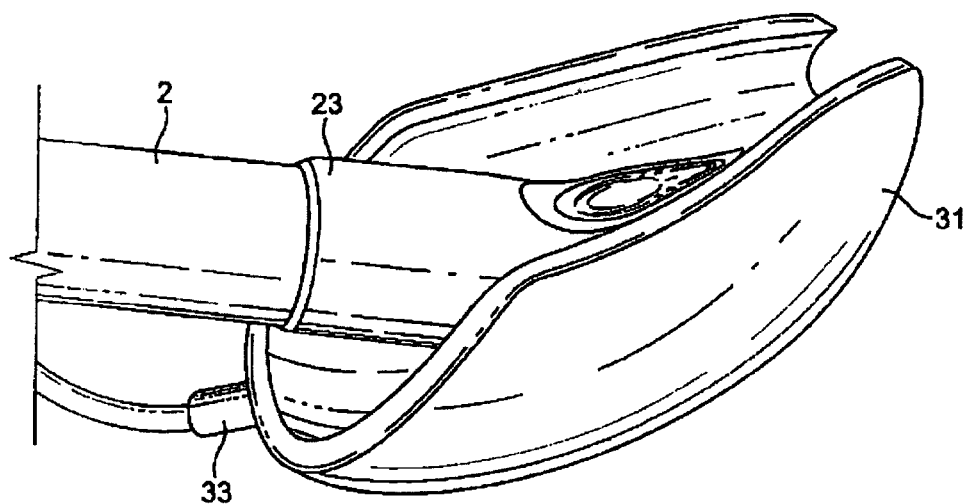
Figure 22:
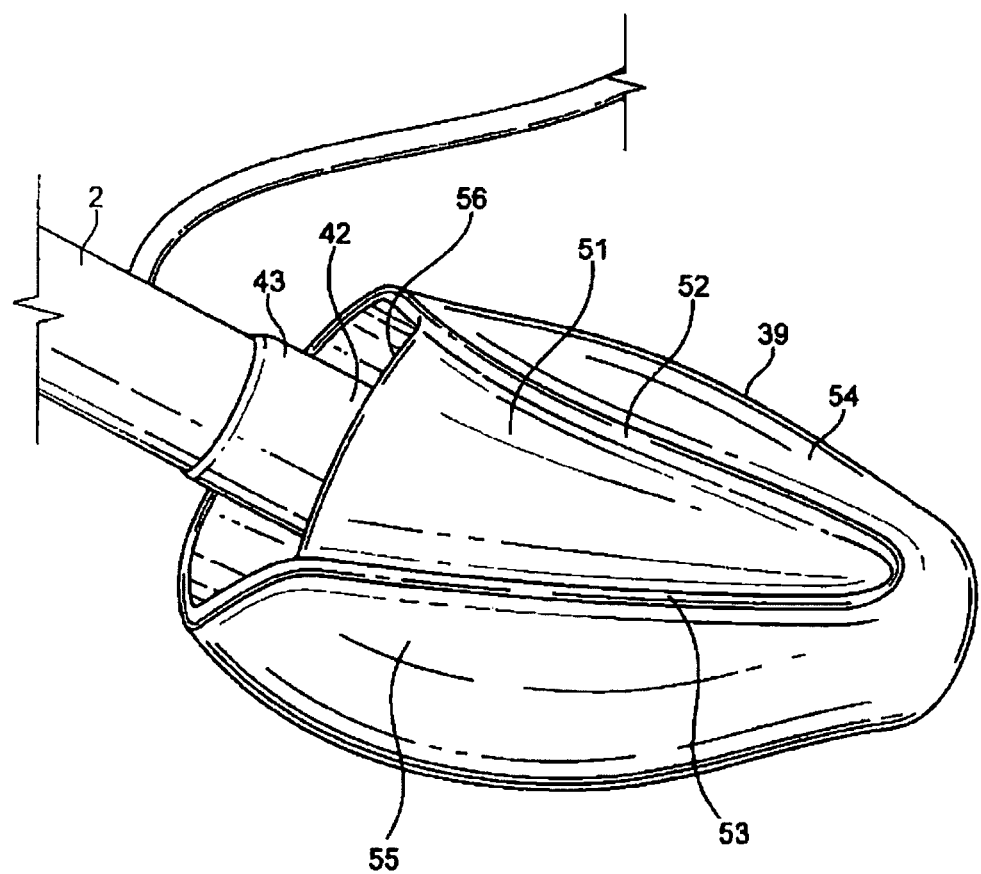
FIGS. 22 to 27 show respectively a left-side perspective, rear (posterior) perspective, front (distal end) elevation, front side perspective, underside and rear perspective views of a third embodiment in an inflated. condition, respectively.
Figure 23:
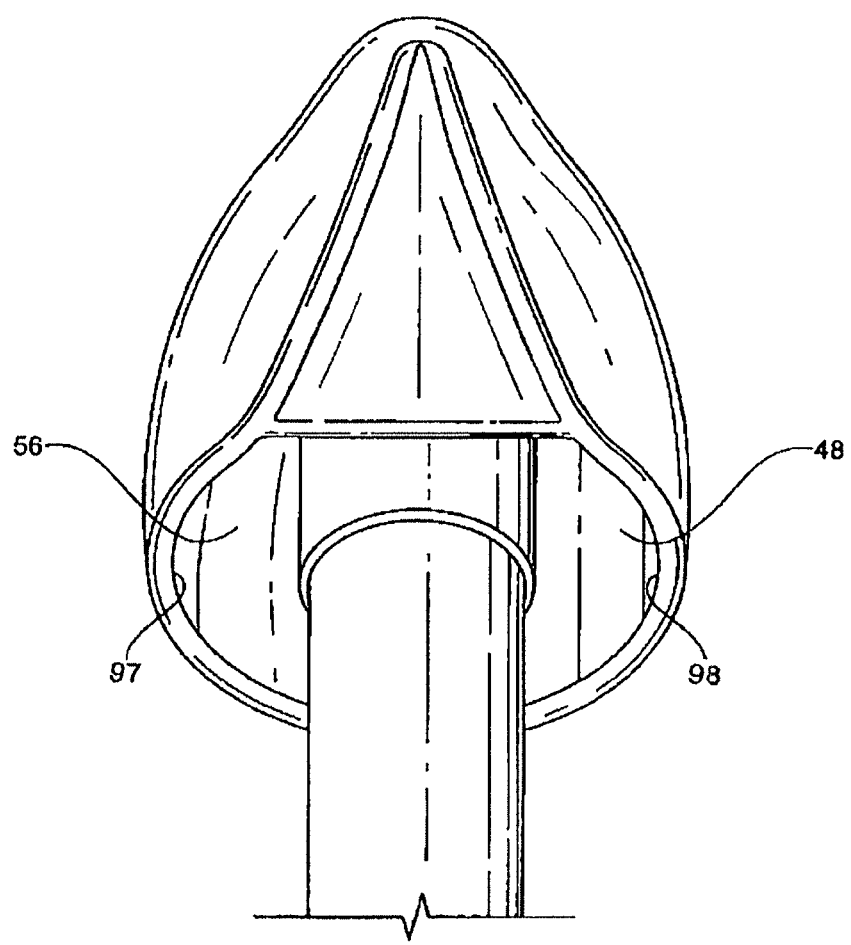
Figure 24:
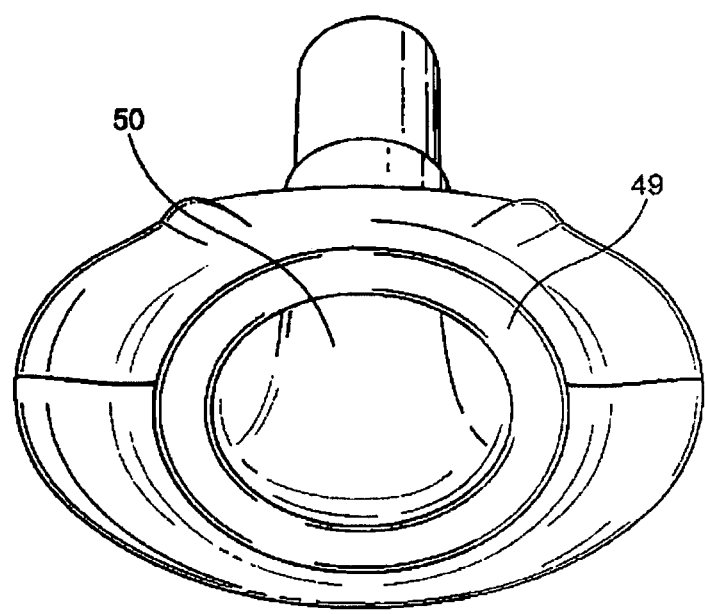
Figure 25:
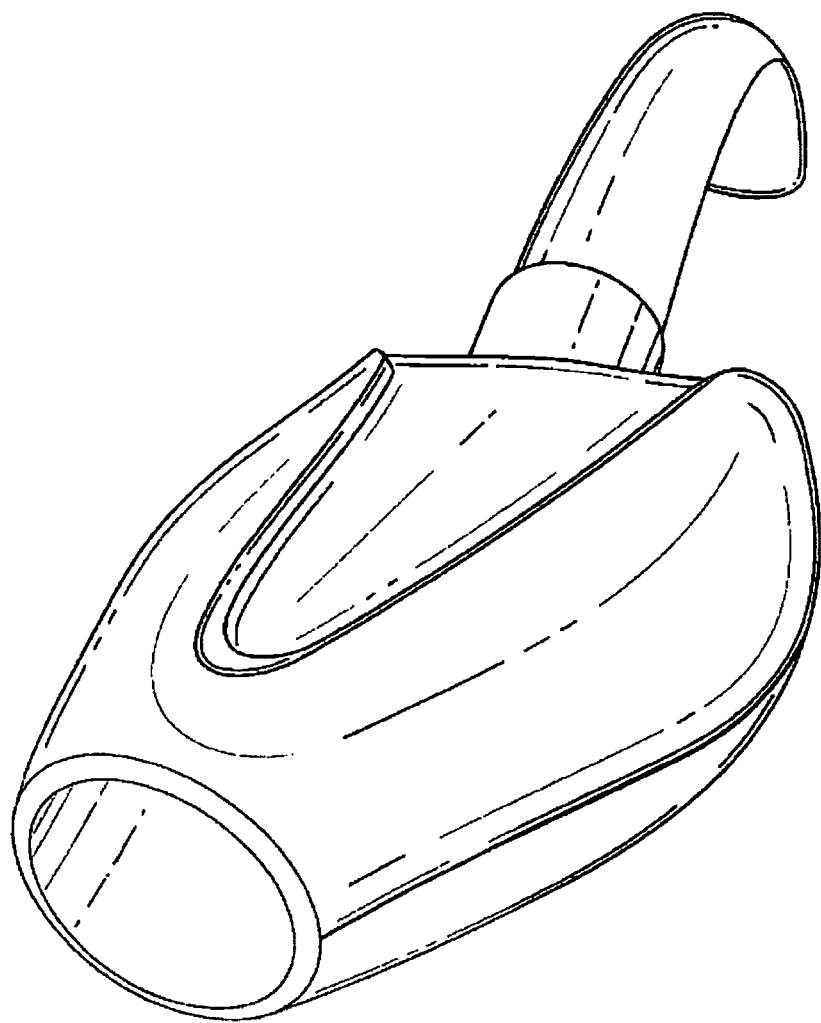
Figure 26:
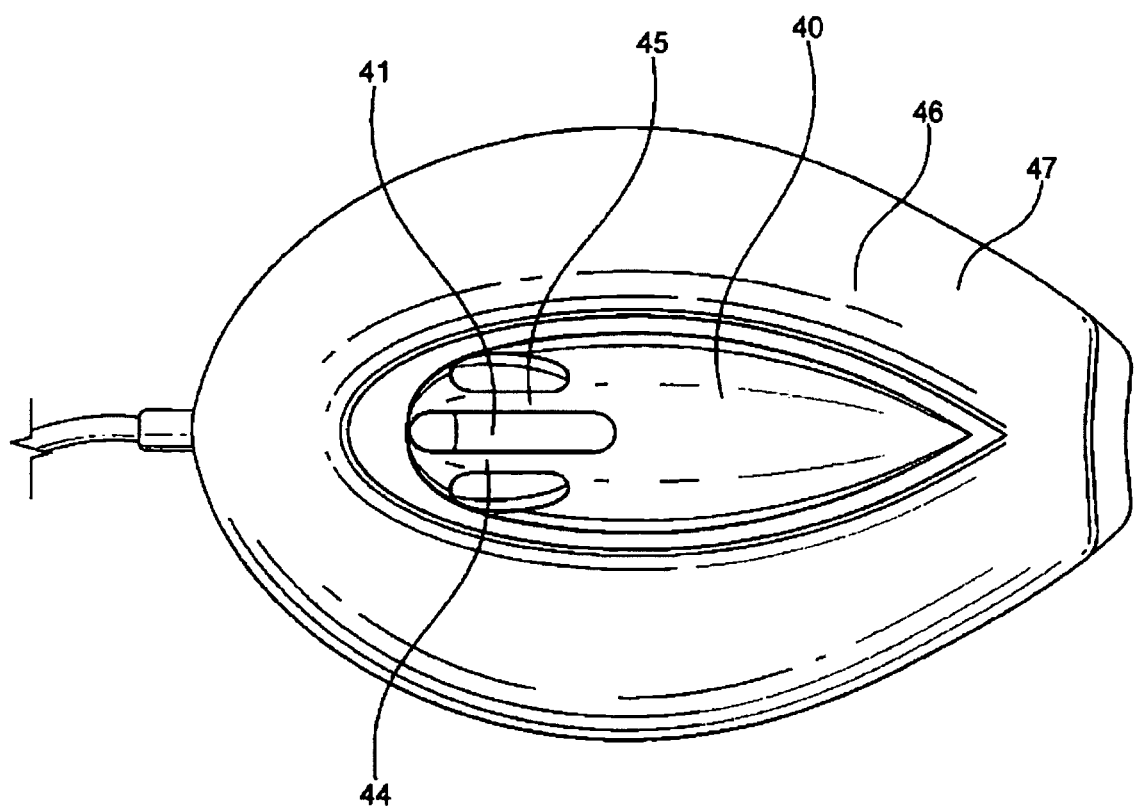
Figure 27:
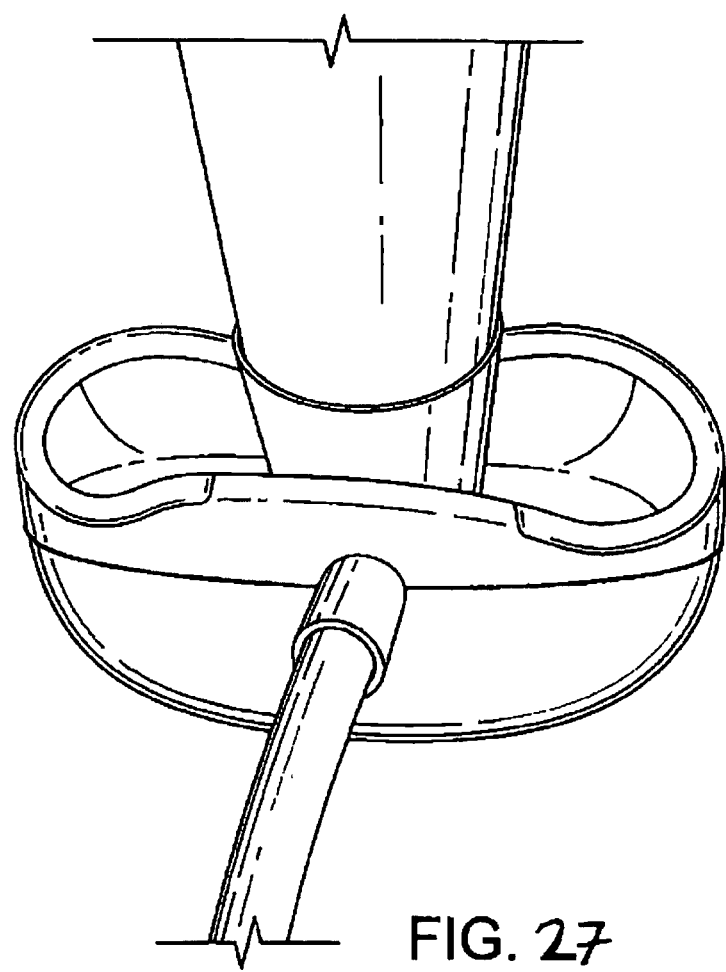

A second embodiment shown in FIGS. 20 to 21 differs from the first embodiment only in that a portion 38 of the tubed section of the back-plate 22 is scooped away to facilitate the insertion of the device 1 into a patient.

According to the third embodiment shown in FIGS. 22 to 27, the laryngeal mask airway device 1 again comprises an airway tube 2 with a mask 39 provided at the distal end thereof.

Similar to the first embodiment, the mask 39 comprises an internal web 40 which defines the interior of the body of the mask 39 and which is provided with an aperture 41, and a semi-rigid back-plate 42 which conforms to the generally oval shape of the web 40 and is adhered or otherwise attached to the rear (dorsal side) thereof. The back-plate 42 extends into a tubing portion 43, one end of which aligns with the aperture 41, and the other end of which receives the distal end of the airway tube 2, such that the airway tube 2 is in gaseous communication with the interior of the body of the mask 39 via the tubing portion 43 and the aperture 41. The airway tube 2 is connected in an gas-tight manner into the tubing portion 43 by any suitable means, such as by welding or adhesive. The aperture 41 itself is provided with two flexible bars 44, 45 formed in the web 40, which bars 44, 45 stretch across the aperture 41 and act to prevent the epiglottis of the patient from falling into the aperture 41 and hence interrupting the airway when the mask 39 is in place.

According to the third embodiment, the cuff 46 is again formed from a flexible sheet 47 of silicone which is integrally formed with or otherwise hermetically secured to the periphery of the web 40, e.g. by adhesive bonding or welding, on the ventral side of the mask. Similarly, the inner edges of a generally "V"-shaped upper 48 surround the back plate 42, but in this embodiment, as in the first variation of the first embodiment, the apex of the "V" is provided as a hinged tubular portion which defines an inlet 50 of circular cross-section at the distal end of the mask 49. As will be appreciated, as in the variation of the first embodiment this facilitates the collapse of the inlet and hence the insertion of the device into a patient on deflation of the cuff, whilst still providing a large diameter drainage channel (e.g. 10 mm diameter) once the cuff is inflated.

The flexible sheet 47 surrounds this inlet 50 and is joined to the outer sides of the "V" of the upper 48. Further, a flexible and somewhat elastic triangular sheet 51 is attached between the opposed sides 52, 53 of the flexible sheet of the cuff where they meet the upper 48. In the present embodiment, the triangular sheet 51 is transparent. Similar to the first embodiment, inflatable wings 54, 55 are thus created on respective lateral sides of the device, which wings are joined along their edges by the triangular elastic sheet.

A generally frustro-conical channel is thus created within the body of the mask, having a generally circular inlet 50 at the distal end of the mask and an outlet region 56 at the posterior end of the mask, which outlet region 56 has a greater cross-sectional area than the inlet 50 in the plane perpendicular to the longitudinal axis of the mask. As such, most of the interior volume of the mask provides a conduit having the approximate volume and shape of the lower pharynx, such volume being large enough to effect a significant rise in the pressure of any fluid emerging from the upper oesophageal sphincter while still providing an inflatable mask shape which maintains the required seal around the laryngeal orifice to ensure leak-free delivery of respiratory gases to the lungs using positive pressure mechanical ventilation.

Advantage is taken of the fact that the space of the lower pharynx is normally a closed space but may be expanded when fluids are forced through it or when an object such as a laryngeal mask is inserted into it. It is possible in consequence to provide an adequate volume of space in fluid communication with the oesophageal sphincter behind the anterior surface of the mask while still having sufficient inflatable area in the mask perimeter to make the required sealing contact with the perilaryngeal tissues.

Similar to the first embodiment, the device of the third embodiment is placed into an insertion condition by deflating the cuff 46. The reverse hinges 97, 98 provided as scored portions on the dorsal side of the upper portion 48 again facilitate the inward folding of the wings of the mask so as to adopt as small a size as possible.

After insertion, the cuff 46 of the mask 39 is then inflated, which in particular causes the wings 54, 55 of the mask to separate. The separation of the wings is not as great as in the first embodiment, however, as a result of the edges of the wings being linked by the triangular sheet 51. This prevents undue pressure from being placed on the lateral walls of the pharynx by the expanding wings 54, 55, and in particular seeks to avoid undue stretching of the hyoid bones and any possible pressure on the hypoglossal nerve. Also, as the edges of the wings are joined by the triangular sheet to form a generally flush dorsal surface to the mask, the small potential of trauma to the tissue of the pharynx caused by the edges of the wings contacting the walls of the pharynx on insertion of the mask is averted. The flexibility and stretchability of the triangular sheet 51 does permit opening of the wings 54, 55, however.

As will be appreciated, according to this embodiment gastric drainage is not provided by a tube which extends out of the mouth of the patient, as in prior art devices, but rather by an orifice at the distal end of the mask which defines an inlet to a drainage channel within the body of the mask. Thereafter, drainage of gastric matter is simply provided by the normal anatomy of the patient i.e. the pharynx.

Similar effects and advantages as in the first embodiment are achieved, and any gastric discharge is guided away from the upper oesophageal sphincter by the internal channel created within the mask body.

Figure 28:
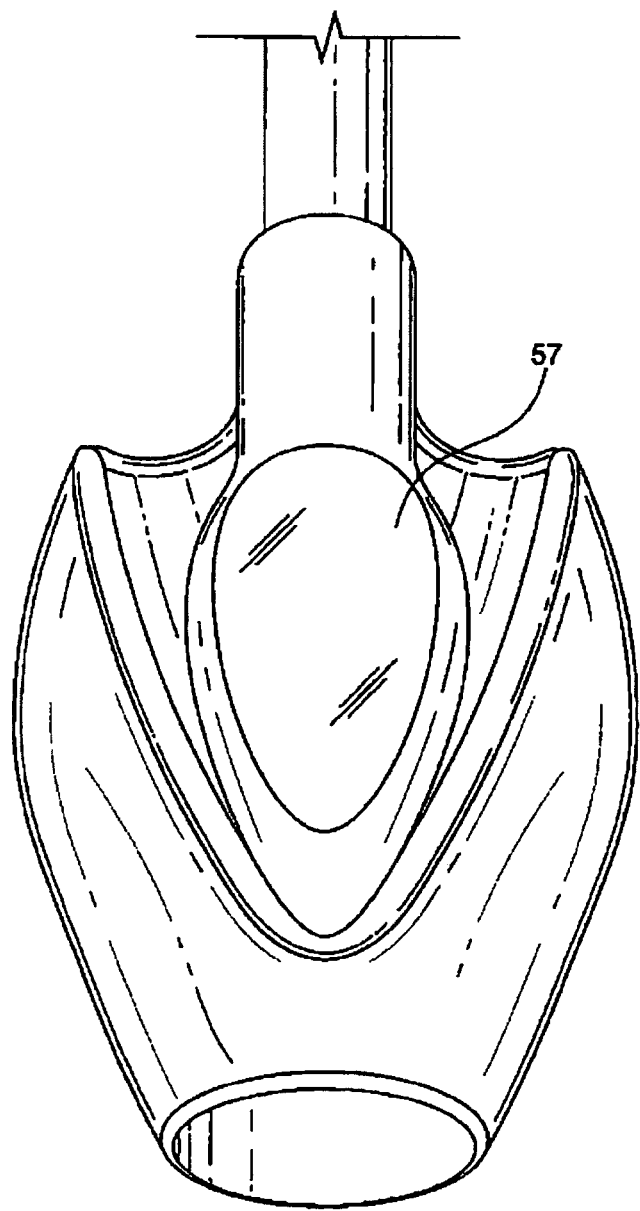
FIGS. 28 to 29 show a front perspective and underside plan, views of a fourth embodiment in an inflated condition.
Figure 29:
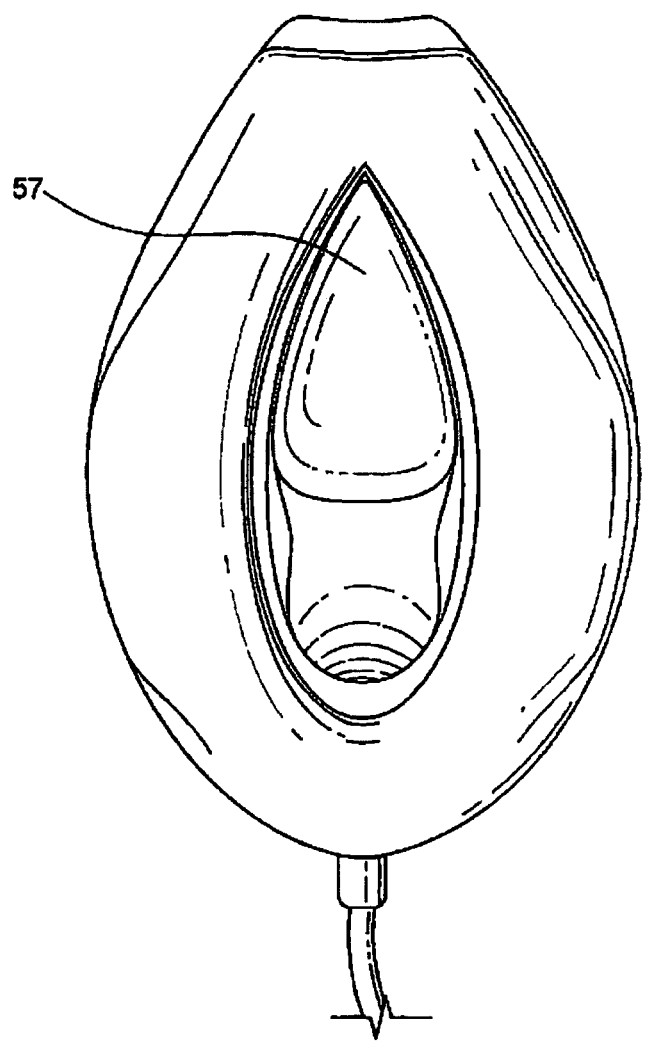

A fourth embodiment shown in FIGS. 28 to 29 differs from the third embodiment in that a generally triangular region of the back-plate is removed and replaced with a transparent window 57, which is bonded into the back-plate in an air tight manner such that the effectiveness of gas delivery by the fourth embodiment is not effected. Further, the internal web is omitted. As a result of these changes, the inlet to the larynx may be viewed through the mask by use of a suitable viewing device e.g. an endoscope, to confirm the correct positioning of the mask and adequacy of space created behind the mask when inflated.

A further difference between the fourth and third embodiments is that the triangular sheet is omitted, which permits greater separation of the wings of the mask upon inflation of the cuff.

As will be appreciated by the skilled person, similar effects and advantages as in the third embodiment are achieved by the present embodiment.

Figure 30:
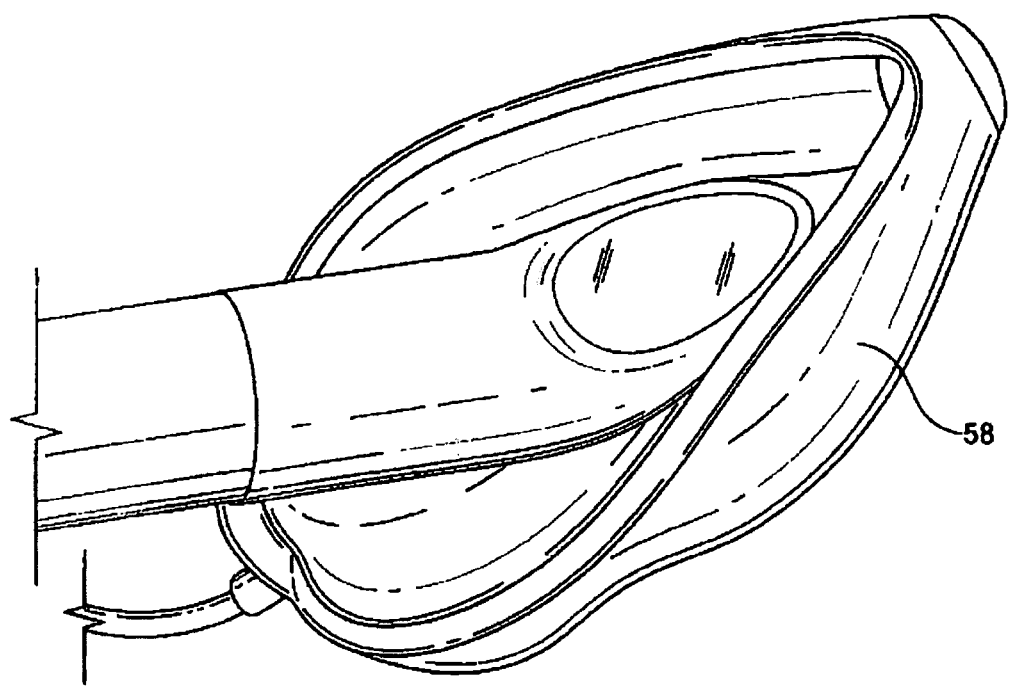
FIGS. 30 to 32 show rear side perspective, underside plan and side elevation views of a fifth embodiment in an inflated condition.
Figure 31:
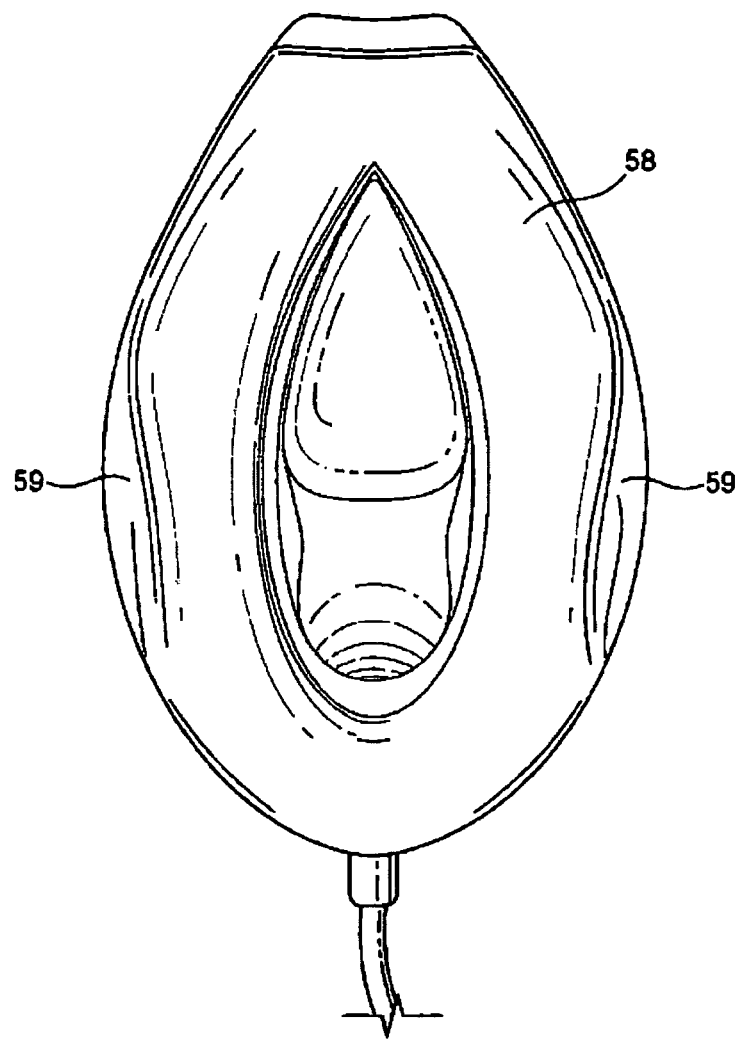
Figure 32:
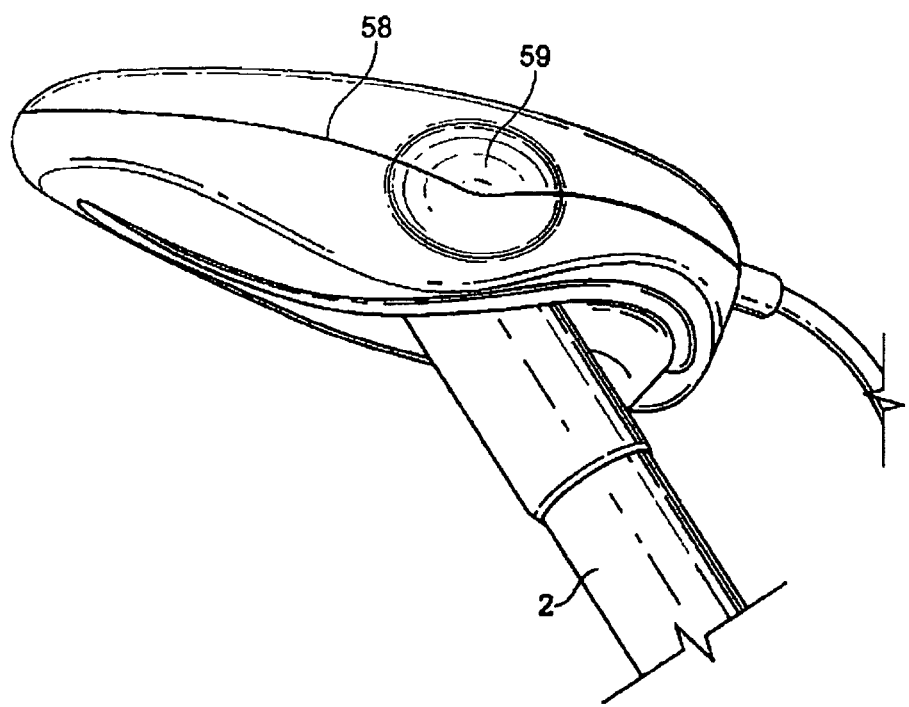

A fifth embodiment is shown in FIGS. 30 to 32. The fifth embodiment differs from the fourth embodiment in that the cuff 58 is internally bonded to the back plate in two lateral positions, thus forming dimples 59 in the surface of the cuff. These dimples 59 seek to prevent the possibility of stretching of the hyoid bones and consequential pressure on the hypoglossal nerve on inflation of the mask, as in the third embodiment. By avoiding the sheet of the third embodiment, however, the mask of the present embodiment is easier to clean, facilitating its employment as a re-usable device.

As will be appreciated by the skilled person, similar effects and advantages as in the fourth embodiment are achieved by the present embodiment.

Figure 33:
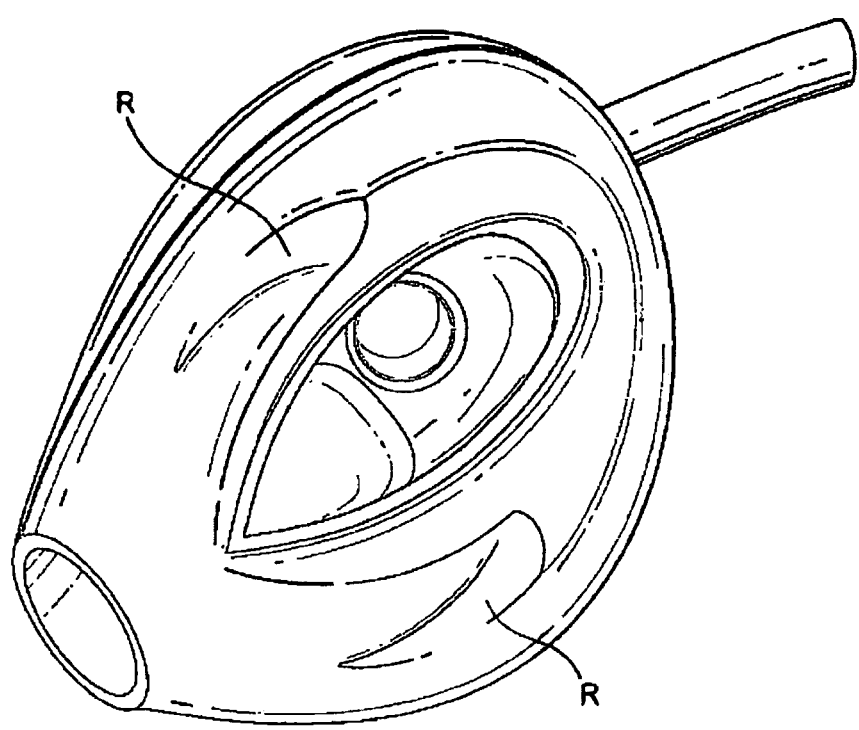
FIGS. 33 to 35 show underneath, front perspective and rear perspective views of a sixth embodiment in an inflated condition.
Figure 34:
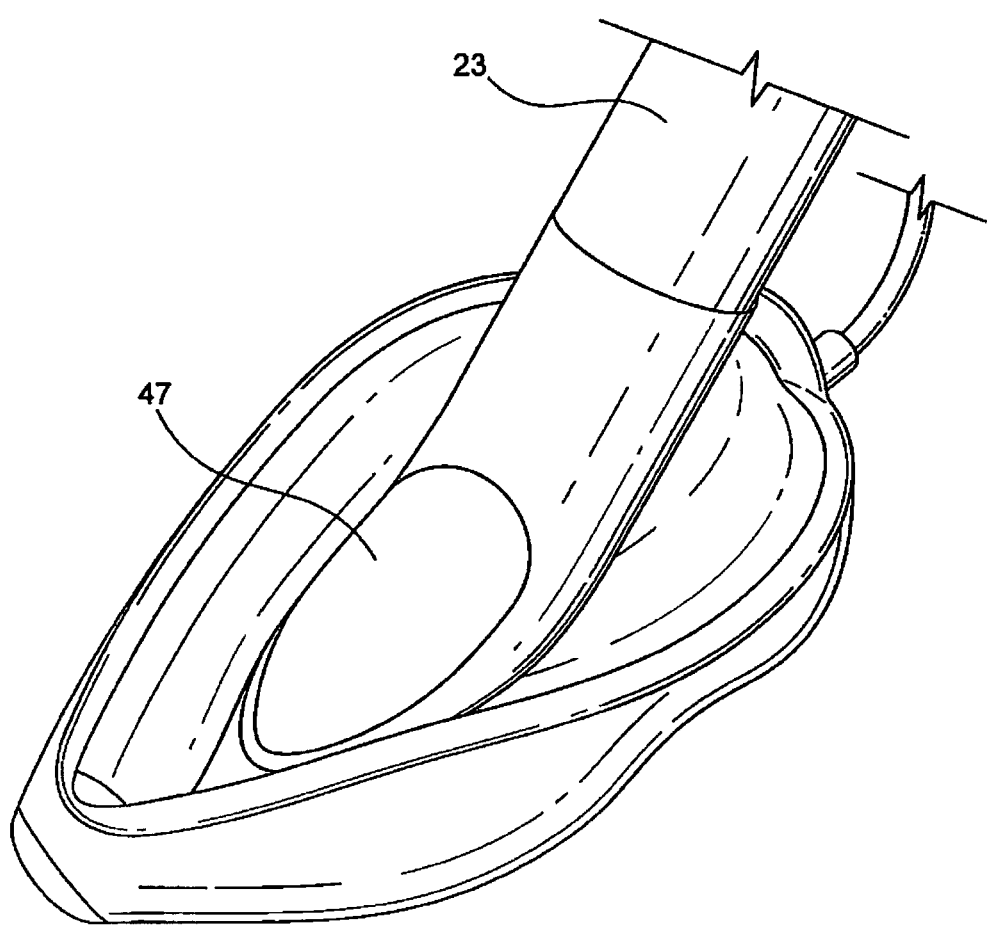
Figure 35:
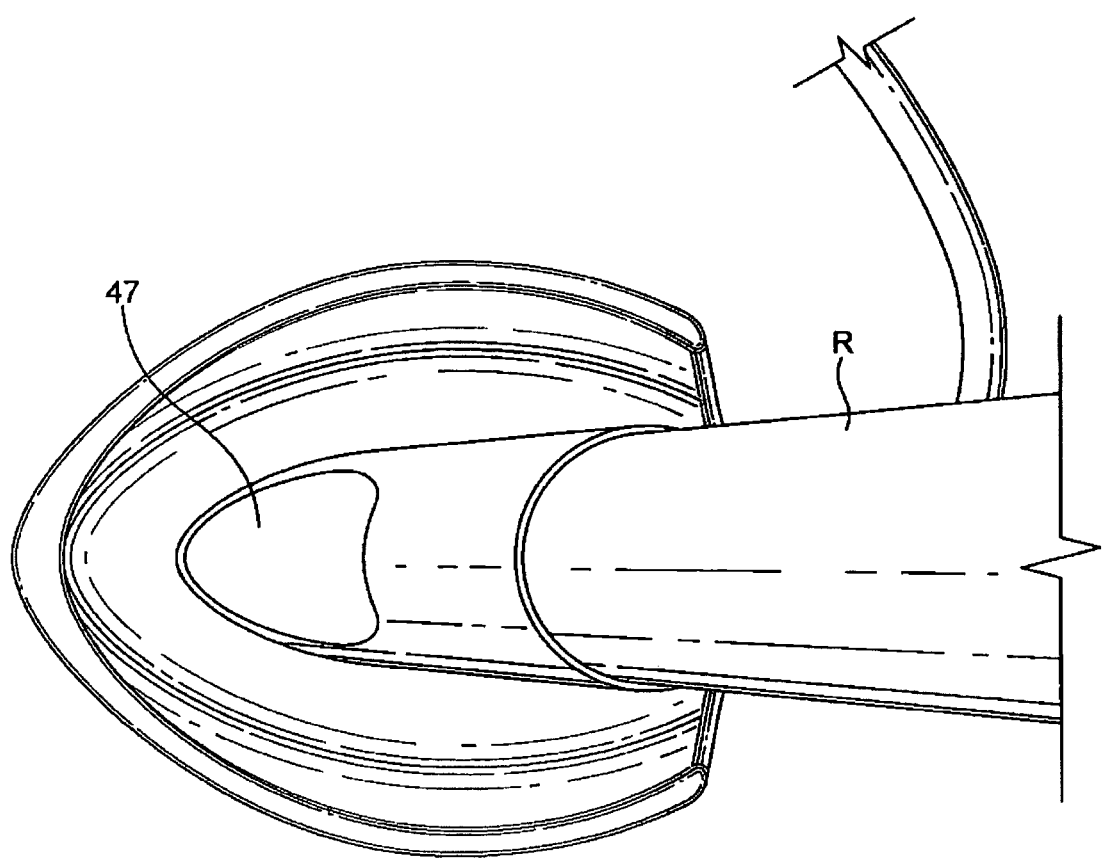
Figure 36:
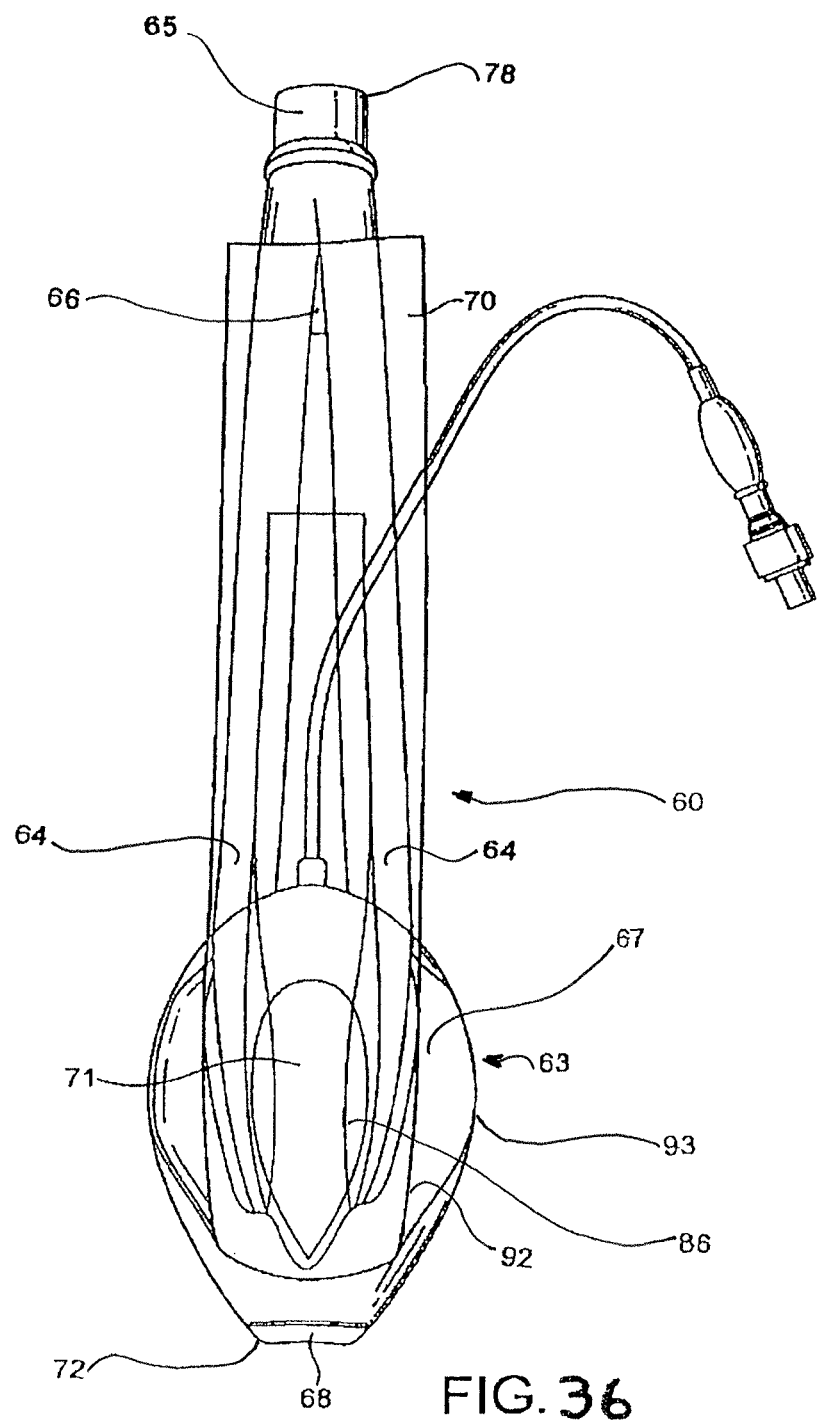
FIGS. 36 to 37 show top plan (dorsal side) and front (distal end) elevation views of a seventh embodiment of the present embodiment in a deflated condition
Figure 37:
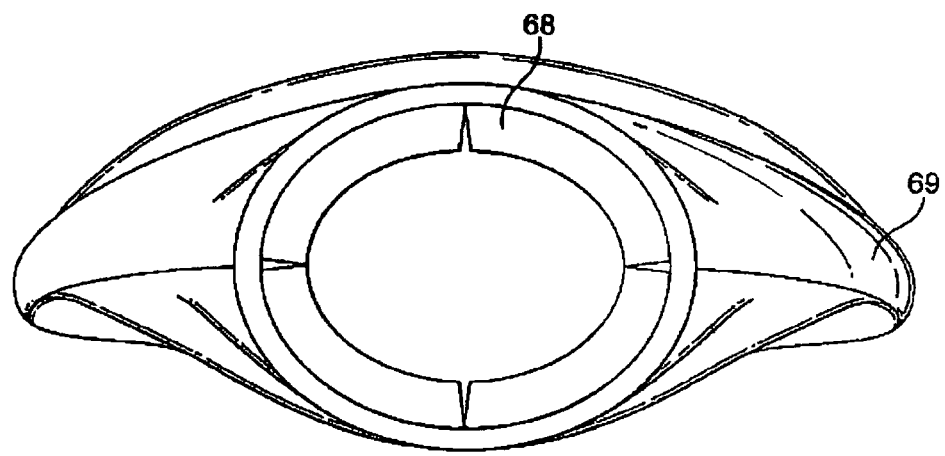
Figure 38:
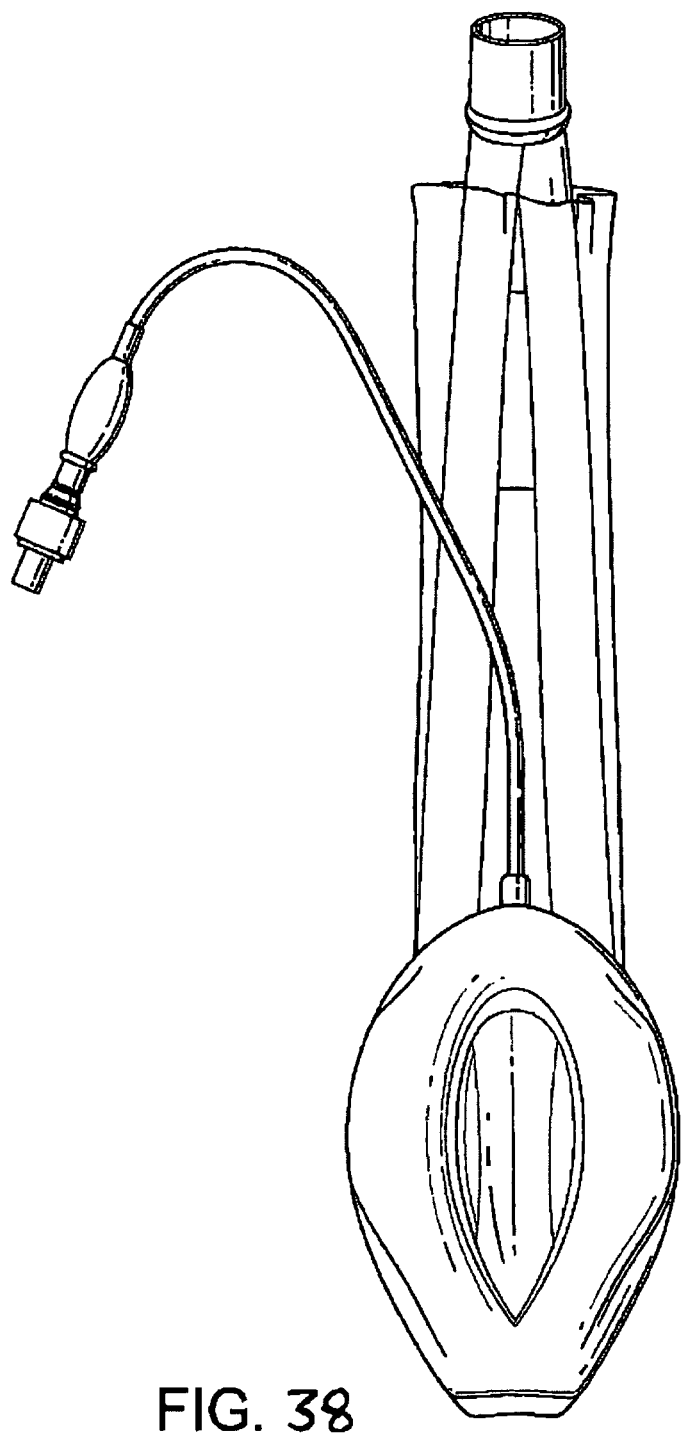
FIGS. 38 to 39 show underside (ventral side) and front (distal end) elevation views of the seventh embodiment in an inflated condition.
Figure 39:
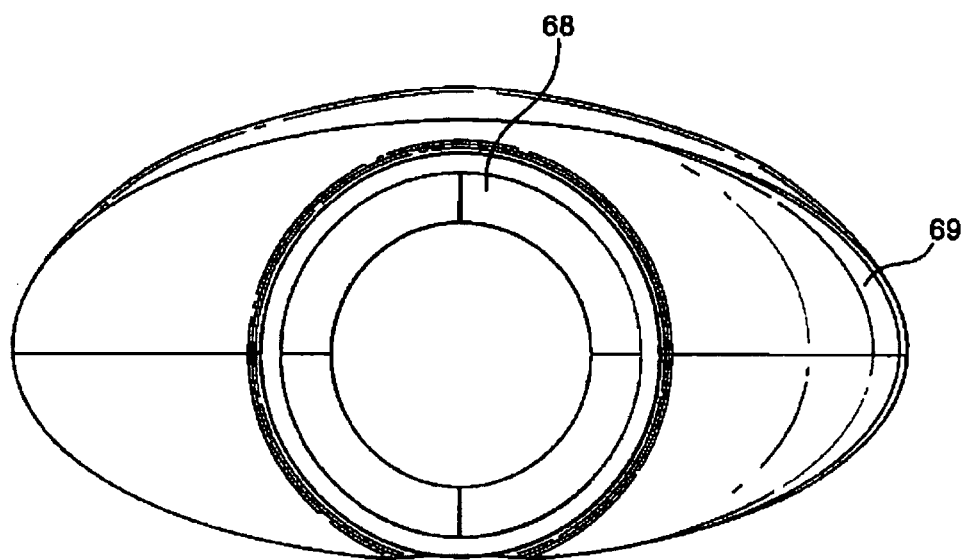
Figure 40:
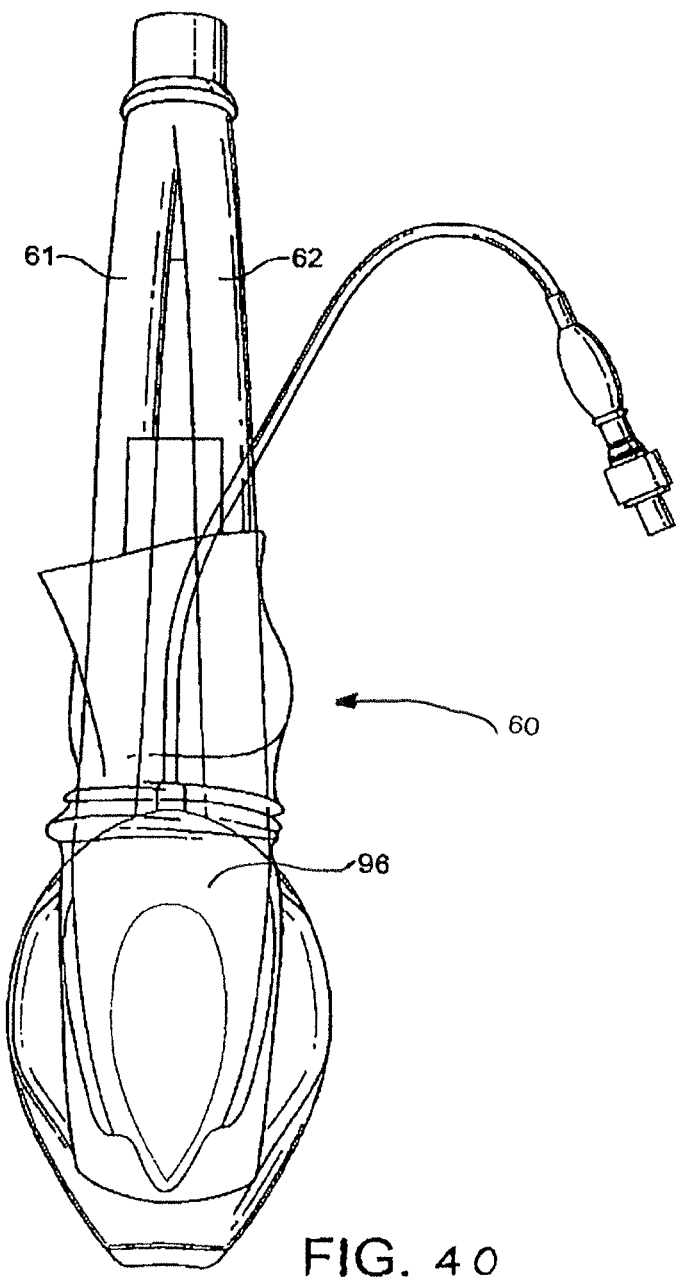
FIG. 40 shows a view of the seventh embodiment in which a flexible sheath has been rolled down to more clearly show two airway tubes of the seventh embodiment.
Figure 41:
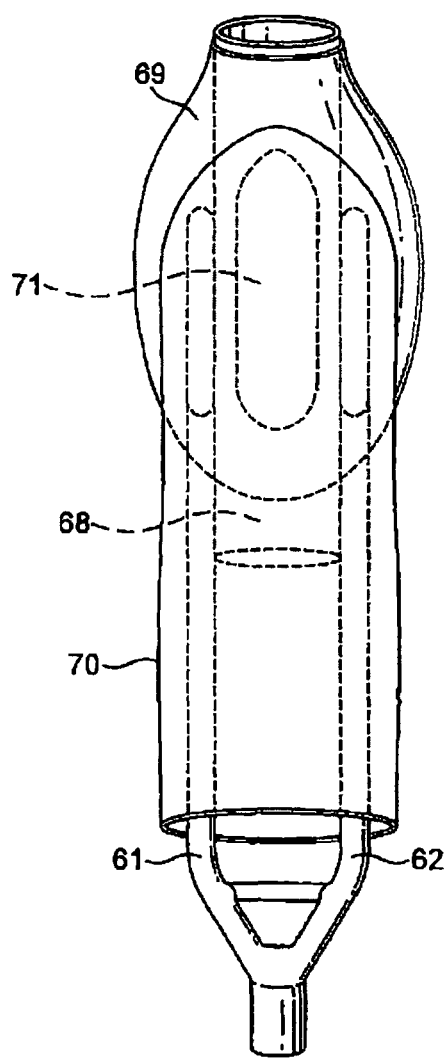
FIGS. 41 and 42 are line drawings of the ventral side of the mask and a side elevation view thereof.
Figure 42:
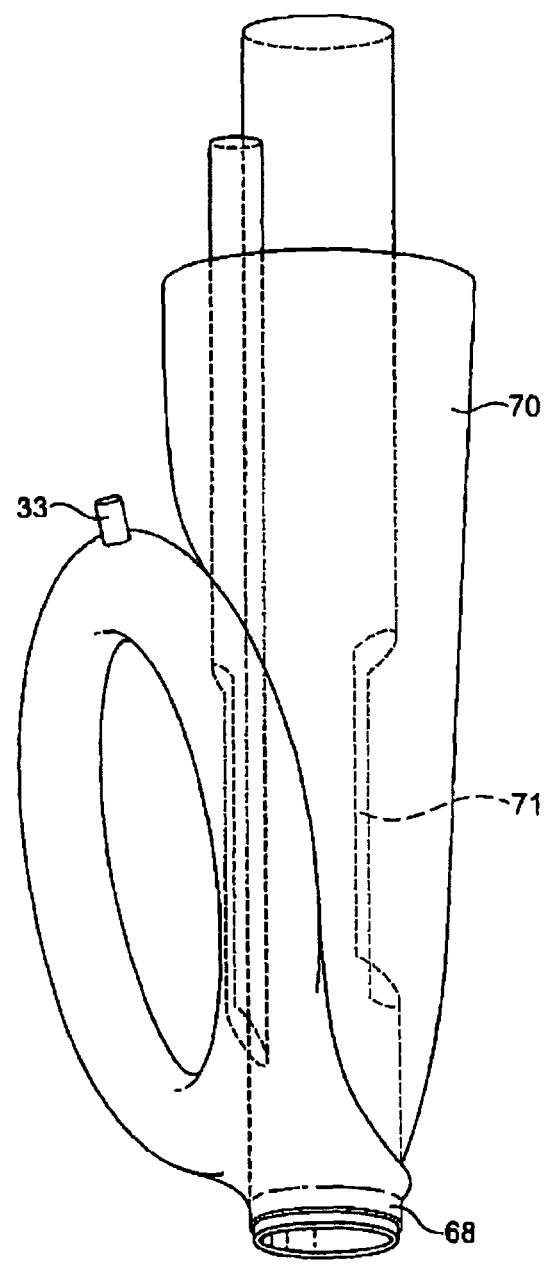
Figure 43:
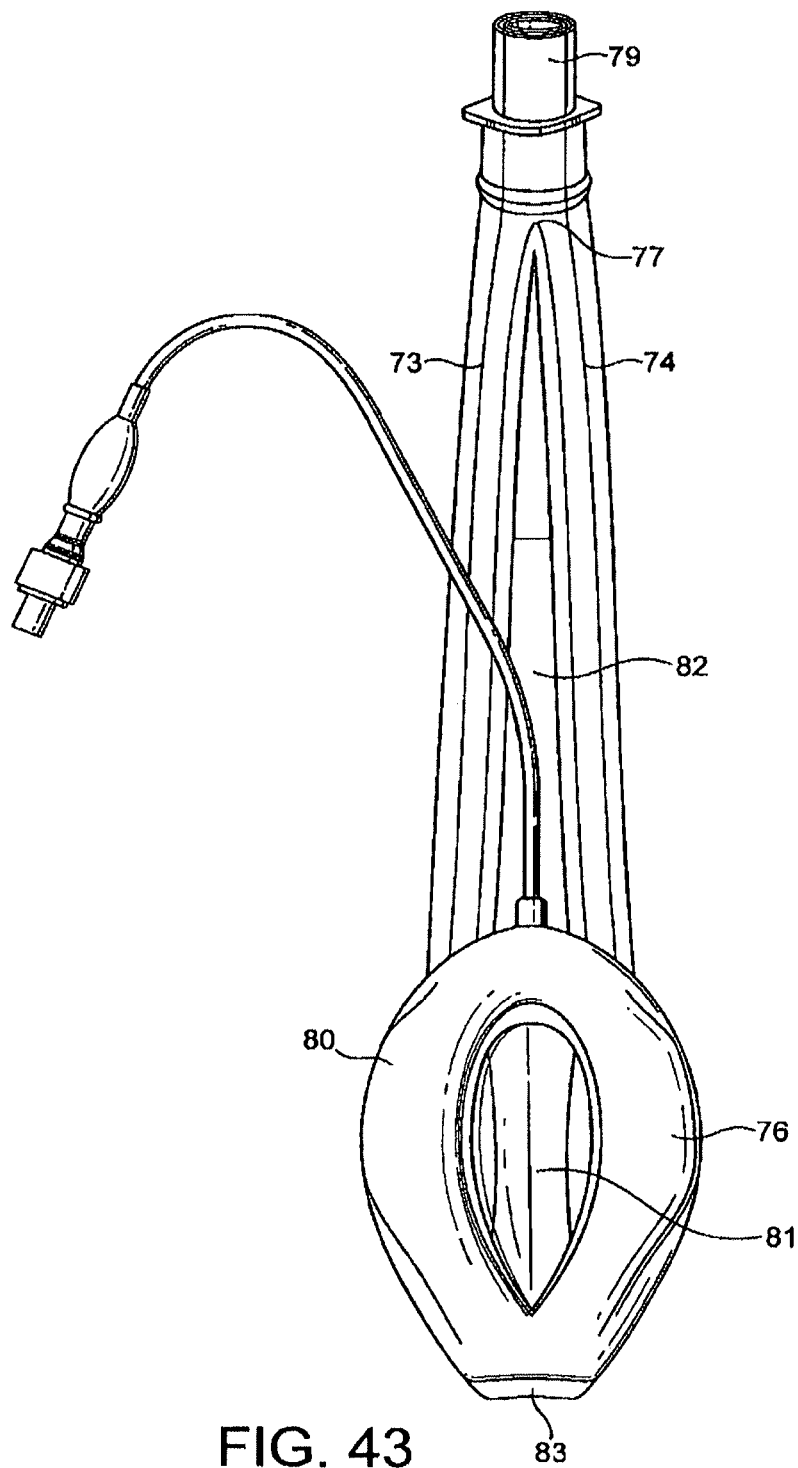
FIGS. 43 to 46 show underside (ventral side), top plan (dorsal side), side elevation, and front (distal end) elevation views of an eighth embodiment of the present embodiment in a deflated condition.
Figure 44:
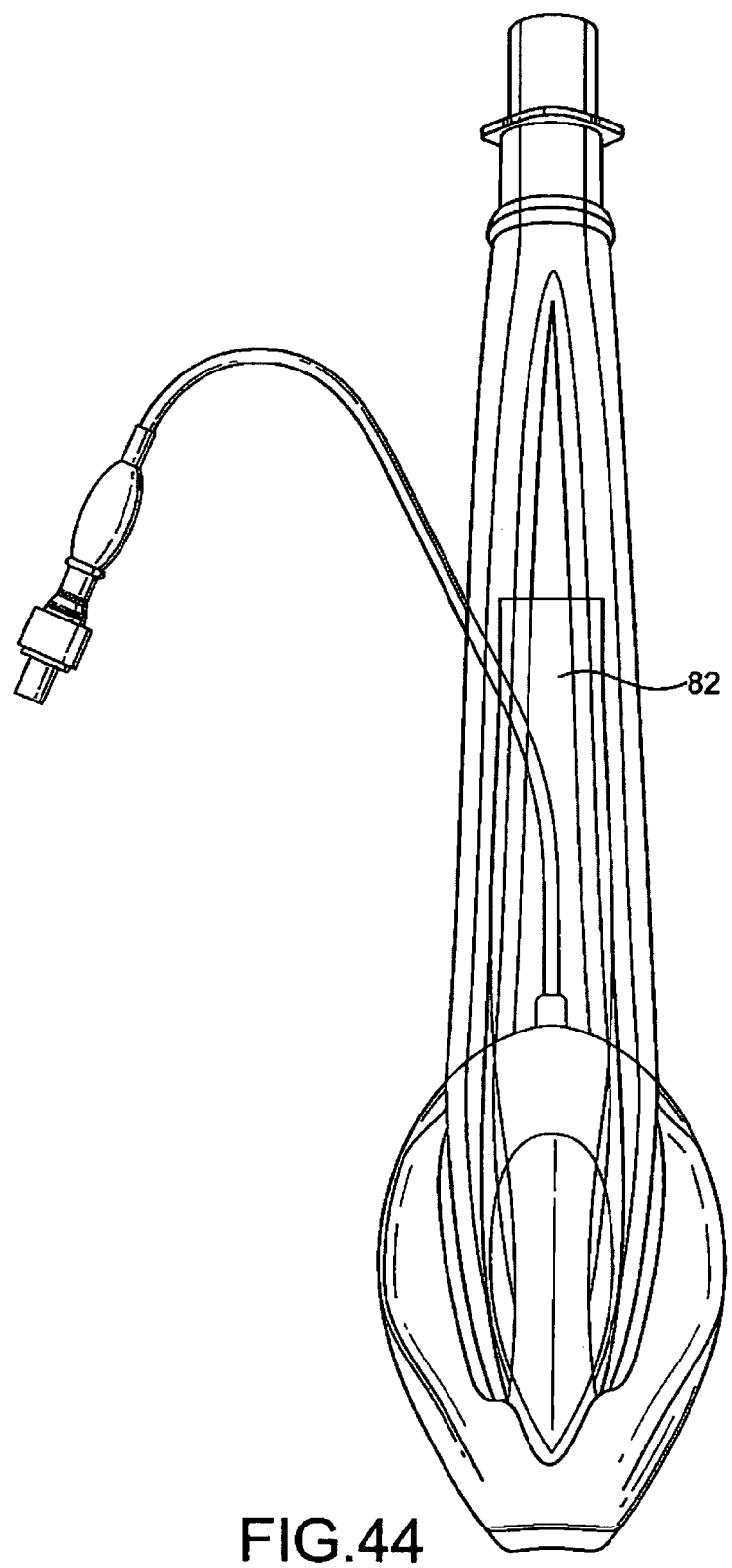
Figure 45:
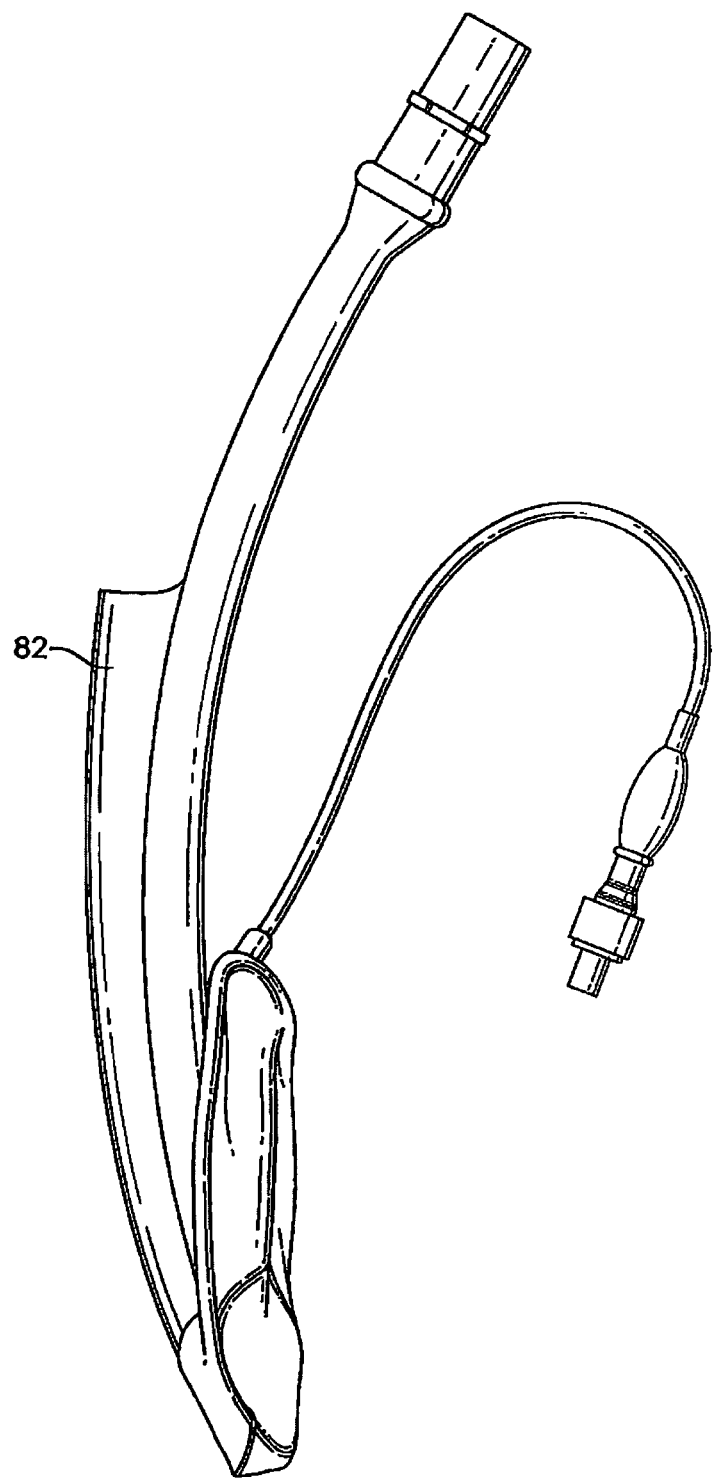
Figure 46:
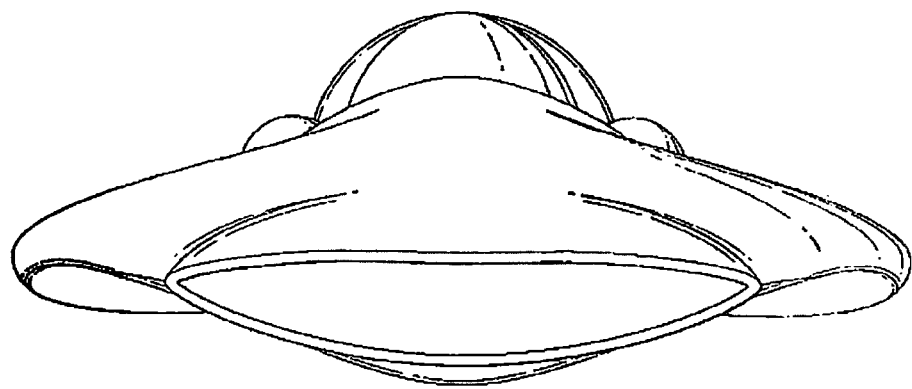
Figure 47:
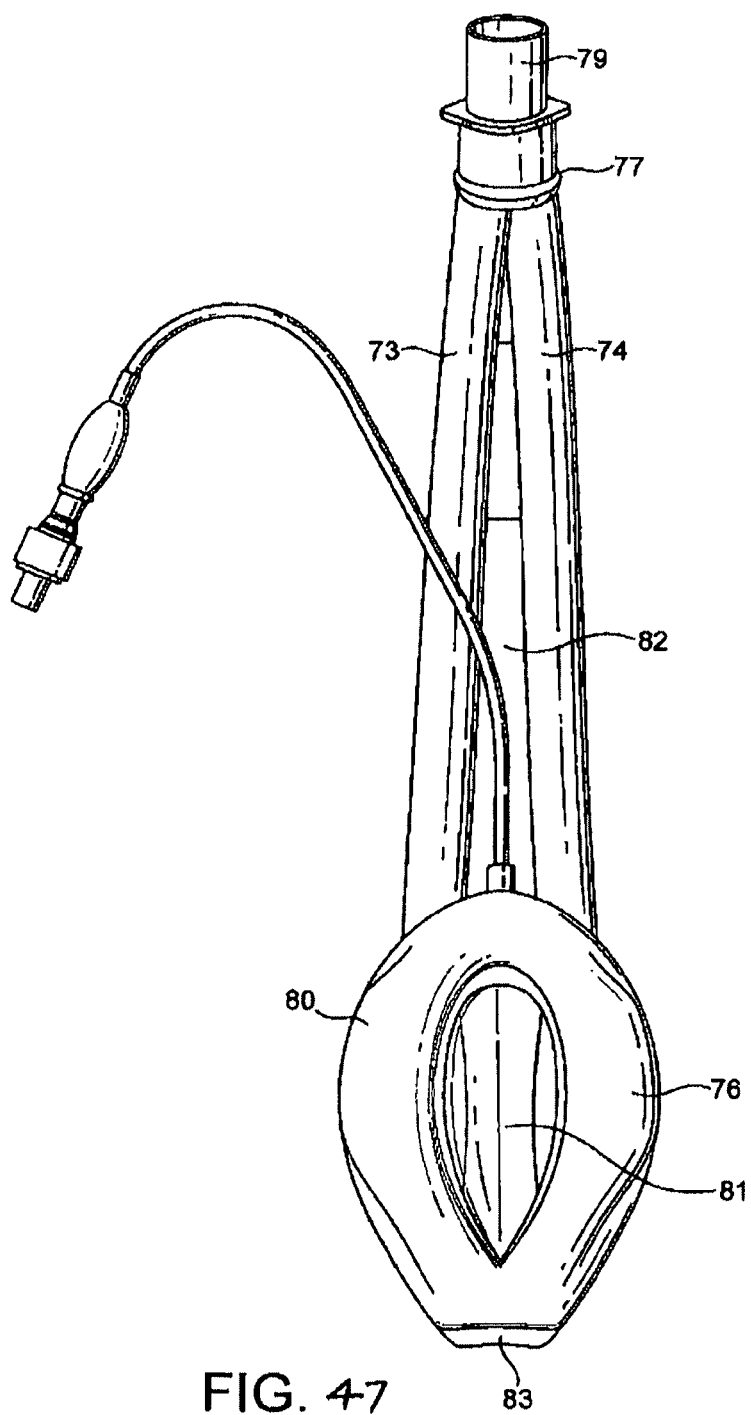
FIGS. 47 to 50 show underside (ventral side), top plan (dorsal side), side elevation, and front (distal end) elevation views of the eighth embodiment in an inflated condition.
Figure 48:
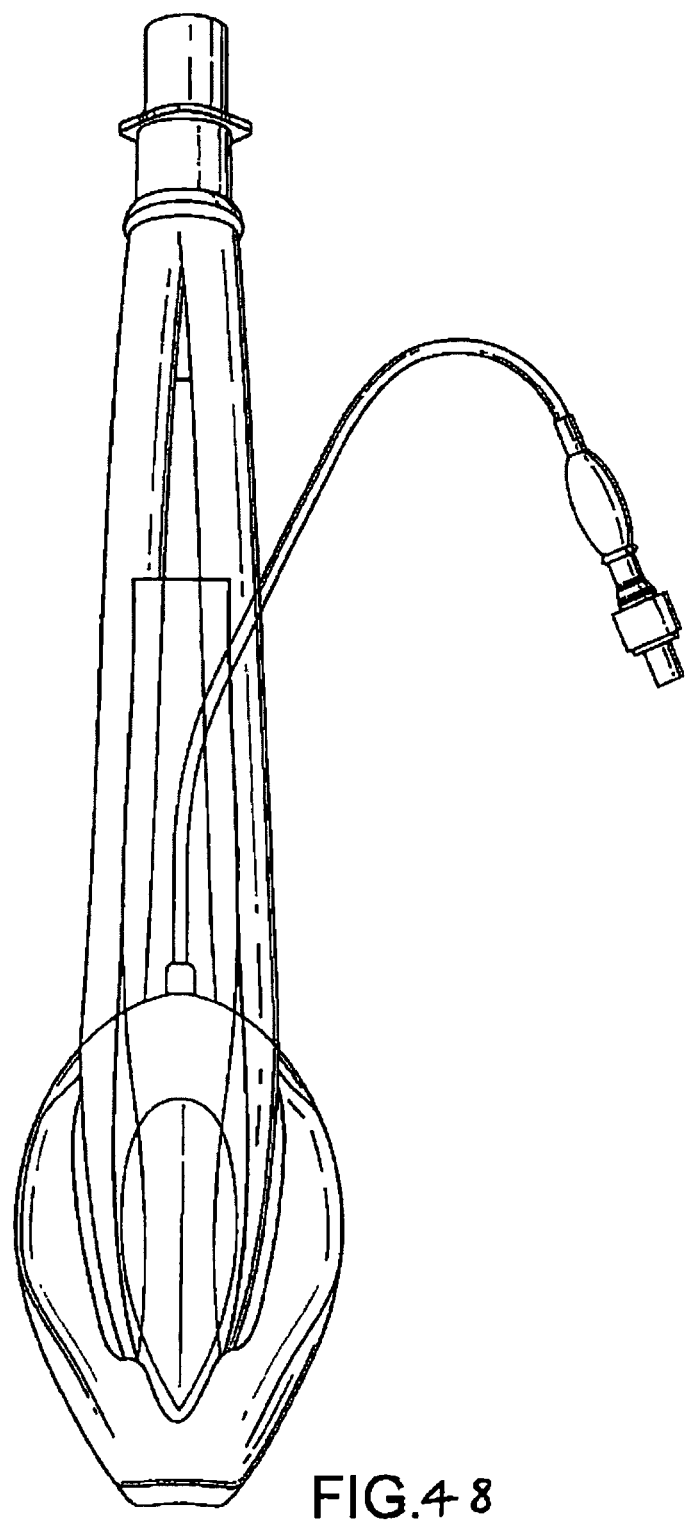
Figure 49:
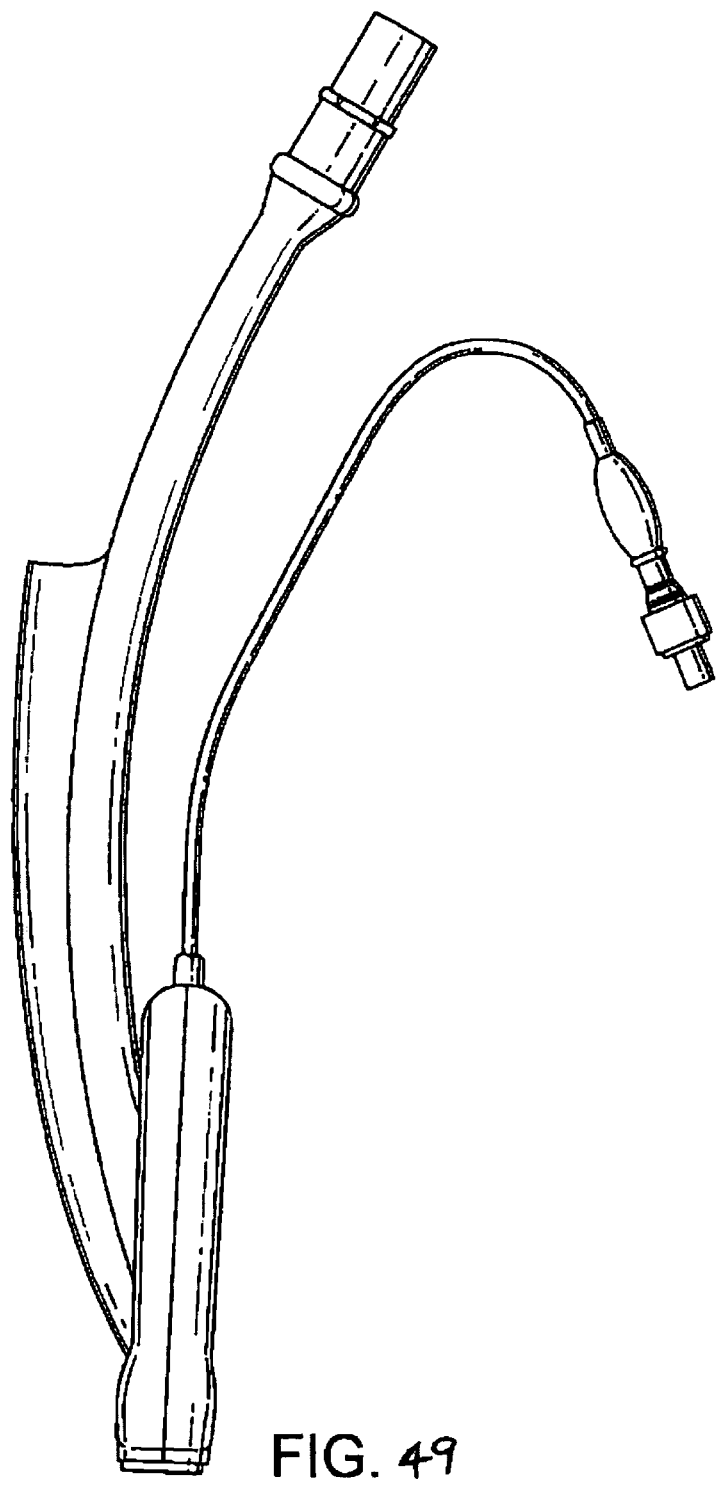
Figure 50:
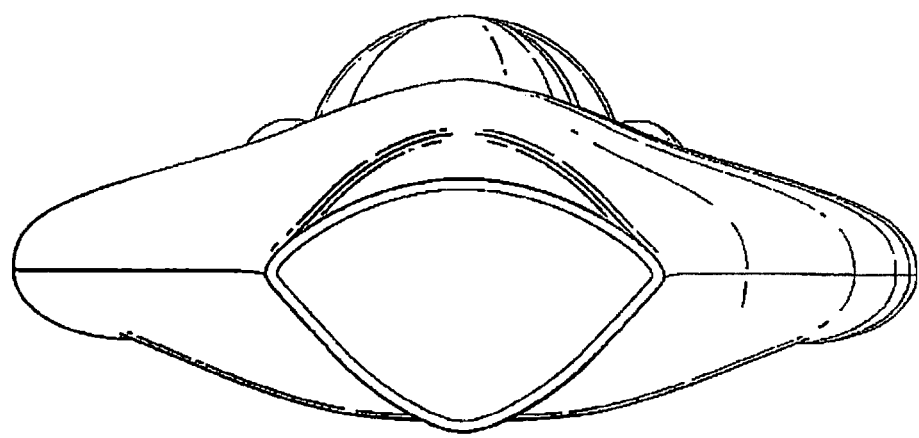
Figure 51:
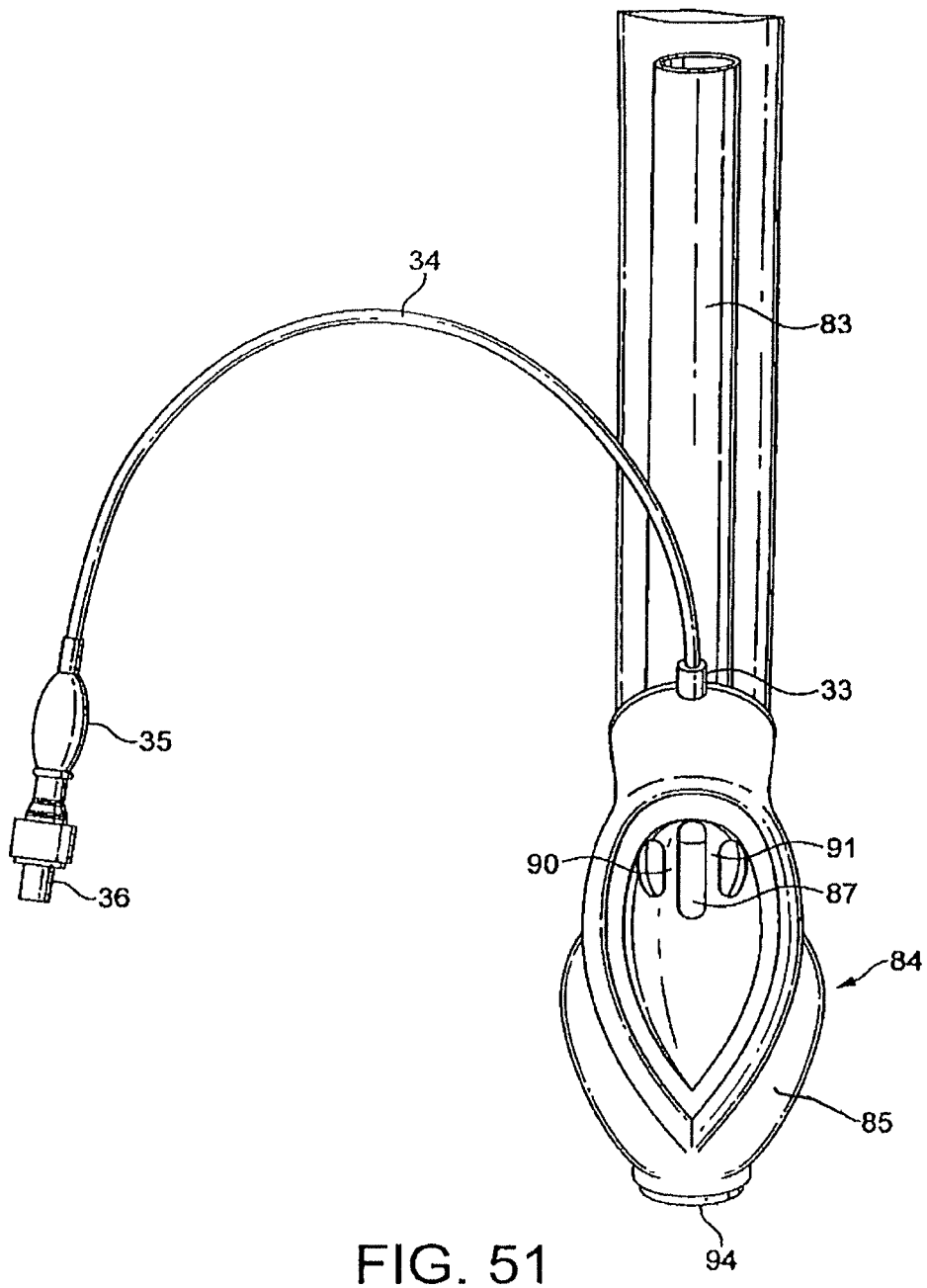
FIGS. 51 to 54 show underside (ventral side), top plan (dorsal side), side elevation, and front (distal end) elevation views of a ninth embodiment of the present embodiment in a deflated condition.
Figure 52:
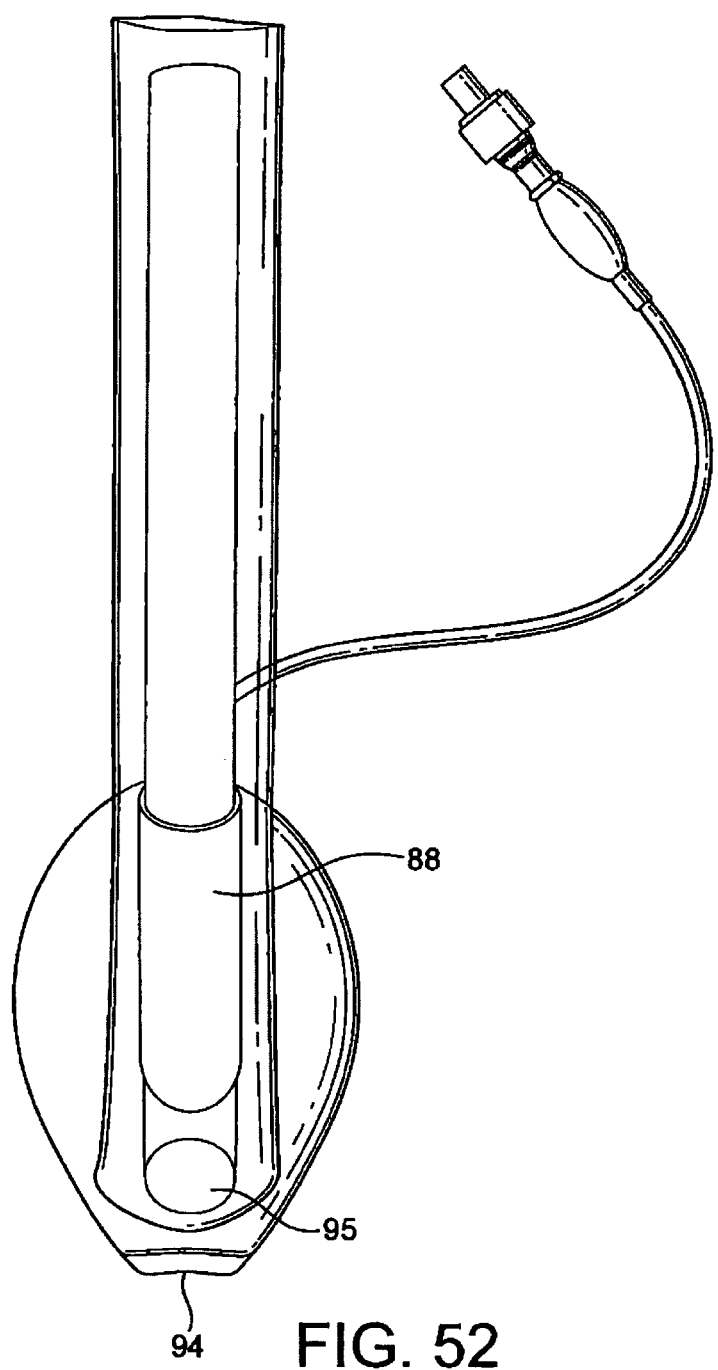
Figure 53:
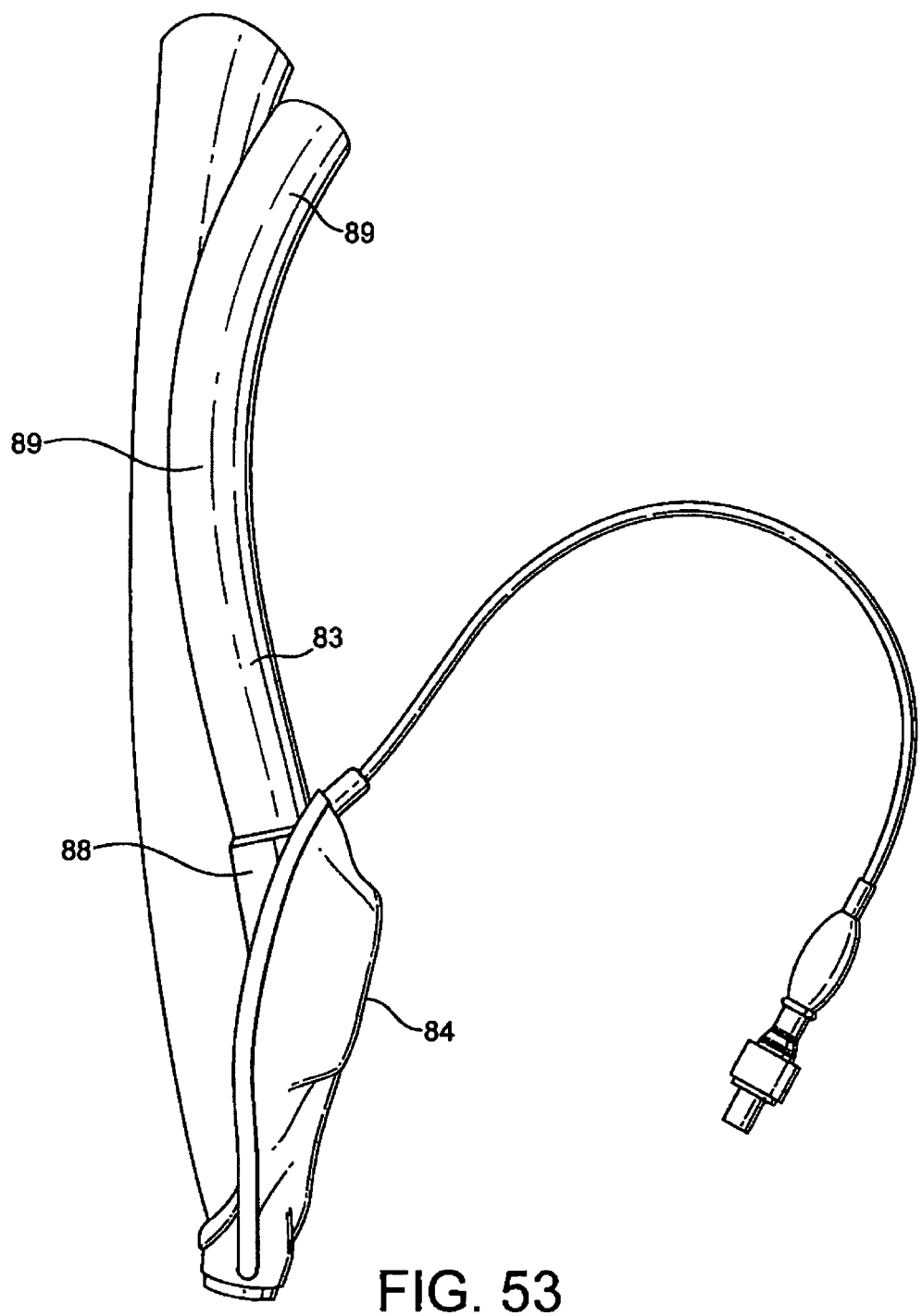
Figure 54:
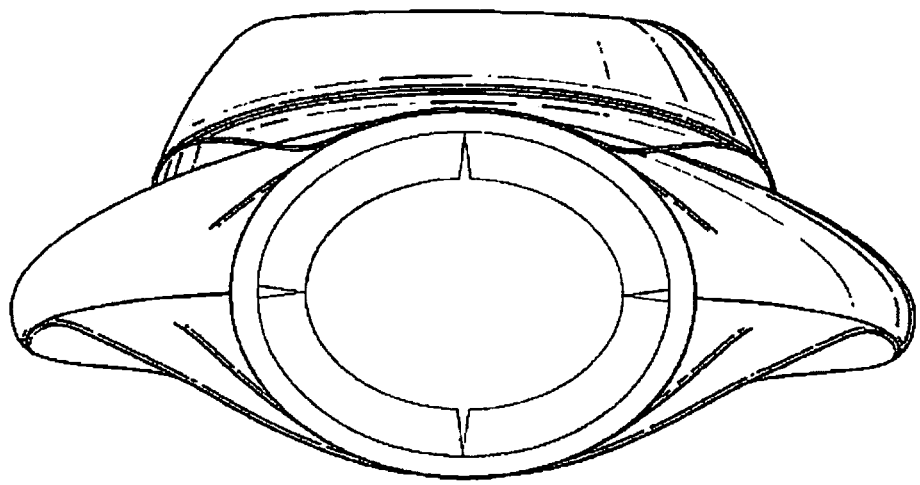
Figure 55:
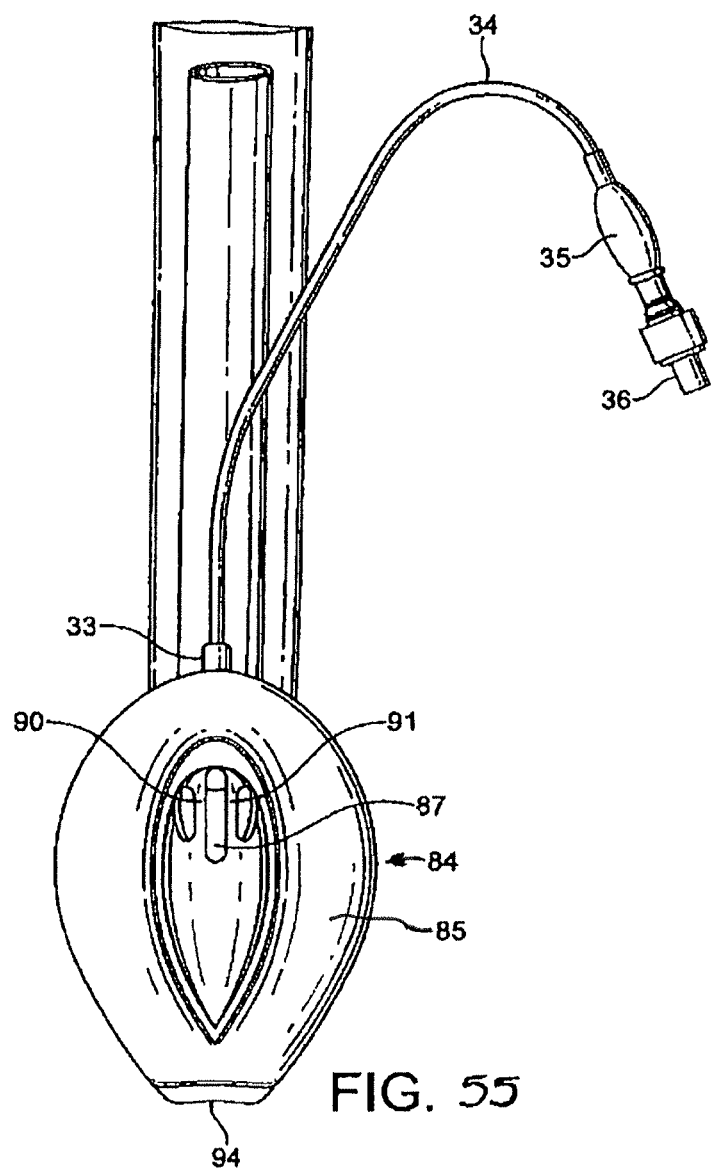
FIGS. 55 to 58 show underside (ventral side), top plan (dorsal side), side elevation, and front (distal end) elevation views of the ninth embodiment in an inflated condition.
Figure 56:
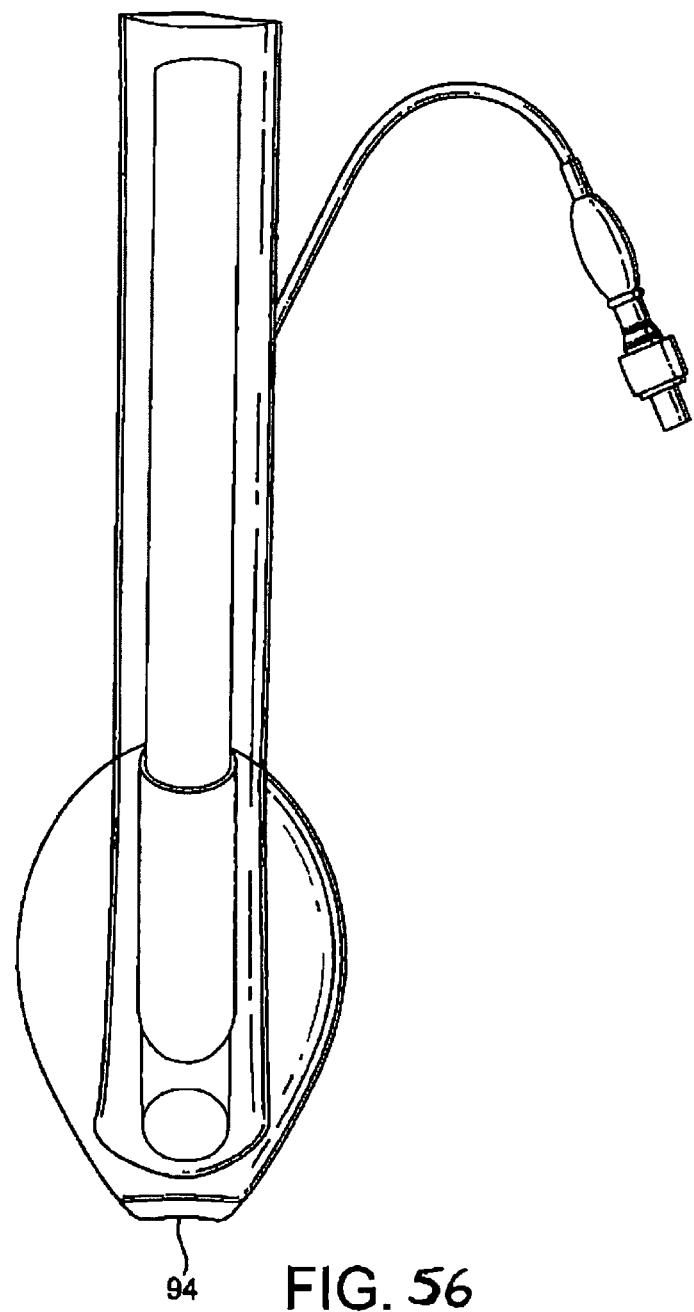
Figure 57:
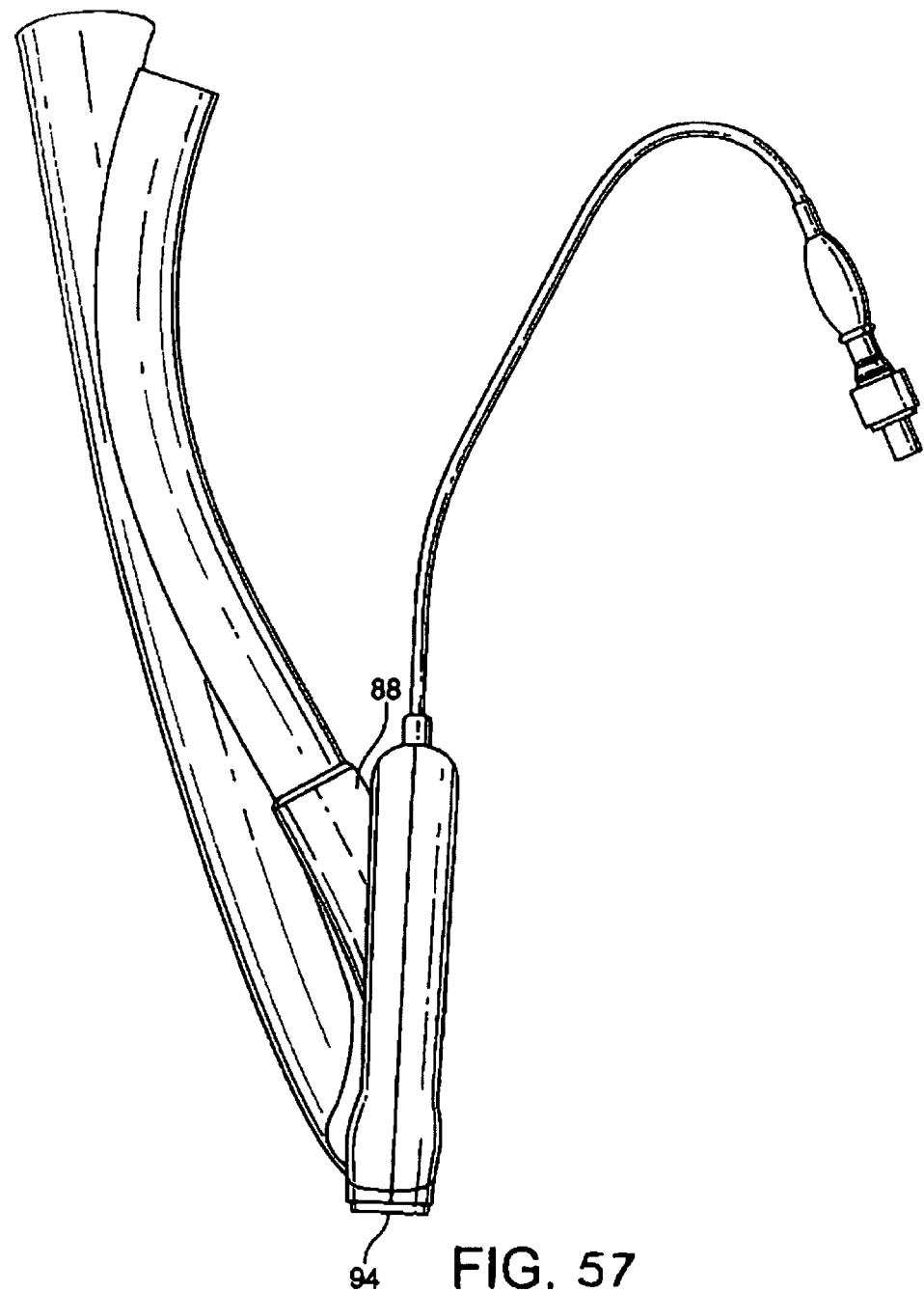

A sixth embodiment is shown in FIGS. 33 to 35. The sixth embodiment differs from the fourth embodiment in that the back-plate is cut away in the regions R indicated in FIG. 35 to avoid excessive pressure on the posterior surface of the cricoid cartilage. The function of the muscles covering this cartilage may otherwise become compromised and since these muscles (the posterior crico-arytenoid muscles) are necessary to maintain the lateral pull on the vocal cords which keeps the larynx open, avoidance of impairing their function is of great importance in maintaining a clear airway.

As will be appreciated by the skilled person, similar effects and advantages as in the fourth embodiment are achieved by the present embodiment.

A seventh embodiment is shown in FIGS. 36 to 42. According to this embodiment, the device 60 comprises a pair of airway tubes 61, 62 which open into the interior of a mask body 63 at the distal end of the device 60 and which join at a forked portion 64 to provide a single airway tube connection 65 at the proximal part of the device 60. A wedge portion 66 is provided between the airway tubes in the region of the forked portion.

The airway tubes 61, 62 themselves form the back plate of the mask 67, in conjunction with a gastric drainage tube 68 located between the airway tubes in the mask 67. To form the back plate, the top portion (ventral side) of each airway tube 61, 62 is cut off where it meets an inflatable cuff 69 which surrounds the mask body 63, one side of each tube is bonded to the underside {dorsal side) of the cuff 69, and the other side of each tube is bonded to respective sides of the central gastro-drainage tube 68, which gastro-drainage tube 68 is further bonded to the dorsal side of the proximal region of the cuff 69 to complete the back plate of mask 67.

Also bonded to the dorsal side of the cuff 69 is a curved flexible sleeve 70, into which the gastric-drainage tube 68 empties, and which surrounds the airway tubes 61,62 in a loose-fitting manner. A cut-out portion 71 (shown in phantom) is provided in the dorsal side of the drainage tube so as to facilitate the entry of gastric matter into the sleeve from the drainage tube, the other (inlet) end 72 of the gastric-drainage tube 68 protruding through the distal end of the cuff 69. The inlet of the gastric-drainage tube is provided by a hinged tube having an internal diameter of approximately 10 mm, similar to the variation of the first embodiment, and which thus facilitates the collapse and hence insertion of the device upon deflation of the cuff, but at the same time permits a large-diameter drainage tube to be provided within the patient once the mask is inflated, as on insertion the mask is intended to be in an uninflated state, wherein the inlet of the gastric drainage tube effectively closes up. The length of the drainage tube from the inlet 72 to the point at which the cut-out portion begins is approximately 24 mm, the length of the cut-out portion extends for approximately 50 mm along the axial length of the drainage tube and the length of the drainage tube as a whole is approximately 93 mm, although the present invention is of course not limited to these specific dimensions.

Similar to the above embodiments, the cuff 69 is provided with a port 33 into which one end of a small diameter inflation tube 34 is fitted in a gas-tight manner. The other end of the inflation tube is provided with an inflation indication bladder 35 and a valve 36, through which air is fed or extracted to inflate or deflate the cuff 69.

As in the above embodiments, the cuff 69 is first deflated to facilitate insertion of the device 60 into a patient, and subsequently inflated once the mask is in place with the distal end seated in the oesophageal upper sphincter and the interior of the mask closed over the inlet to the larynx.

In the event of gastric discharge, any gastric material is passed into the sleeve 70 via the gastric tube 68. In the event of the patient vomiting, the high-speed, low pressure gastric matter from the upper oesophageal sphincter is quickly passed by the relatively short-length of gastric tube into the plastic sleeve 70, which may readily expand so as to adopt a large diameter. The pressure of the vomited matter thus increases in the flow channel of the expanded sleeve 70, thus forcing the mask into further contact with the upper oesophageal sphincter.

Also, it will be appreciated that whilst the flexible sleeve 70 may provide a flow channel of large cross-sectional area when required, the sleeve 70 does not itself particularly restrict access through the pharynx, as it may simply fold and distort as required, nor, by virtue of being thin-walled, does it occupy a significant obstructing volume within the pharynx.

An eighth embodiment is shown in FIGS. 43 to 50.

Similar to the seventh embodiment, the eighth embodiment is provided with two airway tubes 73, 74 which open into the interior of a mask portion, which mask portion is encircled by an inflatable cuff 76. The airway tubes 73, 74 are joined at a forked portion 77 at the proximal end of the device 78 to provide a single airway connector 79.

The airway tubes 73, 74 themselves form the back plate of the mask 80, in conjunction with a gastric drainage tube 81 located centrally in the mask between the airway tubes. To form the back plate, the top (ventral) portion of each airway tube 73, 74 within the mask 80 is cut off, one side of each cut off portion of each tube is bonded to the underside (dorsal side) of the cuff 76, and the other side of each cut-off portion of each tube is bonded to a respective side of the drainage tube 81, which drainage tube is further bonded to the underside of the proximal end of the cuff 76 to complete the back plate of the mask 80.

The drainage tube 81 protrudes through the distal end of the cuff 76 and provides a channel through which gastric discharge may exit. The ventral side of the discharge tube is cut away from where it meets the posterior side of the cuff to form a discharge chute 82 extending from the posterior of the cuff for the continued guidance of gastric matter away from the mask 80.

The inlet of the gastric discharge tube is arranged so as to define a generally linear aperture or slit having a width of approximately 25 mm when the mask is uninflated. Inflation of the cuff results however in the inlet opening up, to form a large-diameter opening of generally circular cross-section with a diameter of approximately 17 mm. The objective of achieving this slit-shape of the distal end of the drain tube for insertion is to reduce the front-to-back diameter of the leading (distal) edge of the mask, so permitting it to pass easily into the normally closed-off space of the lower one-third of the pharynx. This permits a large-diameter gastric tube to be provided once the mask 80 is in place within the patient, but at the same time facilitates insertion of the mask into the patient, as on insertion the mask is intended to be in an uninflated state, wherein the inlet of the gastric drainage tube effectively closes up. The longitudinal length of the drainage tube which extends through the cuff i.e. up until the point at which the chute 82 begins is approximately 90 mm. and the axial length of the chute 82 is approximately 60 mm. The present invention is not however limited by the dimensions of the aperture, drainage tube and chute given above.

Figure 58:
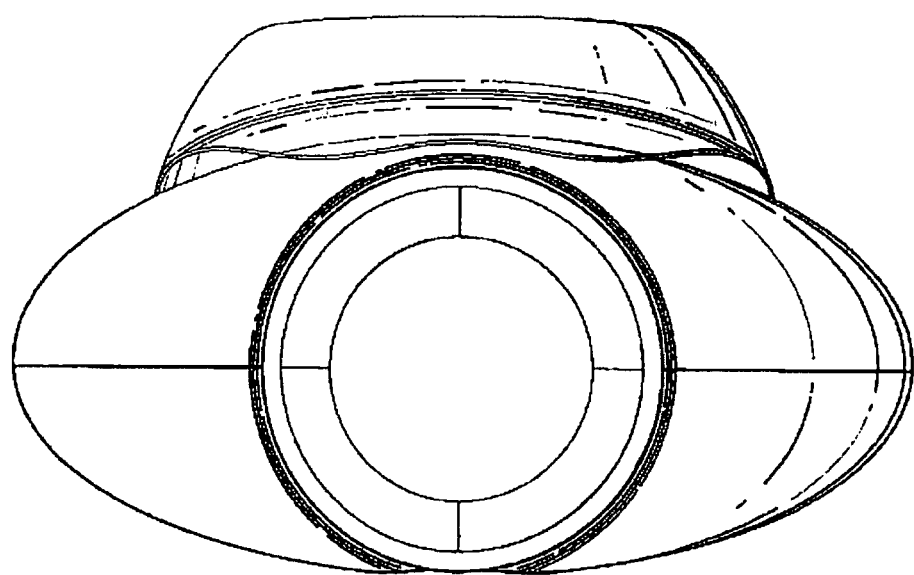
Figure 59:
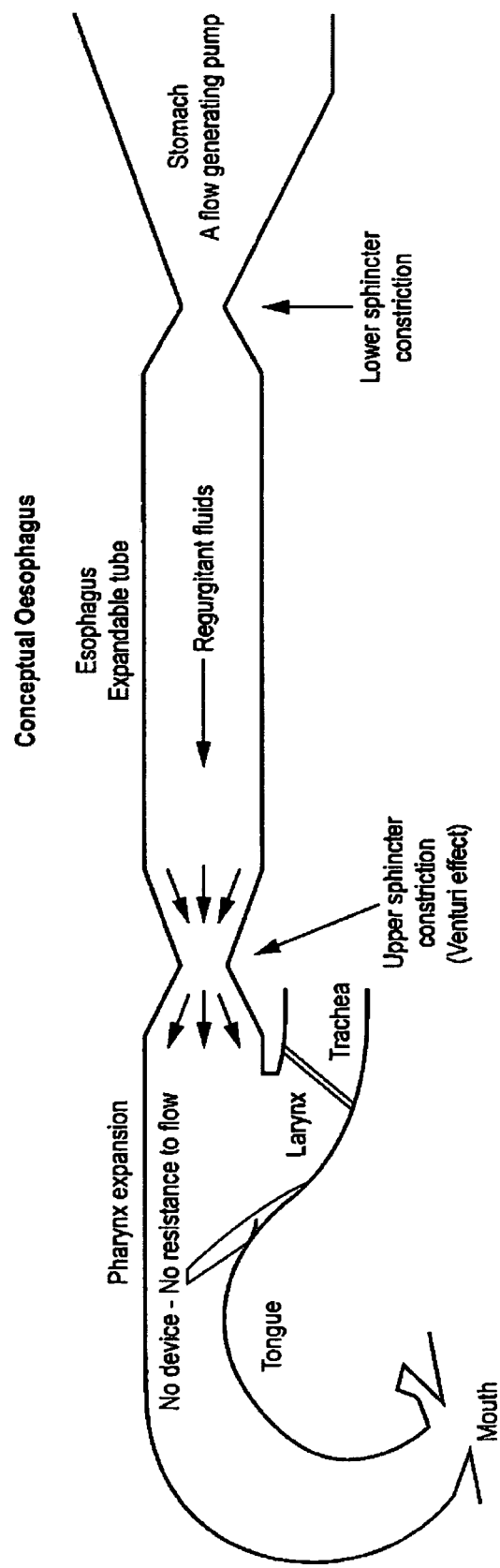
FIG. 59 illustrates a conceptual oesphagus during vomiting when no mask is present.
Figure 60:
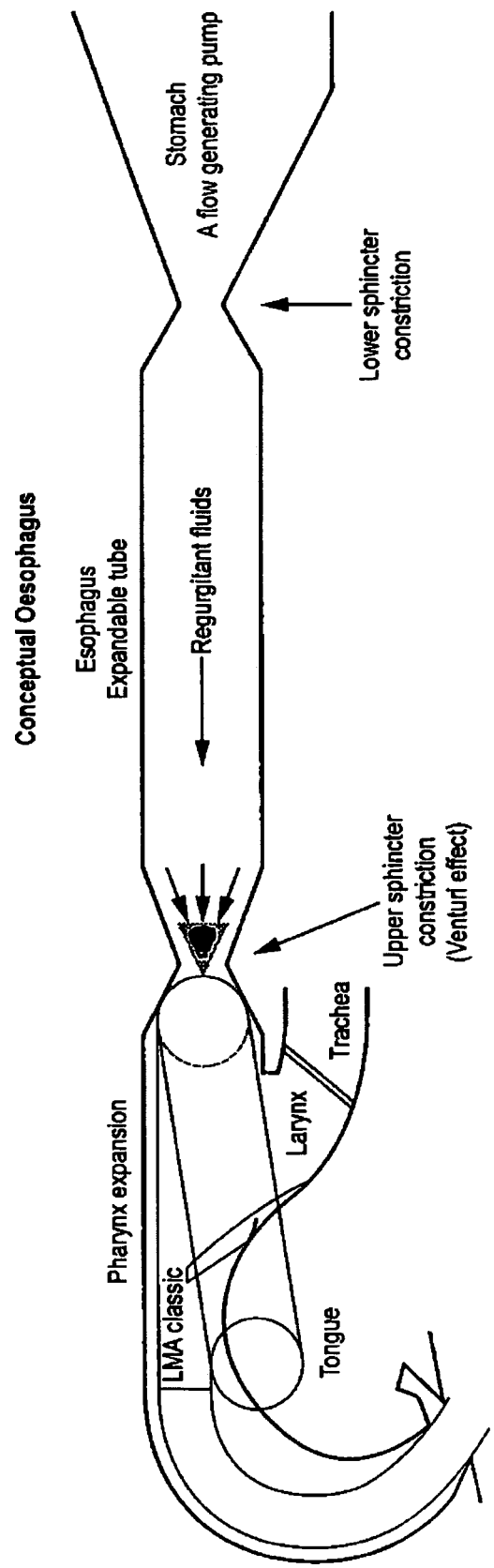
FIGS. 60 and 61 illustrate a conceptual oesphagus during vomiting when a mask for example according to U.S. Pat. No. 4,509,514 is present in the pharynx.
Figure 61:
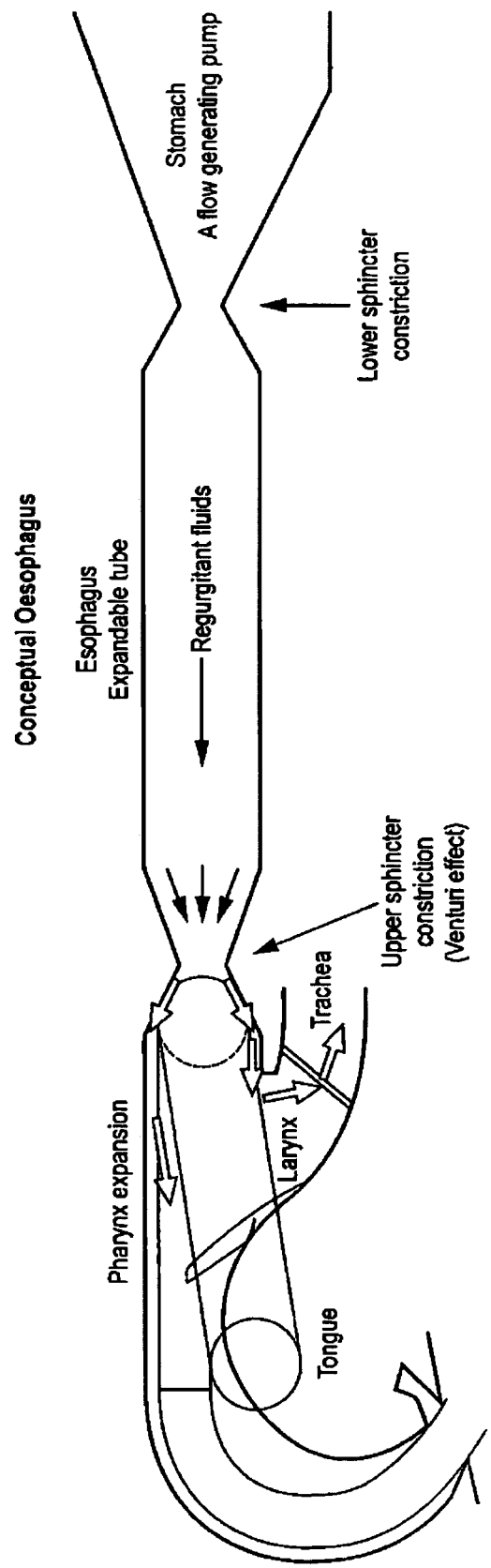
Figure 62:
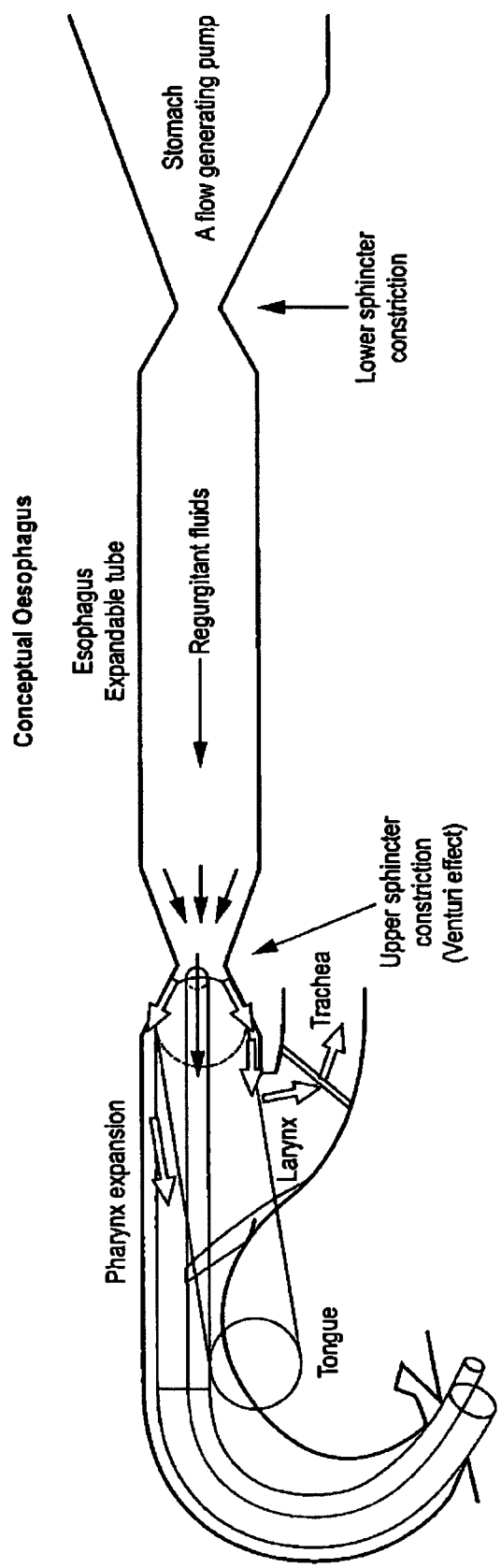
FIG. 62 illustrates a conceptual oesphagus during vomiting when a mask for example according to U.S. Pat. No. 5,241,956 is present in the pharynx.
Figure 63:
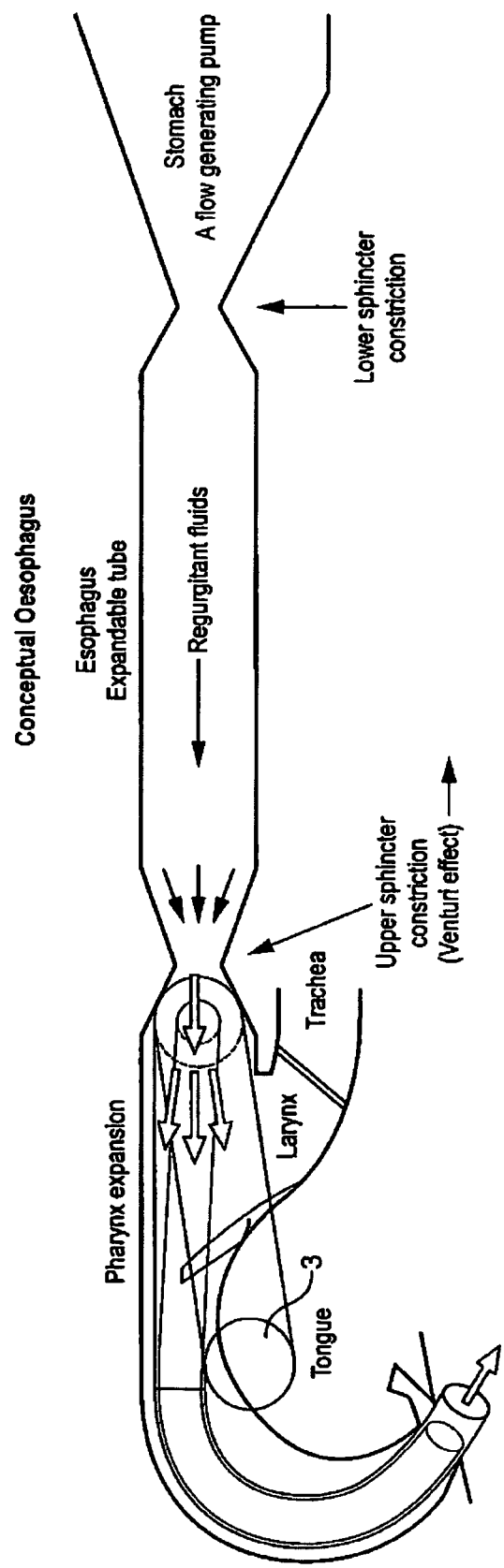
FIG. 63 illustrates a conceptual oesphagus during vomiting when a mask according to an embodiment of the present invention is present.

A ninth embodiment of the present invention is shown in FIGS. 51 to 58, and comprises a relatively rigid, curved airway tube 83 with a mask 84 attached at the distal end thereof. The body 85 of the mask is formed by an internal web 86 which defines the interior of the body of the mask 84 and which is provided with an aperture 87, and a semi-rigid back-plate which conforms to the generally oval shape of the web and which is adhered or otherwise secured to the rear thereof. The back-plate extends into a tubing portion 89, one end of which aligns with the aperture 87, and the other end of which receives the distal end of the airway tube 83, such that the airway tube 83 is in gaseous communication with the interior of the body 85 of the mask via the tubing portion 89 and the aperture 87. The airway tube 83 is provided with a flattened face on its dorsal side and provides an airway channel or lumen of substantially pentagonal cross-section, with one face thereof curved, as shown in FIG. 58. The airway tube is connected in an gas-tight manner into the tubing portion 89 by any suitable means, such as by welding or adhesive. The aperture 87 itself is provided with two flexible bars 90, 91 formed in the web, which bars stretch across the aperture and act to prevent the epiglottis of the patient from falling into the aperture and hence interrupting the airway when the mask is in place.

The periphery of the body of the mask is defined by an inflatable cuff 92, which is formed from a flexible sheet 93 of silicone which surrounds the periphery of the web 86 on the ventral side of the mask and which surrounds the periphery of the back plate 88 on the dorsal side of the mask. As in the first embodiment, the cuff 92 is provided with a port 33 into which one end of a small-diameter gas inlet tube 34 is affixed in a gas tight manner, to enable the supply of air to and from the cuff 92 via an inflation indicator bladder 35 and valve 36 at the other end of the gas inlet tube 34.

The inlet 94 of a short-lengthed gastric drainage tube 95 protrudes through the distal end of the cuff 92 and the outlet is aligned with a flexible sleeve 96 provided on the dorsal side of the device. In the present embodiment, the drainage tube is formed from a short length of hinged, collapsible extruded hosing as in the variation of the first embodiment. This again allows the inlet to adopt a configuration of a generally linear slit when the cuff is deflated to facilitate insertion of the device, and a generally circular cross-section of comparatively large cross-section, relative to prior art devices, when the cuff is inflated. When inflated, the internal diameter of the circular cross-section of the inlet is approximately 10 mm. The tube itself is cut at an angle to the axis of the tube at the posterior end of the tube, to match the contour of the cuff. The shortest axial length of the tube, at the dorsal side of the tube, is approximately 16 mm, and the longest length of the tube, at the ventral side of the tube, is approximately 30 mm. The present invention is not however limited to these dimensions.

The sleeve 96 is adhered to the flat surface of the airway tube and to the distal end of the cuff. Its thin wall is made of sufficiently high-durometer material to allow it to act as a semi-rigid posterior wall enclosing a space corresponding to the normal anatomical space available in the pharynx when there is no device in place. The sleeve is however otherwise free from connection with the remainder of the cuff 92.

The stiffness of the material of the sleeve is due to its high durometer, while it's flexibility is due to its thin wall. The stiffness may be translated as a relative lack of elasticity compared to lower durometer materials. As such, in a preferred embodiment, the sleeve is provided as a curved moulded shape to correspond to the anatomical curve of the upper pharynx and oral cavity.

A high durometer is preferred so that the part of the sleeve which forms a dome covering the back of the mask will resist collapse when in place within the patient with the mask inflated, so as to create a space behind the mask approximating that which would otherwise be present when the mask is not inserted.

Similar to the eighth embodiment, a large cross-section flow channel is thus provided as required by the sleeve 96 of the ninth embodiment, and similar effects and advantages as in the preceding embodiments may potentially be achieved.

Thus, it can be seen that the above described embodiments address the problems of prior art devices in novel and inventive ways.

Features of the above-described embodiments may be re-combined into further embodiments falling within the scope of the present invention. Further, the present invention is not limited to the exemplary materials and methods of construction outlined above in connection with the exemplary embodiments, and any suitable materials or methods of construction may be employed.

For example, although the cuff may be formed using a sheet of soft flexible silicone rubber, other materials such as latex or PVC may be used. PVC as a material is particularly suited to embodiments intended for single use, whereas the use of silicone rubber is preferred although not essential for embodiments intended to be re-used in a number of medical procedures.

Further, for example, the sheet of the cuff may be integrally formed with the web, or provided as a separate piece from the web which is subsequently secured thereto e.g. by bonding with adhesive.

Further, and as would be appreciated by the skilled person, various features of the present invention are applicable to a wide range of different laryngeal mask airway devices, and the invention is not limited to the exemplary embodiments of types of mask described above.

For example, aspects of the invention may be applied to laryngeal mask airway devices featuring epiglotic elevator bars over the mask aperture, which bars are operable to lift the epiglottis of a patent away from the aperture upon insertion of an endotracheal tube or other longitudinally-extended element inserted through the airway tube so as to emerge into the hollow or lumen of the mask through the mask aperture. Aspects of the present invention may for example be applied to single or re-useable devices, devices featuring aperture bars or not, "intubating" devices which permit an endotracheal tube or similar to be introduced into the larynx via an airway tube of a mask, devices incorporating fiberoptic viewing devices and so forth, without restriction or limitation on the scope of the present invention.

The invention claimed is:

1. An artificial airway device to facilitate lung ventilation of a patient, comprising:
   at least one airway tube and a mask carried at one end of the at least one airway tube,
   the mask having an inflatable peripheral formation capable of conforming to, and of readily fitting within, the actual and potential space behind the larynx of the patient so as to form a seal around the circumference of the laryngeal inlet,
   the peripheral formation surrounding a hollow interior space or lumen of the mask and the at least one airway tube opening into the lumen of the mask,
   the device further comprising a backplate bounded by the peripheral formation;
   characterized in that the mask provides a space for drainage of gastric matter leaving the oesophagus,
   wherein said space is an internal volume of the mask within the body of the mask forming a generally frusto-conical channel within the body of the mask, the space being surrounded by the peripheral formation and backplate; the space having an inlet at the distal end of the mask and an outlet at the posterior end of the mask, which outlet has a greater cross-sectional area than the inlet in the plane perpendicular to the longitudinal axis of the mask, in order to effect a significant rise in the pressure of fluid emerging from the oesophageal sphincter while still providing an inflatable mask shape which maintains the seal around the circumference of the laryngeal inlet.

2. The artificial airway device of claim 1, wherein the mask provides a space within the pharynx when the peripheral formation creates the seal around the laryngeal inlet.

3. The artificial airway device of claim 1, wherein the mask includes a portion which is moveable between a first condition and a second condition to provide the said space.

4. The artificial airway device of claim 1, wherein the peripheral formation includes a pair of lateral wings, a wing being attached on each side of the backplate and moveable relative thereto to create the space and provide for sealing.

5. The artificial airway device of claim 1 wherein the space is defined by a relatively soft-walled collapsible sheath.

6. The artificial airway device of claim 1 wherein the peripheral formation is an inflatable cuff.

7. The artificial airway device of claim 1, wherein the peripheral formation is a non-inflatable cuff.

8. The artificial airway device of claim 1, wherein the inlet comprises a collapsible ring.

9. The artificial airway device of claim 1, wherein the inlet comprises a U-shape formation.

10. The artificial airway device of claim 1, further comprising a means for receiving part of a device already inserted in the patient to facilitate the insertion of the artificial airway device by sliding the artificial airway device along the part of the device already inserted in the patient.

11. The artificial airway device of claim 10, said means comprising a receiving portion defined by the exterior surface of the artificial airway device.

12. The artificial airway device of claim 11, wherein the receiving portion comprises a channel formed in the exterior surface of the artificial airway device.

13. A method of facilitating lung ventilation in accordance with any one of claims 1, 2 or 3 to 12, the method comprising the step of inserting the device into a patient to maintain a seal around the circumference of the laryngeal inlet.

* * * * *